United States Patent
Smith et al.

(10) Patent No.: US 11,760,998 B2
(45) Date of Patent: Sep. 19, 2023

(54) HIGH-THROUGHPUT PRECISION GENOME EDITING

(71) Applicant: THE BOARD OF TRUSTEES OF THE LELAND STANFORD JUNIOR UNIVERSITY, Stanford, CA (US)

(72) Inventors: Zachery Smith, Sarasota, FL (US); Hunter Fraser, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1199 days.

(21) Appl. No.: 16/293,550

(22) Filed: Mar. 5, 2019

(65) Prior Publication Data

US 2019/0330619 A1    Oct. 31, 2019

Related U.S. Application Data

(63) Continuation of application No. PCT/US2017/050690, filed on Sep. 8, 2017.

(60) Provisional application No. 62/385,783, filed on Sep. 9, 2016.

(51) Int. Cl.

| | |
|---|---|
| *C12N 15/11* | (2006.01) |
| *C12N 9/22* | (2006.01) |
| *C12N 15/10* | (2006.01) |
| *C12N 15/81* | (2006.01) |
| *C12N 15/90* | (2006.01) |

(52) U.S. Cl.
CPC ............... *C12N 15/11* (2013.01); *C12N 9/22* (2013.01); *C12N 15/1079* (2013.01); *C12N 15/81* (2013.01); *C12N 15/905* (2013.01); *C12N 2310/12* (2013.01); *C12N 2310/20* (2017.05); *C12N 2800/80* (2013.01)

(58) Field of Classification Search
CPC ........ C12N 15/11; C12N 15/63; C12N 15/90; C12N 15/102; C12N 15/113; C12N 2310/12; C12N 2310/20; C12N 2800/80
USPC .... 435/6.1, 91.1, 91.31, 455, 458; 536/23.1, 536/24.5; 514/44 A, 44 R
See application file for complete search history.

(56) References Cited

U.S. PATENT DOCUMENTS

| 6,017,737 A † | 1/2000 | Inouye |
| 8,932,860 B2 | 1/2015 | Rozwadowski et al. |
| 2009/0123991 A1 † | 5/2009 | Rozwadowski |
| 2015/0089681 A1 † | 3/2015 | Van Der Oost |

FOREIGN PATENT DOCUMENTS

| EP | 1517992 B1 | 8/2013 | |
| WO | 2003/104470 A2 | 12/2003 | |
| WO | 2015/013583 A2 | 1/2015 | |
| WO | 2015153940 A1 † | 10/2015 | |
| WO | WO-2015153940 A1 * | 10/2015 | ........... C12N 15/111 |
| WO | 2016025719 A1 † | 2/2016 | |
| WO | WO-2016025719 A1 * | 2/2016 | ........... C12N 15/102 |
| WO | 2016/054326 A1 | 4/2016 | |
| WO | 2016/065364 A1 | 4/2016 | |
| WO | 2016054106 A1 † | 4/2016 | |
| WO | WO-2016054106 A1 * | 4/2016 | ........... C12N 15/113 |
| WO | 2018049168 A1 | 3/2018 | |

OTHER PUBLICATIONS

Ruff et al. (Nucleic Acids Research, vol. 42, No. 7, e61, pp. 1-16 (2014)) (Year: 2014).*
Third Party Submission (Year: 2019).*
EP17849615.4, "Extended European Search Report," dated Mar. 13, 2020, 7 pages.
Lampson et al., "Retrons, MsDNA, and The Bacterial Genome", Cytogenetic and Genome Research, vol. 110, No. 1-4, Jan. 1, 2005, pp. 491-499.
Mirochnitchenko et al., "Production of Single-stranded DNA in Mammalian Cells by Means of a Bacterial Retron", J Biol Chem, vol. 269, No. 4, Jan. 28, 1994, pp. 2380-2383.
PCT/US2017/050690, "International Preliminary Report on Patentability", dated Mar. 21, 2019, 11 pages.
PCT/US2017/050690, "International Search Report and Written Opinion", dated Feb. 5, 2018, 16 pages.
PCT/US2017/050690, "Invitation to Pay Add'l Fees and Partial Search Report," dated Dec. 7, 2017, 2 pages.
Simon et al., "A Diversity of Uncharacterized Reverse Transcriptases in Bacteria," Nucleic Acids Research, vol. 36, No. 22, Dec. 1, 2008, pp. 7219-7229.
Temin, "Retrons in Bacteria," Nature, vol. 339, May 25, 1989, pp. 254-255.
Communication from the Examining Division dated Jul. 3, 2007 issued during prosecution of the application for EP 1517992 B1.

(Continued)

*Primary Examiner* — Jane J Zara

(74) *Attorney, Agent, or Firm* — Kilpatrick Townsend & Stockton LLP

(57) ABSTRACT

The invention provides compositions and methods for high-efficiency genome editing. In some aspects, the invention provides retron-guide RNA cassettes and vectors comprising the cassettes. Also provided are host cells that have been transformed with the vectors. In other aspects, the invention provides retron donor DNA-guide molecules. In some other aspects, methods for genome editing and the screening of genetic loci are provided. In further aspects, methods and compositions are provided for the prevention or treatment of genetic diseases. Kits for genome editing and screening are also provided.

35 Claims, 11 Drawing Sheets

Specification includes a Sequence Listing.

(56) References Cited

OTHER PUBLICATIONS

Vora et al., "Next stop for the CRISPR revolution: RNA-guided epigenetic regulators", Febs J., 2016; 283:3181-3193, and information from the journal website showing an online publication date of Jun. 1, 2016, 15 pages.
Wikipedia entry for "Retron" dated Jun. 30, 2016, 3 pages.
Third party observations on European application No. 17849615.4 dated Jan. 6, 2023, 6 pages.
Farzadfard, Fahim et al., "Synthetic biology. Genomically encoded analog memory with precise in vivo DNA writing in living cell populations," Science (New York, N.Y.), vol. 346, issue 6211, pp. 1-8 (Nov. 14, 2014): 1256272. doi:10.1126/science.1256272 (8 pages).†
Prokup, Alexander et al., "Engineering a Bacterial Tape Recorder," ChemBioChem, Wiley Online Library, 16:1027-9 (Mar. 27, 2015); PMID:25821162; https://doi.org/10.1002/cbic.201500061 (3 pages).†
Ruff, Patrick et al., "Aptamer-guided gene targeting in yeast and human cells," Nucleic Acids Research, vol. 42, No. 7, pp. 1-16 (2014): e61.doi:10.1093/nar/gku101 (16 pages).†

\* cited by examiner
† cited by third party

FIG. 2 (cont'd)

```
GTTCCATTCTCTTGGTTATAATCGACTAATATCTTCAGTTTTGACAAAAAATATGTTGTTATAAAAAATCTGCTACCACAAGGTGCTCCATCATCACCTAAA
CAAGGTAAGAGAACCAATATTAGCTGATTAGAAGTCAAAACTGTTTTTATACAACAATATTTTTAGACGATGGTGTTCCACGAGGTAGTAGTGGATTT
                                                                                          >>>
            2,620                   2,640                   2,660                   2,680                   2,700
                                                            RT Ec86

TTAGCTAATCTAATATGTTCTAAACTTGATTATGTAATTCAGGGTTATGCAGGTAGTCGGGGCTTGATATATACGAGATATGCCGATGATCTCACCTTAT
AATCGATTAGATTATACAAGATTTGAACTAATAGCATAAGTCCCAATAGTCGTTCCATAGCCCGAACTATATGCTCTATACGGCTACTAGAGTGGAATA
                                                                                          >>>
            2,720                   2,740                   2,760                   2,780                   2,800
                                                            RT Ec86

CTGCACAGTCTGATGAAAAAGGTTGTTAAAGCACGTGATTTTTATTTCTATAATCCCAAGTGAAGGATTGGTTATTAACTCAAAAAAAACTTGTATTAG
GACGTGTCAGATACTTTTTTCCAACAATTCGTGCACTAAAAATAAAGATATTAGGGTTCACTTCCTAACCAATAATTGAGTTTTTTTGAACATAATC
                                                                                          >>>
            2,820                   2,840                   2,860                   2,880                   2,900
                                                            RT Ec86

TGGGCCCTCGTAGTCAGAGGAAAGTTACAGGTTTAGTTATTTCAACAAGTGTTGGGATAGGTAGAGAAAAATATAAAGAAATTAGAGCAAAGATACAT
ACCCGGGAGCATCAGTCTCCTTTCAATGTCCAAATCAATAAAGTTGTTCACGACCCTATCATCATCTCTTTTATATTCTTAATCTCGTTTCTATGTA
                                                                                          >>>
            2,920                   2,940                   2,960                   2,980                   3,000
                                                            RT Ec86

CATATATATTTGCGGTAAGTCTTCTGAGATAGAACACGTTAGGGGATGGTTGTCATTTATTTTAAGTGTGGATTCAAAAAGCCATAGGAGATTAATAACTT
GTATATATAAACGCCATTCAGAGACTCTATCTTGTGCAATCCCCTACCAACAGTAATAAAATTCACACCTAAGTTTTCGGTATCCTCTAATTATTGAA
                                                                                          >>>
            3,020                   3,040                   3,060                   3,080                   3,100
                                                            RT Ec86

ATATTAGCAAATTAGAGAAAAAAATATGGAAAGAACCCTTTAAATAAGCGAAGACCTAAATGGTCTTCGTTTTAAACTAAAGCTCATAGGTTGAAAAATT
TATAATCGTTTAATCTTTTTTTTATACCTTTCTTGGAAATTTATTTCGCTTCTGGATTACCAGACAAATTTGATTTCGAGTATCCAACTTTTTAA
                                                                                          >>>
            3,120                   3,140                   3,160                   3,180                   3,200
                                         RT Ec86

GAGCACTTCTCTTCGTCCAACCAGTTATTTAGTTCCTGCAATCGTTTCTGCAGGGCATCAATTCGTTCTTACGAATACCTTGCTAGCCTTCTCCACATCC
CTCGTGAAGAGAACAGGTTGGTCAATAAATCAAGACGTTAGCCCGTAAGACTTATGCTTAAGCAAAGAATGCTTATGGAACGATCGGAAGAGGTGTAGG
            3,220                   3,240                   3,260                   3,280                   3,300

CCAAACCCCCGACATTATTAGGCATAATTCCCATCAT
GGTTTTGGGGGCTGTGTAATAATCCGTATTAAGGGTAGTA
            3,320                   3,340
```

HIGH-THROUGHPUT PRECISION GENOME EDITING

CROSS-REFERENCE TO RELATED APPLICATIONS

This application is a continuation of International Patent Application No. PCT/US2017/050690, filed Sep. 8, 2017, which claims priority to U.S. Provisional Application No. 62/385,783, filed Sep. 9, 2016, the disclosures of which are herein incorporated by reference in their entirety for all purposes.

STATEMENT AS TO RIGHTS TO INVENTIONS MADE UNDER FEDERALLY SPONSORED RESEARCH AND DEVELOPMENT

This invention was made with government support under contract GM097171 awarded by the National Institutes of Health. The Government has certain rights in the invention.

BACKGROUND OF THE INVENTION

Genome editing with engineered nucleases is a breakthrough technology for modifying essentially any genomic sequence of interest (Porteus, M. H. & Carroll, D., *Nature Biotechnology* 23, 967-973 (2005)). This technology exploits engineered nucleases to generate site-specific double-strand breaks (DSBs) followed by resolution of DSBs by endogenous cellular repair mechanisms. The outcome can be either mutation of a specific site through mutagenic nonhomologous end-joining, creating insertions or deletions at the site of the break, or precise change of a genomic sequence through homologous recombination using an exogenously introduced donor template (Hendel et al., *Trends in Biotechnology* 33, 132-140 (2015)). A recent major addition to this platform is the clustered regularly interspaced palindromic repeat (CRISPR)/Cas system consisting of an RNA-guided nuclease (Cas) and a short guide RNA (gRNA) Jinek, M. et al., *Science* 337, 816-821 (2012), Mali, P. et al., *Science* 339, 823-826 (2013), Cong, L. et al., *Science* 339, 819-823 (2013), Hsu et al., *Cell* 157, 1262-1278 (2014)). The gRNA may be composed of two RNAs termed CRISPR RNA (crRNA) and trans-activating crRNA (tracrRNA), which can be fused in a chimeric single gRNA.

In many organisms, including humans and crop plants, there are a large number of diseases and traits that are modulated by multiple genetic loci. In many instances, the exact genetic locations that contribute to traits and disease phenotypes have not yet been precisely mapped out. Furthermore, for applications such as the production of recombinant proteins and chemicals for pharmaceutical or industrial use, the creation of vaccines and viral particles, and the production of fuels and nutraceuticals, it is necessary to employ genetic optimization procedures that require probing the effects of mutations at a large number of genetic loci. For the above purposes and many others, given that it is often necessary to screen at least thousands or tens of thousands of genetic loci simultaneously, the ability to perform high-throughput screening and high-content screening is critical.

Unfortunately, genome editing remains inefficient. As such, there remains a need in the art for improved compositions and methods for high-throughput genome editing and high-content screening. The present invention satisfies this need and provides additional advantages as well.

BRIEF SUMMARY OF THE INVENTION

In a first aspect, the present invention provides a retron-guide RNA cassette, the cassette comprising:

(a) a retron; and
(b) a guide RNA (gRNA) coding region.

In some embodiments, the retron comprises:
(a) an msr locus;
(b) a first inverted repeat sequence coding region;
(c) an msd locus;
(d) a donor DNA sequence located within the msd locus; and
(e) a second inverted repeat sequence coding region.

In other embodiments, the first inverted repeat sequence coding region is located within the 5' end of the msr locus. In some other embodiments, the second inverted repeat sequence is located 3' of the msd locus.

In particular embodiments, the retron encodes an RNA molecule that is capable of self-priming reverse transcription by a reverse transcriptase (RT). In some instances, reverse transcription of the RNA molecule results in a multicopy single-stranded DNA (msDNA) molecule that comprises RNA and DNA.

In some embodiments, transcription products of the retron and the gRNA coding region are physically coupled. In some embodiments, transcription products of the retron and the gRNA coding region are not physically coupled. In some embodiments, the gRNA coding region is 3' of the retron. In other embodiments, the gRNA coding region is 5' of the retron.

In other embodiments, the cassette further comprises a ribozyme sequence. In some instances, the ribozyme sequence encodes a hepatitis delta virus ribozyme.

In particular embodiments, the cassette is less than about 200 nucleotides in length. In other embodiments, the donor DNA sequence comprises two homology arms, wherein each homology arm has at least about 70% to about 99% similarity to a portion of the sequence of a genetic locus of interest on either side of a nuclease cleavage site.

In a second aspect, the present invention provides a vector comprising a retron-guide RNA cassette of the present invention.

In some embodiments, the vector further comprises a promoter that is operably linked to the cassette. In some instances, the promoter is inducible. In particular instances, the promoter is an RNA polymerase II promoter. In other instances, the promoter is an RNA polymerase III promoter. In still other instances, the vector further comprises both an RNA polymerase II promoter and an RNA polymerase III promoter.

In other embodiments, the vector further comprises a reverse transcriptase (RT) coding sequence. In yet other embodiments, the vector further comprises nuclear localizing sequence. In some instances, the nuclear localizing sequence is located 5' of the RT coding sequence.

In still other embodiments, the vector further comprises a nuclease coding sequence. In some instances, the nuclease that is encoded by the nuclease coding sequence is Cas9. In other instances, the nuclease is Cpf1. In yet other instances, both Cas9 and Cpf1 are encoded.

In a third aspect, the present invention provides a retron donor DNA-guide molecule, the molecule comprising:
(a) a retron transcript; and
(b) a guide RNA (gRNA) molecule.

In some embodiments, the retron transcript comprises:
(a) an msr region;
(b) a first inverted repeat sequence;
(c) an msd region;
(d) a donor DNA sequence coding region that is located within the msd region; and
(e) a second inverted repeat sequence.

In other embodiments, the first inverted repeat sequence is located within the 5' end of the msr region. In still other embodiments, the second inverted repeat sequence is located 3' of the msd region.

In particular embodiments, the retron transcript is capable of self-priming reverse transcription by a reverse transcriptase (RT).

In some embodiments, the retron transcript and the gRNA molecule are physically coupled. In some instances, the gRNA molecule is 3' of the retron transcript. In other instances, the gRNA molecule is 5' of the retron transcript. In some embodiments, the retron donor DNA-guide molecule further comprises a ribozyme. In some instances, the ribozyme is a hepatitis delta virus ribozyme. In some embodiments, the retron transcript and gRNA molecule are physically uncoupled after transcription.

In still other embodiments, reverse transcription of the retron transcript results in a multicopy single-stranded DNA (msDNA) molecule that comprises RNA and DNA. In some instances, at least some of the RNA content of the msDNA molecule is degraded. In certain instances, the RNA content is degraded by RNase H.

In other embodiments, the donor DNA sequence coding region comprises sequences encoding two homology arms, wherein each homology arm has at least about 70% to about 99% similarity to a portion of the sequence of a genetic locus of interest on either side of a nuclease cleavage site.

In another aspect, the present invention provides a method for modifying one or more target nucleic acids of interest at one or more target loci within a genome of a host cell, the method comprising:
  (a) transforming the host cell with a vector of the present invention; and
  (b) culturing the host cell or transformed progeny of the host cell under conditions sufficient for expressing from the vector a retron donor DNA-guide molecule comprising a retron transcript and a guide RNA (gRNA) molecule,
    wherein the retron transcript self-primes reverse transcription by a reverse transcriptase (RT) expressed by the host cell or the transformed progeny of the host cell,
    wherein at least a portion of the retron transcript is reverse transcribed to produce a multicopy single-stranded DNA (msDNA) molecule having one or more donor DNA sequences, wherein the one or more donor DNA sequences are homologous to the one or more target loci and comprise sequence modifications compared to the one or more target nucleic acids,
    wherein the one or more target loci are cut by a nuclease expressed by the host cell or transformed progeny of the host cell, wherein the site of nuclease cutting is specified by the gRNA, and
    wherein the one or more donor DNA sequences recombine with the one or more target nucleic acid sequences to insert, delete, and/or substitute one or more bases of the sequence of the one or more target nucleic acid sequences to induce one or more sequence modifications at the one or more target loci within the genome.

In some embodiments, the msr and msd regions of the retron transcript form a secondary structure, wherein the formation of the secondary structure is facilitated by base pairing between the first and second inverted repeat sequences, and wherein the secondary structure is recognized by the RT for the initiation of reverse transcription.

In other embodiments, the host cell is capable of expressing the RT prior to transforming the host cell with the vector. In some instances, the RT is encoded in a sequence integrated into the host cell genome or on a separate plasmid. In yet other embodiments, the host cell is capable of expressing the RT at the same time as, or after, transforming the host cell with the vector. In some instances, the RT is expressed from the vector or a separate plasmid.

In particular embodiments, the host cell is capable of expressing the nuclease prior to transforming the host cell with the vector. In some instances, the nuclease is encoded in a sequence integrated into the host cell genome or on a separate plasmid. In still other embodiments, the host cell is capable of expressing the nuclease at the same time as, or after, transforming the host cell with the vector. In some instances, the nuclease is expressed from the vector or a separate plasmid. In particular instances, the nuclease is Cas9. In other instances, the nuclease is Cpf1. In still other instances, both Cas9 and Cpf1 are expressed. In some embodiments, the gRNA molecule and the one or more donor DNA sequences are physically coupled. In other embodiments, the gRNA molecule and the one or more donor DNA sequences are not physically coupled.

In certain embodiments, the one or more donor DNA sequences comprise two homology arms, wherein each homology arm has at least about 70% to about 99% similarity to a portion of the sequence of the one or more target loci on either side of a nuclease cleavage site.

In some embodiments, the host cell is a prokaryotic cell. In other embodiments, the host cell is a eukaryotic cell. In some instances, the eukaryotic cell is a yeast cell.

In other embodiments, the host cell comprises a population of host cells. In some instances, the one or more sequence modifications are induced in greater than about 90% of the population of host cells. In other instances, the one or more sequence modifications are induced in greater than about 95% of the population of host cells.

In some embodiments, inducing the one or more sequence modifications results in the insertion of one or more sequences encoding cellular localization tags into the genome. In other embodiments, inducing the one or more sequence modifications results in the insertion of one or more sequences encoding degrons into the genome. In still other embodiments, inducing the one or more sequence modifications results in the insertion of one or more synthetic response elements into the genome. In particular embodiments, inducing the one or more sequence modifications results in the insertion of a combination of one or more sequences encoding cellular localization tags, one or more sequences encoding degrons, and/or one or more synthetic response elements into the genome. In yet other embodiments, inducing the one or more sequence modifications results in the insertion of one or more sequences from a heterologous genome into the genome.

In yet another aspect, the present invention provides a method for screening one or more genetic loci of interest in a genome of a host cell, the method comprising:
  (a) modifying one or more target nucleic acids of interest at one or more target loci within the genome of the host cell according to a method of the present invention;
  (b) incubating the modified host cell under conditions sufficient to elicit a phenotype that is controlled by the one or more genetic loci of interest;
  (c) identifying the resulting phenotype of the modified host cell; and
  (d) determining that the identified phenotype was the result of the modifications made to the one or more target nucleic acids of interest at the one or more target loci of interest.

In some embodiments, two or more vectors are used. In other embodiments, at least about 1,000 to 1,000,000 genetic loci of interest are screened simultaneously.

In still other embodiments, the phenotype is identified using a reporter or selectable marker. In some instances, the reporter is a fluorescent tagged protein. In other instances, the reporter is an antibody. In still other instances, the reporter is a chemical stain. In yet other instances, the reporter is a chemical indicator. In particular instances, a combination of reporters is used. In yet other instances, the reporter responds to the concentration of a metabolic product. In some instances, the reporter responds to a protein product. In some other instances, the reporter responds to a synthesized drug of interest. In still other instances, the reporter responds to a cellular phenotype of interest. In particular instances, the reporter responds to a combination of the concentration of a metabolic product, a protein product, a synthesized drug of interest, and/or a cellular phenotype of interest.

In another aspect, the present invention provides a host cell that has been transformed by a vector of the present invention.

In yet another aspect, the present invention provides a pharmaceutical composition comprising:
(a) a retron-guide RNA cassette of the present invention, a vector of the present invention, a retron donor-DNA guide molecule of the present invention, or a combination thereof; and
(b) a pharmaceutically acceptable carrier.

In still another aspect, the present invention provides a method for preventing or treating a genetic disease in a subject, the method comprising administering to the subject an effective amount of a pharmaceutical composition of the present invention to correct a mutation in a target gene associated with the genetic disease.

In some instances, the genetic disease is selected from the group consisting of X-linked severe combined immune deficiency, sickle cell anemia, thalassemia, hemophilia, neoplasia, cancer, age-related macular degeneration, schizophrenia, trinucleotide repeat disorders, fragile X syndrome, prion-related disorders, amyotrophic lateral sclerosis, drug addiction, autism, Alzheimer's disease, Parkinson's disease, cystic fibrosis, blood and coagulation diseases and disorders, inflammation, immune-related diseases and disorders, metabolic diseases and disorders, liver diseases and disorders, kidney diseases and disorders, muscular/skeletal diseases and disorders, neurological and neuronal diseases and disorders, cardiovascular diseases and disorders, pulmonary diseases and disorders, ocular diseases and disorders, and a combination thereof.

In another aspect, the present invention provides a kit for modifying one or more target nucleic acids of interest at one or more target loci within a genome of a host cell, the kit comprising one or a plurality of vectors of the present invention.

In some embodiments, the kit further comprises a host cell. In some other embodiments, the kit further comprises one or more reagents for transforming the host cell with the one or plurality of vectors, one or more reagents for inducing expression of the one or plurality of vectors, or a combination thereof.

In other embodiments, the kit further comprises a reverse transcriptase or a plasmid for expressing a reverse transcriptase. In particular embodiments, the kit further comprises a nuclease or a plasmid for expressing a nuclease.

In still other embodiments, the kit further comprises instructions for transforming the host cell, inducing expression of the vector, inducing expression of the reverse transcriptase, inducing expression of the nuclease, or a combination thereof.

In another aspect, the present invention provides a kit for modifying one or more target nucleic acids of interest at one or more target loci within a genome of a host cell, the kit comprising one or a plurality of retron donor DNA-guide molecules of the present invention.

In some embodiments, the kit further comprises a host cell. In some other embodiments, the kit further comprises one or more reagents for introducing the one or plurality of retron donor DNA-guide molecules into the host cell.

In other embodiments, the kit further comprises a reverse transcriptase or a plasmid for expressing a reverse transcriptase. In particular embodiments, the kit further comprises a nuclease or a plasmid for expressing a nuclease.

In still other embodiments, the kit further comprises instructions for introducing the one or plurality of retron donor DNA-guide molecules into the host cell, inducing expression of the reverse transcriptase, inducing expression of the nuclease, or a combination thereof.

Other objects, features, and advantages of the present invention will be apparent to one of skill in the art from the following detailed description and figures.

DETAILED DESCRIPTION OF THE INVENTION

I. Introduction

Genome editing methods commonly include the provision of both an engineered nuclease or nickase and a donor DNA repair template that contains the DNA sequence that to be inserted at a desired location. For example, the CRISPR/Cas9 system utilizes a guide RNA (gRNA) that directs the Cas9 nuclease to introduce a double-strand cut at a specific location. A donor DNA repair template can then be provided, enabling the precise insertion of a new sequence mediated by homology-directed repair of the double-strand cut. In the past, the gRNA and donor DNA template have been supplied as separate molecules, meaning that each editing experiment must be performed in a separate tube or vessel. Efforts to increase editing efficiency by delivering gRNA and donor DNA sequences jointly to cells in a pooled system have thus far been unsuccessful.

Figure 1:
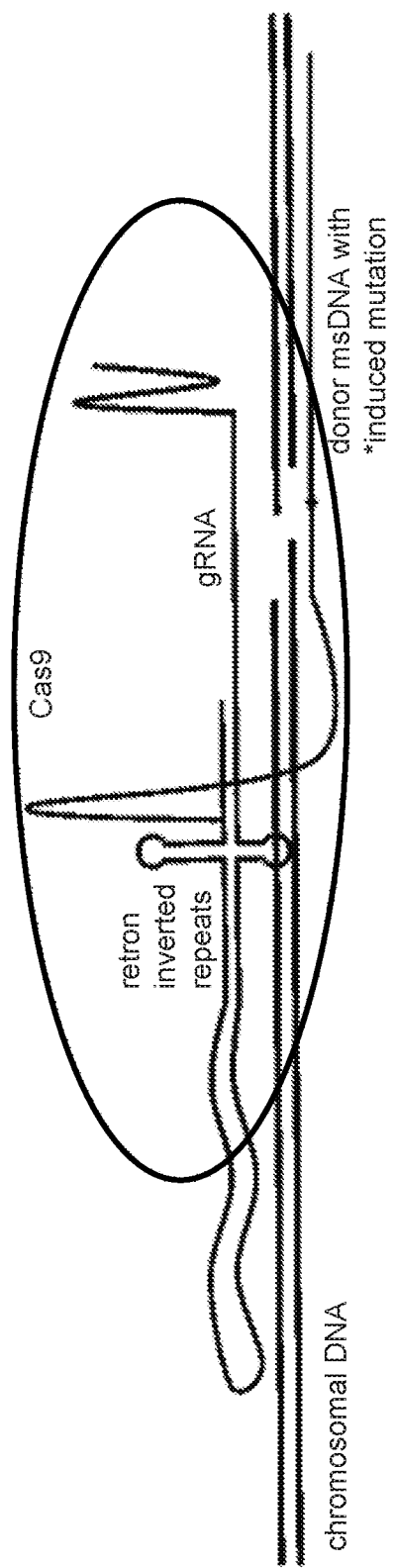
FIG. 1 shows an example of the genome editing methods of the present invention. In this example, a guide RNA (gRNA) molecule has been used to direct a Cas9 nuclease to make a double-strand DNA cut at a desired genomic location. The gRNA and a retron transcript that contains inverted repeat sequences are physically joined and have previously been transcribed from a retron-guide RNA cassette. Following transcription, the msd region of the retron transcript was reverse transcribed, resulting in a multicopy single-strand DNA molecule, physically coupled to the gRNA, and containing a donor DNA sequence (denoted with asterisk) that will be incorporated into the desired genomic site when the double-strand cut is repaired.

The present invention is based, in part, on the surprising discovery that physically coupling a gRNA molecule to the transcript product of an obscure bacterial genetic element termed a retron dramatically increases the efficiency of DNA editing and screening. In particular, the reverse transcription of the DNA coding unit (msd region) of the retron transcript results in a multicopy single-stranded DNA (msDNA) molecule that contains a donor DNA repair template and is physically tethered to the gRNA, increasing editing efficiency. As shown as an example in FIG. 1, once the gRNA directs the Cas9 nuclease to the desired genomic location and Cas9 completes the double-strand cut of the genomic DNA, the donor repair template within the msDNA molecule is already nearby and facilitates the genomic DNA repair and edit.

II. General

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, *Molecular Cloning: A Laboratory Manual,* 2nd edition (1989), *Current Protocols in Molecular Biology* (F. M. Ausubel, et al. eds., (1987)), the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual,* and *Animal Cell Culture* (R. I. Freshney, ed. (1987)).

For nucleic acids, sizes are given in either kilobases (kb), base pairs (bp), or nucleotides (nt). Sizes of single-stranded DNA and/or RNA can be given in nucleotides. These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

III. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

Figure 4:
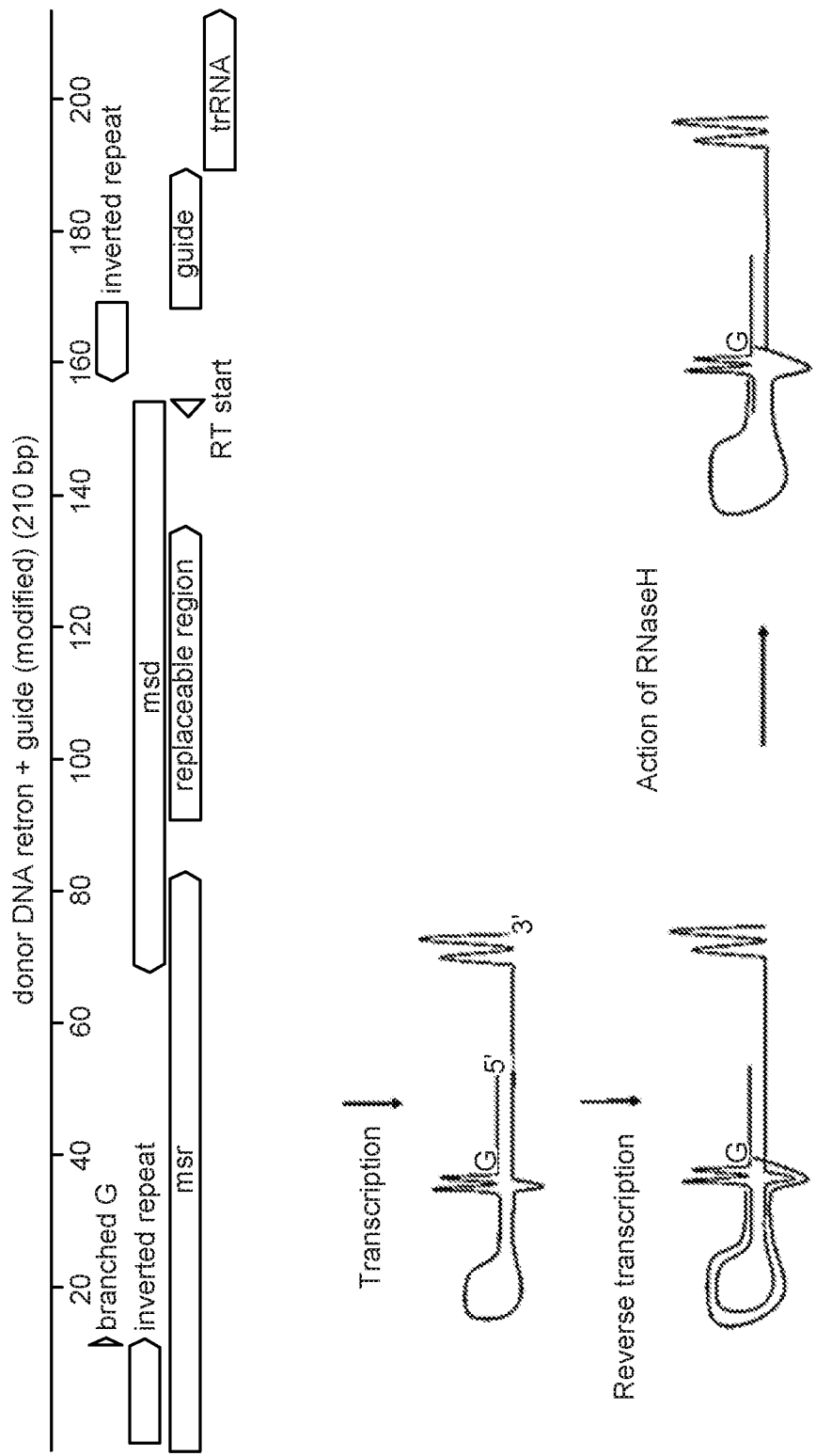
FIG. 4 depicts an example of the biogenesis of a retron donor DNA-guide molecule of the present invention. A retron-guide RNA cassette of the present invention is transcribed, yielding a retron donor DNA-guide molecule. The retron transcript portion of the molecule folds and adopts specific secondary structure, facilitated by pairing between the first and second inverted sequence repeats, and folds with specific secondary structure. The bacterial reverse transcriptase recognizes the secondary structure of the msr-msd regions of the retron transcript and generates msDNA covalently attached to a branched G near the 5' end of the molecule. Also depicted in this example is RNase H acting on the RNA-DNA duplex, removing some of the internal RNA.

As used herein, unless otherwise specified, the terms "5'" and "3'" denote the positions of elements or features relative to the overall arrangement of the retron-guide RNA cassettes, vectors, or retron donor DNA-guide molecules of the present invention in which they are included. Positions are not, unless otherwise specified, referred to in the context of the orientation of a particular element or features. For example, the msr and msd loci in FIG. 4 are shown in opposite orientations. However, the msr locus is said to be 5' of the msd locus. Furthermore, the 3' end of the msr locus is said to be overlapping with the 5' end of the msd locus. Unless otherwise specified, the term "upstream" refers to a position that is 5' of a point of reference. Conversely, the term "downstream" refers to a position that is 3' of a point of reference. Thus, in FIG. 2 the msr locus is said to be located upstream of the reverse transcriptase sequence, and the reverse transcriptase sequence is said to be located downstream of the msr locus.

The term "genome editing" refers to a type of genetic engineering in which DNA is inserted, replaced, or removed from a target DNA (e.g., the genome of a cell) using one or more nucleases and/or nickases. The nucleases create specific double-strand breaks (DSBs) at desired locations in the genome, and harness the cell's endogenous mechanisms to repair the induced break by homology-directed repair (HDR) (e.g., homologous recombination) or by nonhomologous end joining (NHEJ). The nickases create specific single-strand breaks at desired locations in the genome. In one non-limiting example, two nickases can be used to create two single-strand breaks on opposite strands of a target DNA, thereby generating a blunt or a sticky end. Any suitable DNA nuclease can be introduced into a cell to induce genome editing of a target DNA sequence.

The term "DNA nuclease" refers to an enzyme capable of cleaving the phosphodiester bonds between the nucleotide subunits of DNA, and may be an endonuclease or an exonuclease. According to the present invention, the DNA nuclease may be an engineered (e.g., programmable or targetable) DNA nuclease which can be used to induce genome editing of a target DNA sequence. Any suitable DNA nuclease can be used including, but not limited to, CRISPR-associated protein (Cas) nucleases, other endo- or exo-nucleases, variants thereof, fragments thereof, and combinations thereof.

The term "double-strand break" or "double-strand cut" refers to the severing or cleavage of both strands of the DNA double helix. The DSB may result in cleavage of both stands at the same position leading to "blunt ends" or staggered cleavage resulting in a region of single-stranded DNA at the end of each DNA fragment, or "sticky ends". A DSB may arise from the action of one or more DNA nucleases.

The term "nonhomologous end joining" or "NHEJ" refers to a pathway that repairs double-strand DNA breaks in which the break ends are directly ligated without the need for a homologous template.

The term "homology-directed repair" or "HDR" refers to a mechanism in cells to accurately and precisely repair double-strand DNA breaks using a homologous template to guide repair. The most common form of HDR is homologous recombination (HR), a type of genetic recombination in which nucleotide sequences are exchanged between two similar or identical molecules of DNA.

The term "nucleic acid," "nucleotide," or "polynucleotide" refers to deoxyribonucleic acids (DNA), ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. In some embodiments, a nucleic acid can comprise a mixture of DNA, RNA and analogs thereof. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The term "single nucleotide polymorphism" or "SNP" refers to a change of a single nucleotide within a polynucleotide, including within an allele. This can include the replacement of one nucleotide by another, as well as the deletion or insertion of a single nucleotide. Most typically, SNPs are biallelic markers although tri- and tetra-allelic markers can also exist. By way of non-limiting example, a nucleic acid molecule comprising SNP A\C may include a C or A at the polymorphic position.

The term "gene" means the segment of DNA involved in producing a polypeptide chain. The DNA segment may include regions preceding and following the coding region (leader and trailer) involved in the transcription/translation of the gene product and the regulation of the transcription/translation, as well as intervening sequences (introns) between individual coding segments (exons).

The term "cassette" refers to a combination of genetic sequence elements that may be introduced as a single element and may function together to achieve a desired result. A cassette typically comprises polynucleotides in combinations that are not found in nature.

The term "operably linked" refers to two or more genetic elements, such as a polynucleotide coding sequence and a promoter, placed in relative positions that permit the proper biological functioning of the elements, such as the promoter directing transcription of the coding sequence.

The term "inducible promoter" refers to a promoter that responds to environmental factors and/or external stimuli that can be artificially controlled in order to modify the expression of, or the level of expression of, a polynucleotide sequence or refers to a combination of elements, for example an exogenous promoter and an additional element such as a trans-activator operably linked to a separate promoter. An inducible promoter may respond to abiotic factors such as oxygen levels or to chemical or biological molecules. In some embodiments, the chemical or biological molecules may be molecules not naturally present in humans.

The terms "vector" and "expression vector" refer to a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. The term "promoter" is used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Other elements that may be present in an expression vector include those that enhance transcription (e.g., enhancers) and terminate transcription (e.g., terminators).

"Recombinant" refers to a genetically modified polynucleotide, polypeptide, cell, tissue, or organism. For example, a recombinant polynucleotide (or a copy or complement of a recombinant polynucleotide) is one that has been manipulated using well known methods. A recombinant expression cassette comprising a promoter operably linked to a second polynucleotide (e.g., a coding sequence) can include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, New York, (1989) or Current Protocols in Molecular Biology Volumes 1-3, John Wiley & Sons, Inc. (1994-1998)). A recombinant expression cassette (or expression vector) typically comprises polynucleotides in combinations that are not found in nature. For instance, human manipulated restriction sites or plasmid vector sequences can flank or separate the promoter from other sequences. A recombinant protein is one that is expressed from a recombinant polynucleotide, and recombinant cells, tissues, and organisms are those that comprise recombinant sequences (polynucleotide and/or polypeptide).

As used herein, the term "heterologous" refers to biological material that is introduced, inserted, or incorporated into a recipient (e.g., host) organism that originates from another organism. Typically, the heterologous material that is introduced into the recipient organism (e.g., a host cell) is not normally found in that organism. Heterologous material can include, but is not limited to, nucleic acids, amino acids, peptides, proteins, and structural elements such as genes, promoters, and cassettes. A host cell can be, but is not limited to, a bacterium, a yeast cell, a mammalian cell, or a plant cell. The introduction of heterologous material into a host cell or organism can result, in some instances, in the expression of additional heterologous material in or by the host cell or organism. As a non-limiting example, the transformation of a yeast host cell with an expression vector that contains DNA sequences encoding a bacterial protein may result in the expression of the bacterial protein by the yeast cell. The incorporation of heterologous material may be permanent or transient. Also, the expression of heterologous material may be permanent or transient.

The terms "reporter" and "selectable marker" can be used interchangeably and refer to a gene product that permits a cell expressing that gene product to be identified and/or isolated from a mixed population of cells. Such isolation might be achieved through the selective killing of cells not expressing the selectable marker, which may be, as a non-limiting example, an antibiotic resistance gene. Alternatively, the selectable marker may permit identification and/or subsequent isolation of cells expressing the marker as a result of the expression of a fluorescent protein such as GFP or the expression of a cell surface marker which permits isolation of cells by fluorescence-activated cell sorting (FACS), magnetic-activated cell sorting (MACS), or analogous methods. Suitable cell surface markers include CD8, CD19, and truncated CD19. Preferably, cell surface markers used for isolating desired cells are non-signaling molecules, such as subunit or truncated forms of CD8, CD19, or CD20. Suitable markers and techniques are known in the art.

The terms "culture," "culturing," "grow," "growing," "maintain," "maintaining," "expand," "expanding," etc., when referring to cell culture itself or the process of culturing, can be used interchangeably to mean that a cell (e.g., yeast cell) is maintained outside its normal environment under controlled conditions, e.g., under conditions suitable for survival. Cultured cells are allowed to survive, and culturing can result in cell growth, stasis, differentiation or division. The term does not imply that all cells in the culture survive, grow, or divide, as some may naturally die or senesce. Cells are typically cultured in media, which can be changed during the course of the culture.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

As used herein, the term "administering" includes oral administration, topical contact, administration as a suppository, intravenous, intraperitoneal, intramuscular, intralesional, intrathecal, intranasal, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The term "treating" refers to an approach for obtaining beneficial or desired results including, but not limited to, a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "sufficient amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific amount may vary depending on one or more of: the particular agent chosen, the host cell type, the location of the host cell in the subject, the dosing regimen to be followed, whether it is administered in combination with other compounds, timing of administration, and the physical delivery system in which it is carried.

The term "pharmaceutically acceptable carrier" refers to a substance that aids the administration of an active agent to a cell, an organism, or a subject. "Pharmaceutically acceptable carrier" refers to a carrier or excipient that can be included in the compositions of the invention and that causes no significant adverse toxicological effect on the patient. Non-limiting examples of pharmaceutically acceptable carrier include water, NaCl, normal saline solutions, lactated Ringer's, normal sucrose, normal glucose, cell culture media, and the like. One of skill in the art will recognize that other pharmaceutical carriers are useful in the present invention.

The term "degron" refers to a region or portion of a protein that regulates the rate of protein degradation. Degrons can be located anywhere in a protein, and can include short amino acid sequences, structural motifs, or exposed amino acids (e.g., lysine, arginine). Degrons exist in both prokaryotic and eukaryotic organisms. Degrons can be classified as being either ubiquitin-dependent or ubiquitin-independent. For additional information regarding degrons, see, e.g., Raid, et al. *Nat. Rev. Mol. Cell Biol.* 9:679-690 (2008); incorporated herein by reference in its entirety for all purposes.

The term "cellular localization tag" refers to an amino acid sequence, also known as a "protein localization signal," that targets a protein for localization to a specific cellular or subcellular region, compartment, or organelle (e.g., nuclear localization sequence, Golgi retention signal). Cellular localization tags are typically located at either the N-terminal or C-terminal end of a protein. A database of protein localization signals (LocSigDB) is maintained online by the University of Nebraska Medical Center (genome.unmc.edu/LocSigDB). For more information regarding cellular localization tags, see, e.g., Negi, et al. *Database (Oxford)*. 2015: bav003 (2015); incorporated herein by reference in its entirety for all purposes.

The term "synthetic response element" refers to a recombinant DNA sequence that is recognized by a transcription factor and facilitates gene regulation by various regulatory agents. A synthetic response element can be located within a gene promoter and/or enhancer region.

The term "ribozyme" refers to an RNA molecule that is capable of catalyzing a biochemical reaction. In some instances, ribozymes function in protein synthesis, catalyzing the linking of amino acids in the ribosome. In other instances, ribozymes participate in various other RNA processing functions, such as splicing, viral replication, and tRNA biosynthesis. In some instances, ribozymes can be self-cleaving. Non-limiting examples of ribozymes include the HDV ribozyme, the Lariat capping ribozyme (formally called GIR1 branching ribozyme), the glmS ribozyme, group I and group II self-splicing introns, the hairpin ribozyme, the hammerhead ribozyme, various rRNA molecules, RNase P, the twister ribozyme, the VS ribozyme, the pistol ribozyme, and the hatchet ribozyme. For more information regarding ribozymes, see, e.g., Doherty, et al. *Ann. Rev. Biophys. Biomol. Struct.* 30: 457-475 (2001); incorporated herein by reference in its entirety for all purposes.

"Percent similarity," in the context of polynucleotide or peptide sequences, is determined by comparing two optimally aligned sequences over a comparison window, wherein the portion of the sequence (e.g., an msr locus sequence) in the comparison window may comprise additions or deletions (i.e., gaps) as compared to the reference sequence which does not comprise additions or deletions, for optimal alignment of the two sequences. The percentage is calculated by determining the number of positions at which the identical nucleotide or amino acid occurs in both sequences to yield the number of matched positions, dividing the number of matched positions by the total number of positions in the window of comparison and multiplying the result by 100 to yield the percentage of similarity (e.g., sequence similarity).

When a polynucleotide or peptide has at least about 70% similarity (e.g., sequence similarity), preferably at least about 85%, 86%, 87%, 88%, 89%, 90%, 91%, 92%, 93, 94%, 95%, 96%, 97%, 98%, 99%, or 100% similarity, to a reference sequence, when compared and aligned for maximum correspondence over a comparison window, or designated region as measured using one of the following sequence comparison algorithms or by manual alignment and visual inspection, such sequences are then said to be "substantially similar." With regard to polynucleotide sequences, this definition also refers to the complement of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence similarities for the test sequences relative to the reference sequence, based on the program parameters. For sequence comparison of nucleic acids and proteins, the BLAST and BLAST 2.0 algorithms and the default parameters discussed below are used.

Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

Additional examples of algorithms that are suitable for determining percent sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see, e.g., Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA,* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

IV. Detailed Description of the Embodiments

The present invention provides compositions and methods for high-throughput genome editing and screening. The invention provides methods comprising the use of retron-guide RNA cassettes, vectors comprising said cassettes, and retron donor DNA-guide molecules of the present invention to modify nucleic acids of interest at target loci of interest, and to screen genetic loci of interest, in the genomes of host cells. The present invention also provides compositions and methods for preventing or treating genetic diseases by enhancing precise genome editing to correct a mutation in target genes associated with the diseases. Kits for genome editing and screening are also provided. The present invention can be used with any cell type and at any gene locus that is amenable to nuclease-mediated genome editing technology.

A. The CRISPR-Retron System

In a first aspect, the present invention provides a retron-guide RNA (gRNA) cassette. In some embodiments, the cassette comprises:
 (a) a retron; and
 (b) a guide RNA (gRNA) coding region.
In some embodiments, the retron comprises:
 (a) an msr locus;
 (b) a first inverted repeat sequence coding region;
 (c) an msd locus;
 (d) a donor DNA sequence located within the msd locus; and
 (e) a second inverted repeat sequence coding region.

In some embodiments, transcription products of the retron and the gRNA coding region are physically coupled. In particular embodiments, the resulting gRNA and donor DNA sequences are also physically coupled (e.g., during genome editing and/or screening). In some embodiments, the transcription products are coupled during a single transcription event. In particular embodiments, the transcription products of the retron and the gRNA coding region are initially coupled, and then subsequently become uncoupled (e.g., after transcription of the retron, or after reverse transcription of the retron transcript), in which case the guide RNA and the donor DNA sequence will also be physically uncoupled during genome editing and/or screening. In some instances, uncoupling can be induced by a ribozyme. A non-limiting example of a suitable ribozyme is the hepatitis delta virus (HDV) ribozyme. In some embodiments, the cassette further comprises a ribozyme sequence (e.g., HDV ribozyme sequence). An exemplary HDV ribozyme sequence is set forth in SEQ ID NO:29

In some embodiments, transcription products of the retron and the gRNA coding region are not initially physically coupled (i.e., the transcription products are created in separate transcription events). As a non-limiting example, the retron and the gRNA coding region can be included in two different retron-gRNA cassettes, which can be included in the same vector or in different vectors. In some embodiments, expression from the vector(s) occurs inside a host cell. In other embodiments, transcription of the retron and/or the gRNA coding region occurs outside of the host cell, and then the transcription product(s) are introduced into the host cell. In some embodiments, the transcription products are created in separate transcription events and are subsequently joined together for genome editing and/or screening, in which case the resulting gRNA and donor DNA sequence will also be physically coupled for genome editing and/or screening. Such joining can occur before or after reverse transcription of the retron transcript (i.e., before or after creation of msDNA from the retron transcript). In some embodiments, the transcription products of the retron and the gRNA coding region result in a donor DNA sequence and a gRNA that are never physically coupled. In some instances the retron and the gRNA coding region are located in different cassettes and the resulting donor DNA sequence and gRNA act in trans.

In some embodiments, the gRNA coding region of the cassette is located 3' of the retron. In other embodiments, the gRNA coding region is located 5' of the retron. The relative positions of the gRNA coding region and retron may be selected, for example, based upon the particular nuclease being used.

In some embodiments, the retron-gRNA cassette is at least about 5,000 nucleotides in length. In other embodiments, the retron-gRNA cassette is between about 1,000 and 5,000 (i.e., about 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, or 5,000) nucleotides in length. In some other embodiments, the cassette is between about 300 and 1,000 (i.e., about 300, 350, 400, 450, 500, 550, 600, 650, 700, 750, 800, 850, 900, 950, or 1,000) nucleotides in length. In particular embodiments, the cassette is between about 200 and 300 (i.e., about 200, 210, 220, 230, 240, 250, 260, 270, 280, 290, or 300) nucleotides in length. In other embodiments, the cassette is between about 30 and 200 (i.e., about 30, 40, 50, 60, 70, 80, 90, 100, 110, 120, 130, 140, 150, 160, 170, 180, 190, or 200) nucleotides in length. In some embodiments, the cassette is about 200 (i.e., between about 100 and 300, 150 and 250, 175 and 225, or 190 and 210) nucleotides in length.

In other embodiments, the cassette further comprises one or more sequences having homology to a vector cloning site. These vector homology sequences can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, or more nucleotides in length. In some instances, the vector homology sequences are about 20 nucleotides in length. In other instances, the vector homology sequence are about 15 nucleotides in length. In yet other instances, the vector homology sequences are about 25 nucleotides in length.

In a second aspect, the present invention provides a vector comprising a retron-guide RNA cassette of the present invention. In some embodiments, the vector further comprises a promoter. Preferably, the promoter is operably linked to the cassette. In particular embodiments, the promoter is inducible. In some instances, the promoter is an RNA polymerase II promoter. In other instances, the promoter is an RNA polymerase III promoter. In particular instances, a combination of promoters is used. In some other embodiments, the vector further comprises a terminator sequence. Vectors of the present invention can include commercially available recombinant expression vectors and fragments and variants thereof. Examples of suitable promoters and recombinant expression vectors are described herein and will also be known to one of skill in the art.

Vectors of the present invention may further comprise a reverse transcriptase (RT) coding sequence and, optionally, may further comprise a nuclear localization sequence (NLS). In some instances, the NLS will be located 5' of the RT coding sequence.

Vectors of the present invention can further comprise a nuclease coding sequence. The sequence can encode Cas9, Cpf1, or any other suitable nuclease. Examples of suitable nucleases are provided herein and will also be known to one of skill in the art.

When the vector includes an RT coding sequence and/or a nuclease coding sequence, expression of the retron-gRNA cassette and the RT coding sequence and/or the nuclease coding sequence can all be under the control of a single promoter. Alternatively, expression of the retron-gRNA cassette and the RT coding sequence and/or the nuclease coding sequence can each be under the control of a different promoter. Other combinations are also possible. As a non-limiting example, expression of the retron-gRNA cassette can be under the control of one promoter, while expression of the RT coding sequence and/or the nuclease coding sequence are under the control of another promoter. As another non-limiting example, expression of the retron-gRNA cassette and expression of the RT coding sequence can be under the control of one promoter, while expression of the nuclease coding sequence can be under the control of another promoter. As yet another non-limiting example, expression of the retron-gRNA cassette and expression of the nuclease coding sequence can be under the control of one promoter, while the RT coding sequence is under the control of another promoter. In particular embodiments, one or more of the promoters are inducible. As a non-limiting example, the vector can comprise a retron-gRNA cassette under the control of a Gal7 promoter, an RT coding sequence under the control of a Gal10 promoter, and a nuclease (e.g., Cas9) coding sequence under the control of a Gal1 promoter. Non-limiting examples of other suitable promoters are described herein. In other embodiments, the vector contains a reporter unit that includes a nucleotide sequence encoding a reporter polypeptide (e.g., a detectable polypeptide, fluorescent polypeptide, or a selectable marker (e.g., URA3)).

The size of the vector will depend on the size of the individual components within the vector, e.g., retron-gRNA cassette, RT coding sequence, nuclease coding sequence, NLS, and so on. In some embodiments, the vector is less than about 1,000 (i.e., less than about 1,000, 950, 900, 850, 800, 750, 700, 650, 600, 550, or 500) nucleotides in length. In other embodiments, the vector is between about 1,000 and about 20,000 (i.e., about 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, or 20,000) nucleotides in length. In particular embodiments, the vector is more than about 20,000 nucleotides in length.

In a third aspect, the present invention provides a retron donor DNA-guide molecule. In some embodiments, the retron donor DNA-guide molecule comprises:
    (a) a retron transcript; and
    (b) a guide RNA (gRNA) molecule.
In some embodiments, the retron transcript comprises:
    (a) an msr region;
    (b) a first inverted repeat sequence;
    (c) an msd region;
    (d) a donor DNA sequence coding region that is located within the msd region; and
    (e) a second inverted repeat sequence.

Figure 5:
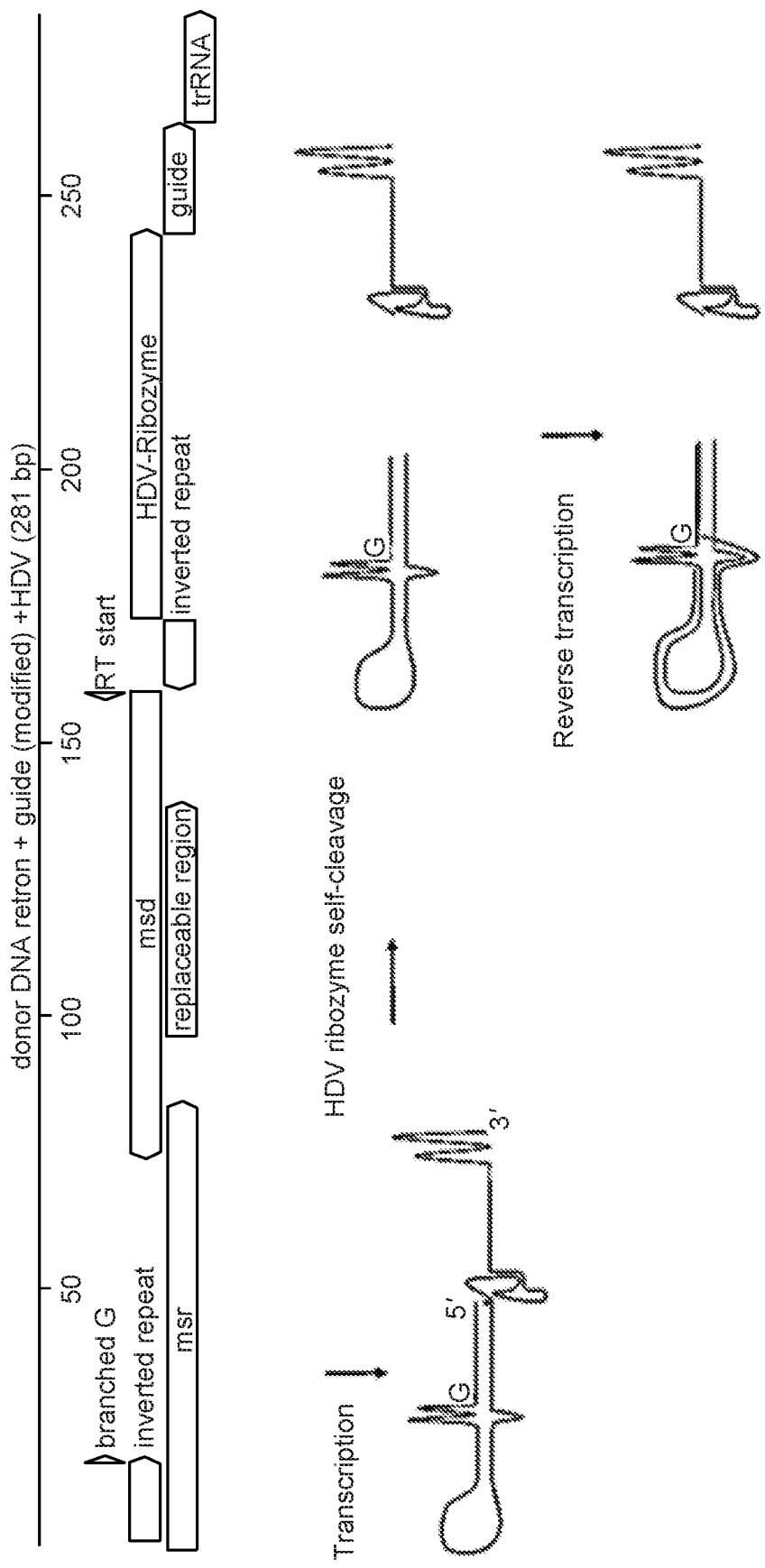
FIG. 5 shows the separation of multicopy single-stranded DNA (msDNA) from the guide RNA (gRNA) with the use of a hepatitis delta virus (HDV) self-cleaving ribozyme. In this construct, the HDV ribozyme sequence was inserted immediately 5' of the gRNA coding region. Following transcription, the HDV ribozyme folds into a secondary structure that forces autocatalytic cleavage of the transcript product immediately 5' of the HDV, separating the retron transcript from the gRNA. Subsequently, the bacterial reverse transcriptase generates msDNA from the retron transcript, while the gRNA independently assembles with the nuclease Cas9 to direct genome cutting.

In some embodiments, the retron transcript and the gRNA molecule are physically coupled. In particular embodiments, the resulting donor DNA sequence and gRNA are also physically coupled (e.g., during genome editing and/or screening). In some embodiments, the retron transcript and gRNA are coupled during a single transcription event. In particular embodiments, the retron transcript and gRNA are initially coupled, and then subsequently become uncoupled (e.g., after transcription, or after reverse transcription of the retron transcript), in which case the donor DNA sequence and the gRNA will also be physically uncoupled during genome editing and/or screening. In some instances, uncoupling can be induced by a ribozyme. A non-limiting example of a suitable ribozyme is a hepatitis delta virus (HDV) ribozyme. In some embodiments, the retron donor DNA-guide molecule further comprises a ribozyme (e.g., HDV ribozyme). A non-limiting example of this arrangement is shown in FIG. 5. In some embodiments, the retron donor DNA-guide molecule produces a gRNA and a donor DNA sequence that are never physically coupled.

Figure 3:
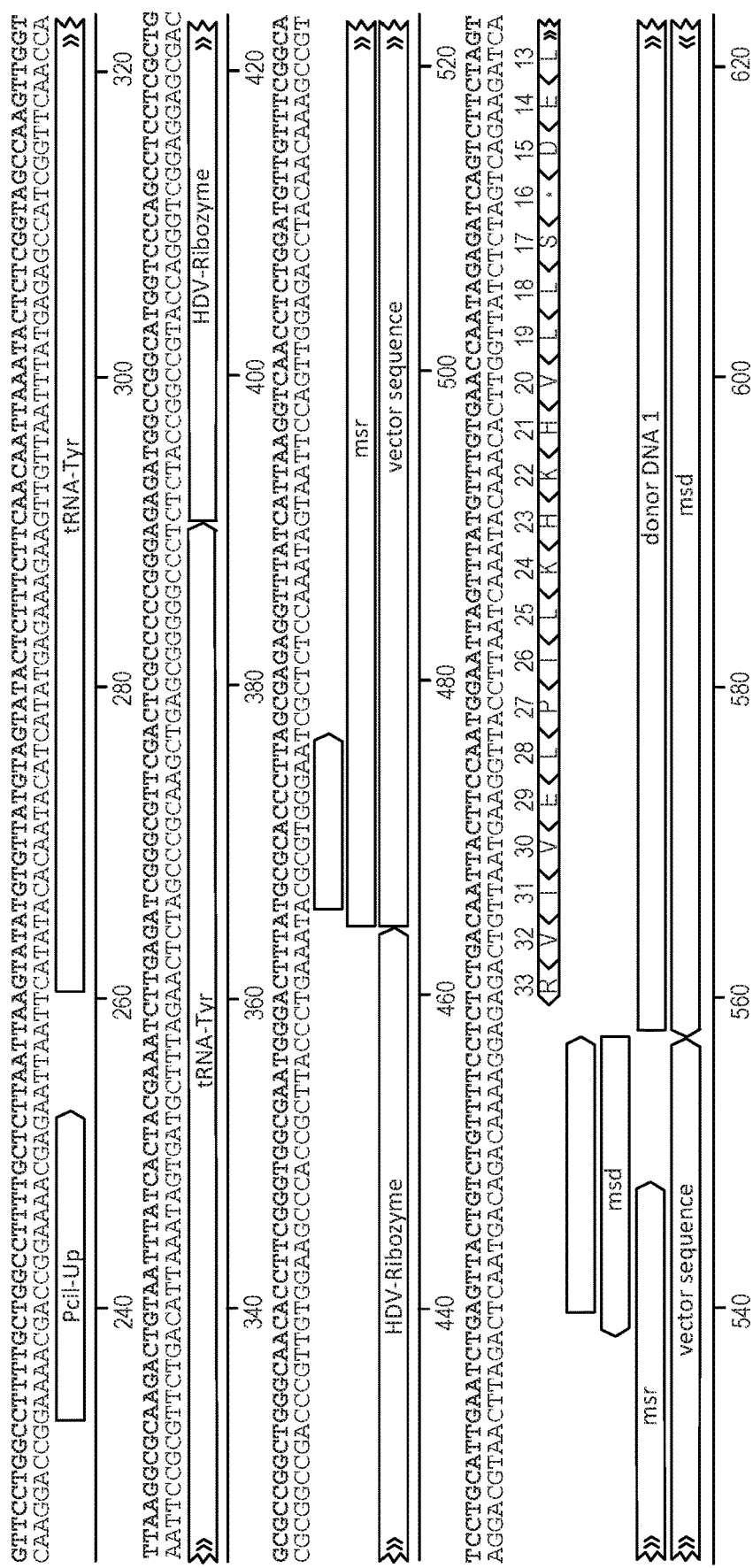
FIG. 3 shows an example of a precision editing retron-guide RNA cassette. In this example, the donor DNA sequence contains a nonsense mutation to the ADE1 gene that has been inserted in the center of the msd locus of the retron. The guide RNA has been placed directly 3' of the second inverted repeat. In this example, the cassette is under the control of a tRNA-Tyr promoter. The full sequence of the cassette is set forth in SEQ ID NO:24. Start (i.e., 5' of Pci1-Up) and end (i.e., 3' of the RPR1 terminator) sequences are set forth in SEQ ID NOS:25 and 39, respectively. The inverted repeat sequence is set forth in SEQ ID NO:16. A Pci1-Up primer binding sequence (used for cloning and sequencing) is set forth in SEQ ID NO:26. The sequence between Pci1-Up and tRNA-Tyr is set forth in SEQ ID NO:27. tRNA-Tyr and HDV ribozyme sequences are set forth in SEQ ID NOS:28 and 29, respectively. The sequences of the msr and msd loci are set forth in SEQ ID NOS:18 and 30, respectively (the sequence of the portion of the msd that overlaps the vector, but does not include the donor, is set forth in SEQ ID NO:31). Vector sequence is set forth in SEQ ID NO:32. Donor DNA1 sequence is set forth in SEQ ID NO:33. Constant synthesis sequence is set forth in SEQ ID NO:34. The guide2 sequence and the sgRNA coding sequence are set forth in SEQ ID NOS:35 and 36, respectively. SNR52 and RPT1 terminator sequences are set forth in SEQ ID NOS:37 and 38, respectively. All sequences are shown directly above their complementary sequences. Also shown are amino acid sequences on either side of the edit site within ADE1. From N-terminal to C-terminal, these sequences are PAKLSEPKYKTQLED (SEQ ID NO:40; labeled as amino acids 1-15) and SLLVHKHKLIPLEVIVR (SEQ ID NO:41; labeled as amino acids 17-33). The edit site (labeled as amino acid number 16) is denoted with an asterisk.
Figure 3:
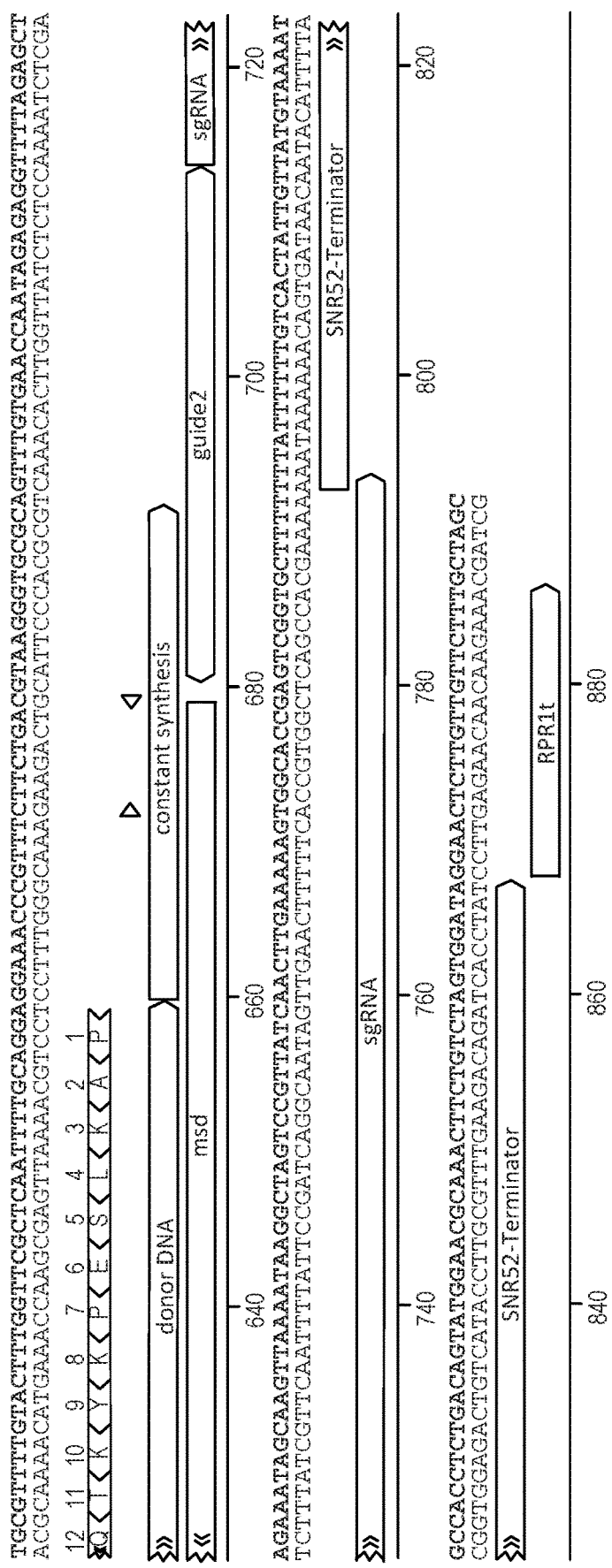

One or more ribozymes can be used to process or modify the retron donor DNA-guide molecule. As a non-limiting example, following transcription under the control of an RNA polymerase II promoter, a ribozyme (e.g., HDV ribozyme) can be used to cleave the 5' cap and 3' polyadenylation signal following export of the retron donor DNA-guide molecule to the cytoplasm. The example of a retron-guide RNA cassette shown in FIG. 3 illustrates the placement of an HDV ribozyme for the purpose of post-transcription processing.

In some embodiments, the retron transcript and the gRNA are created in separate transcription events and are subsequently joined together. Whether the retron transcript and the gRNA are created in one transcription event or different transcription events, transcription can occur inside a cell (e.g., inside a host cell comprising one or more cassettes or one or more vectors of the present invention), or outside of a host cell (i.e., in which case the retron transcript and the gRNA are introduced into the host cell).

In some embodiments, the gRNA molecule is located 3' of the retron transcript. In other embodiments, the gRNA molecule is located 5' of the retron transcript. The relative positions of the gRNA and retron transcript may be selected, for example, based upon the particular nuclease being used.

Also provided in the present invention are molecules further comprising a multicopy single-stranded DNA (msDNA) molecule comprising RNA and DNA (e.g., following reverse transcription of the retron transcript, resulting in a branched hybrid RNA-DNA molecule). In some embodiments, the donor DNA sequence is physically coupled to the gRNA, by virtue of the msDNA being physically coupled to the gRNA. In some instances, at least some of the RNA content of the msDNA is degraded (e.g., by an RNase such as RNase H). In some embodiments, the donor DNA sequence and the gRNA are initially coupled, and then are subsequently uncoupled (e.g., by cleavage of the msDNA from the gRNA). In some embodiments, the donor DNA sequence and the gRNA are never physically coupled.

1. Retrons

Figure 2:
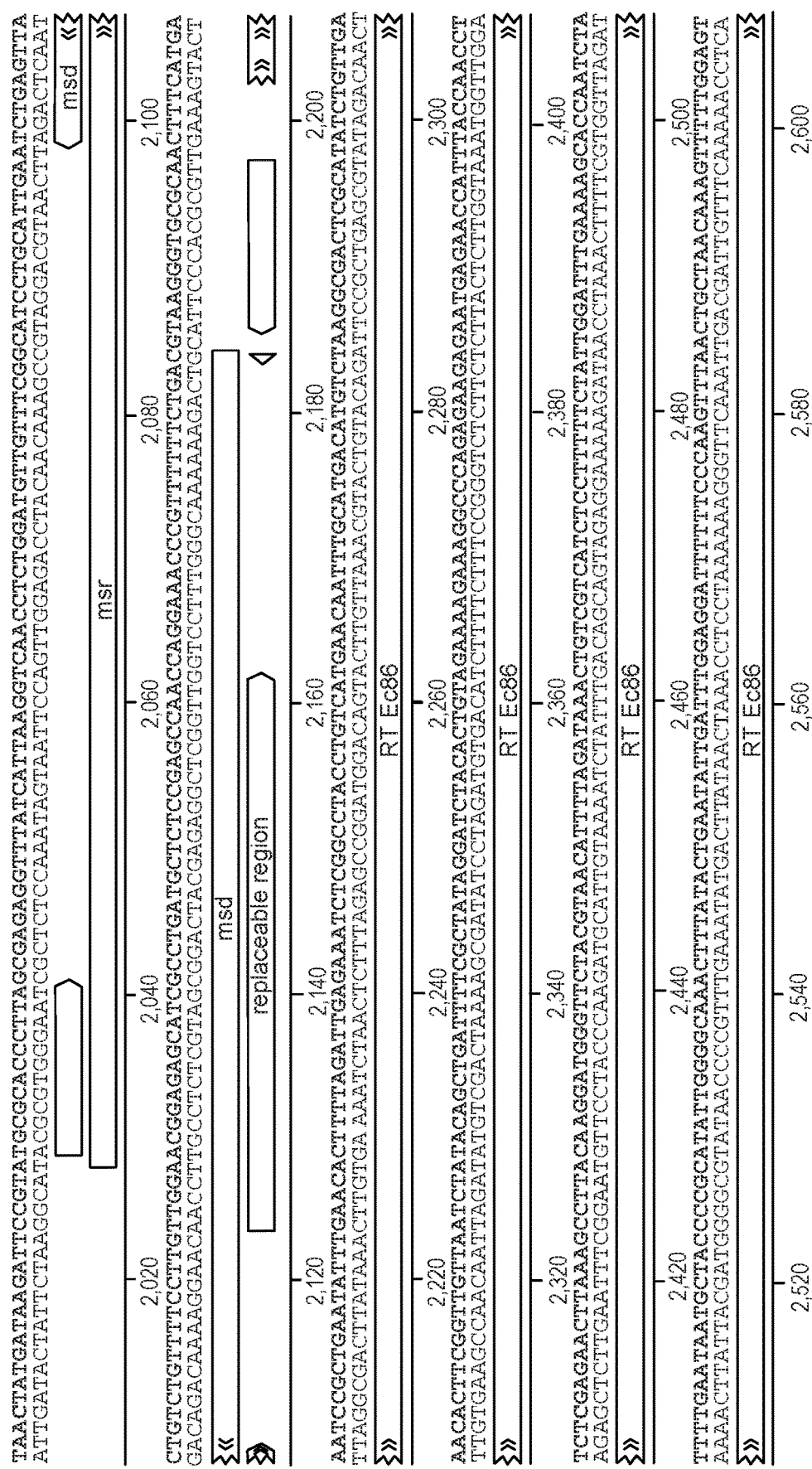
FIG. 2 shows the wild type *E. coli* retron Ec86, which was inserted into a plasmid. In *E. coli*, retrons exist as a single compact unit with the msr and msd loci directly adjacent to an RT and are transcribed as a single polycistronic transcript. The RT, once translated, reverse transcribes the msd locus to produce multicopy single-stranded DNA (msDNA). Inverted repeat sequences are located within the 5' end of the msr locus and just 3' to the msd locus. The full sequence of the retron is set forth in SEQ ID NO:14. Plasmid sequence located 5' of the msr locus is set forth in SEQ ID NO:15. The first and second inverted repeat sequences are set forth in SEQ ID NOS:16 and 17, respectively. The sequences of the msr and msd loci are set forth in SEQ ID NOS:18 and 19, respectively. A "G" nucleotide is present between the msd locus and the second inverted repeat sequence. The replaceable region sequence is set forth in SEQ ID NO:20. The optimized reverse transcriptase (RT) sequence is set forth in SEQ ID NO:21. A short sequence (i.e., ACTTTC; SEQ ID NO:22) is located between the second inverted repeat sequence and the beginning of the RT sequence. The sequence located 3' of the RT sequence is set forth in SEQ ID NO:23. All sequences are shown directly above their complementary sequences.

Retrons have been known for some time as a class of retroelement, first discovered in gram-negative bacteria such as *Myxococcus xanthus* (e.g., retrons Mx65 and Mx162), *Stigmatella aurantiaca* (e.g., retron Sa163), and *Escherichia coli* (e.g., retrons Ec48, Ec67, Ec73, Ec78, Ec83, Ec86, and Ec107). Retrons are also found in *Salmonella typhimurium* (e.g., retron St85), *Salmonella enteritidis*, *Vibrio cholera* (e.g., retron Vc95), *Vibrio parahaemolyticus* (e.g., retron Vp96), *Klebsiella pneumoniae*, *Proteus mirabilis*, *Xanthomonas campestris*, *Rhizobium* sp., *Bradyrhizobium* sp., *Ralstonia metallidurans*, *Nannocystis exedens* (e.g., retron Ne144), *Geobacter sulfurreducens*, *Trichodesmium erythraeum*, *Nostoc punctiforme*, *Nostoc* sp., *Staphylococcus aureus*, *Fusobacterium nucleatum*, and *Flexibacter elegans*. In one aspect, the present invention provides for retron-guide RNA cassettes that comprise a retron. In some embodiments, the retron is derived from the *E. coli* retron Ec86, which is shown in FIG. 2.

Retrons mediate the synthesis in host cells of multicopy single-stranded DNA (msDNA) molecules, which result from the reverse transcription of a retron transcript and typically include a DNA component and an RNA component. The native msDNA molecules reportedly exist as single-stranded DNA-RNA hybrids, characterized by a structure which comprises a single-stranded DNA branching out of an internal guanosine residue of a single-stranded RNA molecule at a 2',5'-phosphodiester linkage. In some embodiments of the present invention, at least some of the RNA content of the msDNA molecule is degraded. In some instances, the RNA content is degraded by RNase H.

Native retrons have been found to consist of the gene for reverse transcriptase (RT) and msr and msd loci under the control of a single promoter. In some embodiments of the present invention, a vector comprising a retron-guide RNA cassette further comprises a sequence encoding an RT. In other embodiments, methods are provided wherein the RT is encoded on a separate plasmid from the retron-guide RNA cassette. In still other embodiments, the RT is encoded in a sequence that has been integrated into the host cell genome.

The msd region of a retron transcript typically codes for the DNA component of msDNA, and the msr region of a retron transcript typically codes for the RNA component of msDNA. In some retrons, the msr and msd loci have overlapping ends, and may be oriented opposite one another with a promoter located upstream of the msr locus which transcribes through the msr and msd loci. Examples of msd locus sequences are set forth in SEQ ID NOS:19 and 30. However, one of skill in the art will appreciate that the sequence of the msd locus will vary, depending on the particular donor DNA sequence that is located within the msd locus.

An exemplary msr locus sequence is set forth in SEQ ID NO:18. In some embodiments, the msr locus within the retron of a retron-gRNA cassette of the present invention comprises the nucleotide sequence set forth in SEQ ID NO:18. In other embodiments, the msr locus comprises a nucleotide sequence that has at least about 70 to about 99 percent similarity (e.g., at least about 70, 71, 72, 73, 74, 75, 76, 77, 78, 79, 80, 81, 82, 83, 84, 85, 86, 87, 88, 89, 90, 91, 92, 93, 94, 95. 96, 97, 98, or 99 percent similarity) to the nucleotide sequence set forth in SEQ ID NO: 18.

The msd and msr regions of retron transcripts generally contain first and second inverted repeat sequences, which together make up a stable stem structure. The combined msr-msd region of the retron transcript serves not only as a template for reverse transcription but, by virtue of its secondary structure, also serves as a primer (i.e., self-priming) for msDNA synthesis by a reverse transcriptase. In some embodiments of retron-guide RNA cassettes of the present invention, the first inverted repeat sequence coding region is located within the 5' end of the msr locus. In other embodiments, the second inverted repeat sequence coding region is located 3' of the msd locus. In some embodiments of retron donor DNA-guide molecules of the present invention, the first inverted repeat sequence is located within the 5' end of the msr region. In other embodiments, the second inverted repeat sequence is located 3' of the msd region. A non-limiting example is shown in FIG. 4, wherein the msr and msd loci are arranged in opposite orientations. The first inverted sequence repeat coding region is shown at the 5' end of the cassette, while the second inverted sequence repeat coding region is shown near the 3' end of the cassette.

Exemplary sequences for inverted repeat sequence coding regions are set forth in SEQ ID NOS:16 and 17. In some embodiments, a retron found within a retron-gRNA cassette of the present invention contains an inverted repeat sequence coding region that comprises the nucleotide sequence set forth in SEQ ID NO:16 or 17. As a non-limiting example, the retron can contain a first inverted repeat sequence coding region that comprises SEQ ID NO:16 and a second inverted repeat sequence coding region that comprises SEQ ID NO:17, or vice versa. In other embodiments, an inverted repeat sequence coding region comprises a nucleotide sequence that has at least about 70 to about 99 percent similarity (e.g., at least about 70, 71, 72, 73, 74, 75, 76, 77, 78, 79, 80, 81, 82, 83, 84, 85, 86, 87, 88, 89, 90, 91, 92, 93, 94, 95. 96, 97, 98, or 99 percent similarity) to the nucleotide sequence set forth in SEQ ID NO:16 or 17. As a non-limiting example, the retron can contain a first inverted repeat sequence coding region that has at least about 70 to about 99 percent similarity to SEQ ID NO:16 and a second inverted repeat sequence coding region that has at least about 70 to about 99 percent similarity to SEQ ID NO:17, or vice versa. One of ordinary skill in the art will understand that the sequence of an inverted repeat sequence coding region can be varied, so long as the sequence of the counterpart inverted repeat sequence coding region within the same retron is also varied such that the two resulting inverted repeat sequences (i.e., present within a retron transcript) are complementary and allow for the formation of a stable stem structure.

Any number of RTs may be used in alternative embodiments of the present invention, including prokaryotic and eukaryotic RTs. If desired, the nucleotide sequence of a native RT may be modified, for example using known codon optimization techniques, so that expression within the desired host is optimized. By codon optimization it is meant the selection of appropriate DNA nucleotides for the synthesis of oligonucleotide building blocks, and their subsequent enzymatic assembly, of a structural gene or fragment thereof in order to approach codon usage within the host.

The RT may be targeted to the nucleus so that efficient utilization of the RNA template may take place. An example of such a RT includes any known RT, either prokaryotic or eukaryotic, fused to a nuclear localization sequence or signal (NLS). In some embodiments of vectors of the present invention, the vector further comprises an NLS. In particular embodiments of vectors of the present invention, the NLS is located 5' of the RT coding sequence. Any suitable NLS may also be used, providing that the NLS assists in localizing the RT within the nucleus. The use of an RT in the absence of an NLS may also be used if the RT is present within the nuclear compartment at a level that synthesizes a product from the RNA template.

For more information regarding retrons, see, e.g., U.S. Pat. No. 8,932,860 and Lampson, et al. *Cytogenet. Res.* 110:491-499 (2005); both incorporated herein by reference in their entirety for all purposes.

2. Guide RNA (gRNA) Molecules

The retron-guide RNA cassettes and retron donor DNA-guide molecules of the present invention comprise guide RNA (gRNA) coding regions and gRNA molecules, respectively. The gRNAs for use in the CRISPR-retron system of the present invention typically include a crRNA sequence that is complementary to a target nucleic acid sequence and may include a scaffold sequence (e.g., tracrRNA) that interacts with a Cas nuclease (e.g., Cas9) or a variant or fragment thereof, depending on the particular nuclease being used.

The gRNA can comprise any nucleic acid sequence having sufficient complementarity with a target polynucleotide sequence (e.g., target DNA sequence) to hybridize with the target sequence and direct sequence-specific binding of a nuclease to the target sequence. The gRNA may recognize a protospacer adjacent motif (PAM) sequence that may be near or adjacent to the target DNA sequence. The target DNA site may lie immediately 5' of a PAM sequence, which is specific to the bacterial species of the Cas9 used. For instance, the PAM sequence of *Streptococcus pyogenes*-derived Cas9 is NGG; the PAM sequence of *Neisseria meningitidis*-derived Cas9 is NNNNGATT; the PAM sequence of *Streptococcus thermophilus*-derived Cas9 is NNAGAA; and the PAM sequence of *Treponema denticola*-derived Cas9 is NAAAAC. In some embodiments, the PAM sequence can be 5'-NGG, wherein N is any nucleotide; 5'-NRG, wherein N is any nucleotide and R is a purine; or 5'-NNGRR, wherein N is any nucleotide and R is a purine. For the *S. pyogenes* system, the selected target DNA sequence should immediately precede (i.e., be located 5' of) a 5'NGG PAM, wherein N is any nucleotide, such that the guide sequence of the DNA-targeting RNA (e.g., gRNA) base pairs with the opposite strand to mediate cleavage at about 3 base pairs upstream of the PAM sequence.

In other instances, the target DNA site may lie immediately 3' of a PAM sequence, e.g., when the Cpf1 endonuclease is used. In some embodiments, the PAM sequence is 5'-TTTN, where N is any nucleotide. When using the Cpf1 endonuclease, the target DNA sequence (i.e., the genomic DNA sequence having complementarity for the gRNA) will typically follow (i.e., be located 3' of) the PAM sequence. Two CP1-family nucleases, AsCpf1 (from *Acidaminococcus*) and LbCpf1 (from *Lachnospiraceae*) are known to function in human cells. Both AsCpf1 and LbCpf1 cut 19 bp after the PAM sequence on the targeted strand and 23 bp after the PAM sequence on the opposite strand of the DNA molecule.

In some embodiments, the degree of complementarity between a guide sequence of the gRNA (i.e., crRNA sequence) and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a crRNA sequence is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some instances, a crRNA sequence is about 20 nucleotides in length. In other instances, a crRNA sequence is about 15 nucleotides in length. In other instances, a crRNA sequence is about 25 nucleotides in length.

The nucleotide sequence of a modified gRNA can be selected using any of the web-based software described above. Considerations for selecting a DNA-targeting RNA include the PAM sequence for the nuclease (e.g., Cas9 or Cpf1) to be used, and strategies for minimizing off-target modifications. Tools, such as the CRISPR Design Tool, can provide sequences for preparing the gRNA, for assessing target modification efficiency, and/or assessing cleavage at off-target sites.

In some embodiments, the length of the gRNA molecule is about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, or more nucleotides in length. In some instances, the length of the gRNA is about 100 nucleotides in length. In other instances, the gRNA is about 90 nucleotides in length. In other instances, the gRNA is about 110 nucleotides in length.

3. Donor DNA Sequences

In one aspect, the present invention provides retron-guide RNA cassettes comprising a retron that comprises a donor DNA sequence. In another aspect, the present invention provides retron donor DNA-guide molecules comprising retron transcripts that comprise donor DNA sequence coding regions, the retron transcripts subsequently being reverse transcribed to yield msDNA that comprises a donor DNA sequence. The donor DNA sequence or sequences participate in homology-directed repair (HDR) of genetic loci of interest following cleavage of genomic DNA at the genetic locus or loci of interest (i.e., after a nuclease has been directed to cut at a specific genetic locus of interest, targeted by binding of gRNA to a target sequence).

In some embodiments, the recombinant donor repair template (i.e., donor DNA sequence) comprises two homology arms that are homologous to portions of the sequence of the genetic locus of interest at either side of a Cas nuclease (e.g., Cas9 or Cpf1 nuclease) cleavage site. The homology arms may be the same length or may have different lengths. In some instances, each homology arm has at least about 70 to about 99 percent similarity (i.e., at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent similarity) to a portion of the sequence of the genetic locus of interest at either side of a nuclease (e.g., Cas nuclease) cleavage site. In other embodiments, the recombinant donor repair template comprises or further comprises a reporter unit that includes a nucleotide sequence encoding a reporter polypeptide (e.g., a detectable polypeptide, fluorescent polypeptide, or a selectable marker). If present, the two homology arms can flank the reporter cassette and are homologous to portions of the genetic locus of interest at either side of the Cas nuclease cleavage site. The reporter unit can further comprise a sequence encoding a self-cleavage peptide, one or more nuclear localization signals, and/or a fluorescent polypeptide (e.g., superfolder GFP (sfGFP)). Other suitable reporters are described herein.

In some embodiments, the donor DNA sequence is at least about 500 to 10,000 (i.e., at least about 500, 600, 700, 800, 900, 1,000, 1,100, 1,200, 1,300, 1,400, 1,500, 1,600, 1,700, 1,800, 1,900, 2,000, 2,500, 3,000, 3,500, 4,000, 4,500, 5,000, 5,500, 6,000, 6,500, 7,000, 7,500, 8,000, 8,500, 9,000, 9,500, or 10,000) nucleotides in length. In some embodiments, the donor DNA sequence is between about 600 and 1,000 (i.e., about 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1,000) nucleotides in length. In some embodiments, the donor DNA sequence is between about 100 and 500 (i.e., about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500) nucleotides in length. In some embodiments, the donor DNA sequence is less than about 100 (i.e., less than about 100, 95, 90, 85, 80, 75, 70, 65, 60, 55, 50, 45, 40, 35, 30, 25, 20, 15, 10, or 5) nucleotides in length.

B. CRISPR/Cas System

The CRISPR/Cas system of genome modification includes a Cas nuclease (e.g., Cas9 or Cpf1 nuclease) or a variant or fragment or combination thereof and a DNA-targeting RNA (e.g., guide RNA (gRNA)). The gRNA may contain a guide sequence that targets the Cas nuclease to the target genomic DNA and a scaffold sequence that interacts with the Cas nuclease (e.g., tracrRNA). The system may optionally include a donor repair template. In other instances, a fragment of a Cas nuclease or a variant thereof with desired properties (e.g., capable of generating single- or double-strand breaks and/or modulating gene expression) can be used. The donor repair template can include a nucleotide sequence encoding a reporter polypeptide such as a fluorescent protein or an antibiotic resistance marker, and homology arms that are homologous to the target DNA and flank the site of gene modification.

The CRISPR (Clustered Regularly Interspaced Short Palindromic Repeats)/Cas (CRISPR-associated protein) nuclease system is an engineered nuclease system based on a bacterial system that can be used for genome engineering. It is based on part of the adaptive immune response of many bacteria and archaea. When a virus or plasmid invades a bacterium, segments of the invader's DNA are converted into CRISPR RNAs (crRNA) by the "immune" response. The crRNA then associates, through a region of partial complementarity, with another type of RNA called tracrRNA to guide the Cas (e.g., Cas9) nuclease to a region homologous to the crRNA in the target DNA called a "protospacer." The Cas (e.g., Cas9) nuclease cleaves the DNA to generate blunt ends at the double-strand break at sites specified by a 20-nucleotide guide sequence contained within the crRNA transcript. The Cas (e.g., Cas9) nuclease may require both the crRNA and the tracrRNA for site-specific DNA recognition and cleavage. This system has now been engineered such that the crRNA and tracrRNA, if needed, can be combined into one molecule (the "single guide RNA" or "sgRNA"), and the crRNA equivalent portion of the guide RNA can be engineered to guide the Cas (e.g., Cas9) nuclease to target any desired sequence (see, e.g., Jinek et al. (2012) *Science*, 337:816-821; Jinek et al. (2013) *eLife*, 2:e00471; Segal (2013) *eLife*, 2:e00563). Thus, the CRISPR/Cas system can be engineered to create a double-strand break at a desired target in a genome of a cell, and harness the cell's endogenous mechanisms to repair the induced break by homology-directed repair (HDR) or non-homologous end-joining (NHEJ).

The Cas nuclease can direct cleavage of one or both strands at a location in a target DNA sequence. For example, the Cas nuclease can be a nickase having one or more inactivated catalytic domains that cleaves a single strand of a target DNA sequence.

Non-limiting examples of Cas nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, variants thereof, fragments thereof, mutants thereof, derivatives thereof, and combinations thereof. There are three main types of Cas nucleases (type I, type II, and type III), and 10 subtypes including 5 type I, 3 type II, and 2 type III proteins (see, e.g., Hochstrasser and Doudna, *Trends Biochem Sci*, 2015:40(1):58-66). Type II Cas nucleases include Cas1, Cas2, Csn2, Cas9, and Cpf1. These Cas nucleases are known to those skilled in the art. For example, the amino acid sequence of the *Streptococcus pyogenes* wild-type Cas9 polypeptide is set forth, e.g., in NBCI Ref. Seq. No. NP_269215, and the amino acid sequence of *Streptococcus thermophilus* wild-type Cas9 polypeptide is set forth, e.g., in NBCI Ref. Seq. No. WP_011681470. Furthermore, the amino acid sequence of *Acidaminococcus* sp. BV3L6 is set forth, e.g., in NBCI Ref. Seq. No. WP_021736722.1. Some CRISPR-related endonucleases that are useful in the present invention are disclosed, e.g., in U.S. Application Publication Nos. 2014/0068797, 2014/0302563, and 2014/0356959.

Cas nucleases, e.g., Cas9 polypeptides, can be derived from a variety of bacterial species including, but not limited to, *Veillonella atypical, Fusobacterium nucleatum, Filifactor alocis, Solobacterium moorei, Coprococcus catus, Treponema denticola, Peptoniphilus duerdenii, Catenibacterium mitsuokai, Streptococcus mutans, Listeria innocua, Staphylococcus pseudintermedius, Acidaminococcus intestine, Olsenella uli, Oenococcus kitaharae, Bifidobacterium bifidum, Lactobacillus rhamnosus, Lactobacillus gasseri, Finegoldia magna, Mycoplasma mobile, Mycoplasma gallisepticum, Mycoplasma ovipneumoniae, Mycoplasma canis, Mycoplasma synoviae, Eubacterium rectale, Streptococcus thermophilus, Eubacterium dolichum, Lactobacillus coryniformis* subsp. *Torquens, Ilyobacter polytropus, Ruminococcus albus, Akkermansia muciniphila, Acidothermus cellulolyticus, Bifidobacterium longum, Bifidobacterium dentium, Corynebacterium diphtheria, Elusimicrobium minutum, Nitratifractor salsuginis, Sphaerochaeta globus, Fibrobacter succinogenes* subsp. *Succinogenes, Bacteroides fragilis, Capnocytophaga ochracea, Rhodopseudomonas palustris, Prevotella micans, Prevotella ruminicola, Flavobacterium columnare, Aminomonas paucivorans, Rhodospirillum rubrum, Candidatus Puniceispirillum marinum, Verminephrobacter eiseniae, Ralstonia syzygii, Dinoroseobacter shibae, Azospirillum, Nitrobacter hamburgensis, Bradyrhizobium, Wolinella succinogenes, Campylobacter jejuni* subsp. *Jejuni, Helicobacter mustelae, Bacillus cereus, Acidovorax ebreus, Clostridium perfringens, Parvibaculum lavamentivorans, Roseburia intestinalis, Neisseria meningitidis, Pasteurella multocida* subsp. *Multocida, Sutterella wadsworthensis, proteobacterium, Legionella pneumophila, Parasutterella excrementihominis, Wolinella succinogenes*, and *Francisella novicida*.

"Cpf1" refers to an RNA-guided double-stranded DNA-binding nuclease protein that is a type II Cas nuclease. Wild-type Cpf1 contains a RuvC-like endonuclease domain similar to the RuvC domain of Cas9, but does not have an HNH endonuclease domain and the N-terminal region of Cpf1 does not have the alpha-helix recognition lobe possessed by Cas9. The wild-type protein requires a single RNA molecule, as no tracrRNA is necessary. Wild-type Cpf1 creates staggered-end cuts and utilizes a T-rich protospacer-adjacent motif (PAM) that is 5' of the guide RNA targeting sequence. Cpf1 enzymes have been isolated, for example, from *Acidaminococcus* and *Lachnospiraceae*.

"Cas9" refers to an RNA-guided double-stranded DNA-binding nuclease protein or nickase protein that is a type II Cas nuclease. Wild-type Cas9 nuclease has two functional domains, e.g., RuvC and HNH, that cut different DNA strands. The wild-type enzyme requires two RNA molecules (e.g., a crRNA and a tracrRNA), or alternatively, a single fusion molecule (e.g., a gRNA comprising a crRNA and a tracrRNA). Wild-type Cas9 utilizes a G-rich protospacer-adjacent motif (PAM) that is 3' of the guide RNA targeting sequence and creates double-strand cuts having blunt ends. Cas9 can induce double-strand breaks in genomic DNA (target DNA) when both functional domains are active. The Cas9 enzyme can comprise one or more catalytic domains of a Cas9 protein derived from bacteria belonging to the group consisting of *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor*, and *Campylobacter*. In some embodiments, the two catalytic domains are derived from different bacteria species.

Useful variants of the Cas9 nuclease can include a single inactive catalytic domain, such as a RuvC⁻ or HNH⁻ enzyme or a nickase. A Cas9 nickase has only one active functional domain and can cut only one strand of the target DNA, thereby creating a single-strand break or nick. A double-strand break can be introduced using a Cas9 nickase if at least two DNA-targeting RNAs that target opposite DNA strands are used. A double-nicked induced double-strand break can be repaired by NHEJ or HDR (Ran et al., 2013, Cell, 154:1380-1389). This gene editing strategy favors HDR and decreases the frequency of insertion/deletion ("indel") mutations at off-target DNA sites. Non-limiting examples of Cas9 nucleases or nickases are described in, for example, U.S. Pat. Nos. 8,895,308; 8,889,418; and 8,865,406 and U.S. Application Publication Nos. 2014/0356959, 2014/0273226 and 2014/0186919. The Cas9 nuclease or nickase can be codon-optimized for the host cell or host organism.

For genome editing methods, the Cas nuclease can be a Cas9 fusion protein such as a polypeptide comprising the catalytic domain of a restriction enzyme (e.g., FokI) linked to dCas9. The FokI-dCas9 fusion protein (fCas9) can use two guide RNAs to bind to a single strand of target DNA to generate a double-strand break.

In some embodiments, a nucleotide sequence encoding the Cas nuclease is present in a recombinant expression vector. In certain instances, the recombinant expression vector is a viral construct, e.g., a recombinant adeno-associated virus construct, a recombinant adenoviral construct, a recombinant lentiviral construct, etc. For example, viral vectors can be based on vaccinia virus, poliovirus, adenovirus, adeno-associated virus, SV40, herpes simplex virus, human immunodeficiency virus, and the like. A retroviral vector can be based on Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, mammary tumor virus, and the like. Useful expression vectors are known to those of skill in the art, and many are commercially available. The following vectors are provided by way of example for eukaryotic host cells: pXT1, pSG5, pSVK3, pBPV, pMSG, and pSVLSV40. However, any other vector may be used if it is compatible with the host cell. For example, useful expression vectors containing a nucleotide sequence encoding a Cas9 enzyme are commercially available from, e.g., Addgene, Life Technologies, Sigma-Aldrich, and Origene.

Depending on the host cell and expression system used, any of a number of transcription and translation control elements, including promoter, transcription enhancers, transcription terminators, and the like, may be used in the expression vector. Useful promoters can be derived from viruses, or any organism, e.g., prokaryotic or eukaryotic organisms. Promoters may also be inducible (i.e., capable of responding to environmental factors and/or external stimuli that can be artificially controlled). Suitable promoters include, but are not limited to: RNA polymerase II promoters (e.g., pGAL7 and pTEF1), RNA polymerase III promoters (e.g., RPR-tetO, SNR52, and tRNA-tyr), the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, a human H1 promoter (H1), etc. Suitable terminators include, but are not limited to SNR52 and RPR terminator sequences (non-limiting examples of which are set forth in SEQ ID NO:37 and 38, respectively), which can be used with transcripts created under the control of a RNA polymerase III promoter. Additionally, various primer binding sites may be incorporated into a vector to facilitate vector cloning, sequencing, genotyping, and the like. As a non-limiting example, the Pci1-Up sequence set forth in SEQ ID NO:26 can be incorporated. Other suitable promoter, enhancer, terminator, and primer binding sequences will readily be known to one of skill in the art.

C. Methods for Introducing Nucleic Acids into Host Cells

Methods for introducing polypeptides and nucleic acids into a host cell are known in the art, and any known method can be used to introduce a nuclease or a nucleic acid (e.g., a nucleotide sequence encoding the nuclease or reverse transcriptase, a DNA-targeting RNA (e.g., a guide RNA), a donor repair template for homology-directed repair (HDR), etc.) into a cell. Non-limiting examples of suitable methods include electroporation, viral or bacteriophage infection, transfection, conjugation, protoplast fusion, lipofection, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

In some embodiments, the components of the CRISPR-retron system can be introduced into a cell using a delivery system. In certain instances, the delivery system comprises a nanoparticle, a microparticle (e.g., a polymer micropolymer), a liposome, a micelle, a virosome, a viral particle, a nucleic acid complex, a transfection agent, an electroporation agent (e.g., using a NEON transfection system), a nucleofection agent, a lipofection agent, and/or a buffer system that includes a nuclease component (as a polypeptide or encoded by an expression construct), a reverse transcriptase component, and one or more nucleic acid components such as a DNA-targeting RNA (e.g., a guide RNA) and/or a donor repair template. For instance, the components can be mixed with a lipofection agent such that they are encapsulated or packaged into cationic submicron oil-in-water emulsions. Alternatively, the components can be delivered without a delivery system, e.g., as an aqueous solution.

Methods of preparing liposomes and encapsulating polypeptides and nucleic acids in liposomes are described in, e.g., Methods and Protocols, Volume 1: Pharmaceutical Nanocarriers: Methods and Protocols. (ed. Weissig). Humana Press, 2009 and Heyes et al. (2005) *J Controlled Release* 107:276-87. Methods of preparing microparticles and encapsulating polypeptides and nucleic acids are described in, e.g., Functional Polymer Colloids and Microparticles volume 4 (Microspheres, microcapsules & liposomes). (eds. Arshady & Guyot). Citus Books, 2002 and *Microparticulate Systems for the Delivery of Proteins and Vaccines*. (eds. Cohen & Bernstein). CRC Press, 1996.

D. Host Cells

In a particular aspect, the present invention provides host cells that have been transformed by vectors of the present invention. The compositions and methods of the present invention can be used for genome editing of any host cell of interest. The host cell can be a cell from any organism, e.g., a bacterial cell, an archaeal cell, a cell of a single-cell eukaryotic organism, a plant cell (e.g., a rice cell, a wheat cell, a tomato cell, an *Arabidopsis thaliana* cell, a *Zea mays* cell and the like), an algal cell (e.g., *Botryococcus braunii, Chlamydomonas reinhardtii, Nannochloropsis gaditana, Chlorella pyrenoidosa, Sargassum patens C. Agardh*, and the like), a fungal cell (e.g., yeast cell, etc.), an animal cell, a cell from an invertebrate animal (e.g., fruit fly, cnidarian, echinoderm, nematode, etc.), a cell from a vertebrate animal (e.g., fish, amphibian, reptile, bird, mammal, etc.), a cell from a mammal, a cell from a human, a cell from a healthy human, a cell from a human patient, a cell from a cancer patient, etc. In some cases, the host cell treated by the method disclosed herein can be transplanted to a subject (e.g., patient). For instance, the host cell can be derived from the subject to be treated (e.g., patient).

Any type of cell may be of interest, such as a stem cell, e.g., embryonic stem cell, induced pluripotent stem cell, adult stem cell, e.g., mesenchymal stem cell, neural stem cell, hematopoietic stem cell, organ stem cell, a progenitor cell, a somatic cell, e.g., fibroblast, hepatocyte, heart cell, liver cell, pancreatic cell, muscle cell, skin cell, blood cell, neural cell, immune cell, and any other cell of the body, e.g., human body. The cells can be primary cells or primary cell cultures derived from a subject, e.g., an animal subject or a human subject, and allowed to grow in vitro for a limited number of passages. In some embodiments, the cells are disease cells or derived from a subject with a disease. For instance, the cells can be cancer or tumor cells. The cells can also be immortalized cells (e.g., cell lines), for instance, from a cancer cell line.

Cells can be harvested from a subject by any standard method. For instance, cells from tissues, such as skin, muscle, bone marrow, spleen, liver, kidney, pancreas, lung, intestine, stomach, etc., can be harvested by a tissue biopsy or a fine needle aspirate. Blood cells and/or immune cells can be isolated from whole blood, plasma or serum. In some cases, suitable primary cells include peripheral blood mononuclear cells (PBMC), peripheral blood lymphocytes (PBL), and other blood cell subsets such as, but not limited to, T cell, a natural killer cell, a monocyte, a natural killer T cell, a monocyte-precursor cell, a hematopoietic stem cell or a non-pluripotent stem cell. In some cases, the cell can be any immune cells including any T-cell such as tumor infiltrating cells (TILs), such as CD3+ T-cells, CD4+ T-cells, CD8+ T-cells, or any other type of T-cell. The T cell can also include memory T cells, memory stem T cells, or effector T cells. The T cells can also be skewed towards particular populations and phenotypes. For example, the T cells can be skewed to phenotypically comprise, CD45RO(−), CCR7(+), CD45RA(+), CD62L(+), CD27(+), CD28(+) and/or IL-7Ra (+). Suitable cells can be selected that comprise one of more markers selected from a list comprising: CD45RO(−), CCR7 (+), CD45RA(+), CD62L(+), CD27(+), CD28(+) and/or IL-7Ra(+). Induced pluripotent stem cells can be generated from differentiated cells according to standard protocols described in, for example, U.S. Pat. Nos. 7,682,828, 8,058, 065, 8,530,238, 8,871,504, 8,900,871 and 8,791,248, the disclosures are herein incorporated by reference in their entirety for all purposes.

In some embodiments, the host cell is in vitro. In other embodiments, the host cell is ex vivo. In yet other embodiments, the host cell is in vivo.

E. Methods for Genome Editing and Screening, and Assessing the Efficiency and Precision Thereof In another aspect, the present invention provides a method for modifying one or more target nucleic acids of interest at one or more target loci within a genome of a host cell. In some embodiments, the method comprises:

(a) transforming the host cell with a vector of the present invention; and
(b) culturing the host cell or transformed progeny of the host cell under conditions sufficient for expressing from the vector a retron donor DNA-guide molecule comprising a retron transcript and a guide RNA (gRNA) molecule,
wherein the retron transcript self-primes reverse transcription by a reverse transcriptase (RT) expressed by the host cell or the transformed progeny of the host cell,
wherein at least a portion of the retron transcript is reverse transcribed to produce a multicopy single-stranded DNA (msDNA) molecule having one or more donor DNA sequences, wherein the one or more donor DNA sequences are homologous to the one or more target loci and comprise sequence modifications compared to the one or more target nucleic acids,
wherein the one or more target loci are cut by a nuclease expressed by the host cell or the transformed progeny of the host cell, wherein the site of nuclease cutting is specified by the gRNA, and
wherein the one or more donor DNA sequences recombine with the one or more target nucleic acid sequences to insert, delete, and/or substitute one or more bases of the sequence of the one or more target nucleic acid sequences to induce one or more sequence modifications at the one or more target loci within the genome.

In some embodiments, the host cell is capable of expressing the RT prior to transforming the host cell with the vector. In some instances, the RT is encoded in a sequence that is integrated into the genome of the host cell. In other instances, the RT is encoded in a sequence on a separate plasmid. In other embodiments, the host cell is capable of expressing the RT at the same time as, or after, transforming the host cell with the vector. In some instances, the RT is expressed from the vector. In other instances, the RT is encoded in a sequence on a separate plasmid.

In other embodiments, the host cell is capable of expressing the nuclease (e.g., Cas9) prior to transforming the host cell with the vector. In some instances, the nuclease is encoded in a sequence that is integrated into the genome of the host cell. In other instances, the nuclease is encoded in a sequence on a separate plasmid. In other embodiments, the host cell is capable of expressing the nuclease at the same time as, or after, transforming the host cell with the vector. In some instances, the nuclease is expressed from the vector. In other instances, the nuclease is encoded in a sequence on a separate plasmid.

In some embodiments, the vector comprises a retron-gRNA cassette that, when transcribed, yields a retron transcript and gRNA that are physically coupled. In such embodiments, the resulting donor DNA sequence within the msDNA and the gRNA can also be physically coupled. In particular embodiments, the retron transcript and gRNA subsequently become physically uncoupled (e.g., before or after reverse transcription of the retron transcript occurs). Physical uncoupling of the retron transcript and the gRNA can result from, for example, ribozyme cleavage (e.g., the retron-gRNA cassette also contains a ribozyme sequence). In such embodiments, the resulting donor DNA sequence within the msDNA and the gRNA will be physically uncoupled (e.g., during genome editing and/or screening).

In some embodiments, the retron transcript and the gRNA are not initially physically coupled. In particular embodiments, the retron transcript and the gRNA are subsequently joined together. Transcription event(s) that result in the production of the retron transcript and/or gRNA can occur inside a host cell, outside of a host cell (e.g., followed by introduction of the retron transcript and/or gRNA into the host cell), or a combination thereof. In some embodiments, the one or more target nucleic acids of interest are modified by a donor DNA sequence (e.g., within a msDNA) and a gRNA that are never physically coupled. For example, the donor DNA sequence and the gRNA can be expressed from different cassettes (e.g., which are contained in the same vector or different vectors) and the donor DNA sequence and the gRNA can act in trans.

In yet another aspect, the present invention provides a method for screening one or more genetic loci of interest in a genome of a host cell, the method comprising:
(a) modifying one or more target nucleic acids of interest at one or more target loci within the genome of the host cell according to a method of the present invention;
(b) incubating the modified host cell under conditions sufficient to elicit a phenotype that is controlled by the one or more genetic loci of interest;
(c) identifying the resulting phenotype of the modified host cell; and
(d) determining that the identified phenotype was the result of the modifications made to the one or more target nucleic acids of interest at the one or more target loci of interest.

To assess the efficiency and/or precision of genome editing (e.g., testing for whether an edit has been made and/or the accuracy of the edit), the target DNA can be analyzed by standard methods known to those in the art. For example, indel mutations can be identified by sequencing using the SURVEYOR® mutation detection kit (Integrated DNA Technologies, Coralville, IA) or the Guide-It™ Indel Identification Kit (Clontech, Mountain View, CA). Homology-directed repair (HDR) can be detected by PCR-based methods, and in combination with sequencing or RFLP analysis. Non-limiting examples of PCR-based kits include the Guide-it Mutation Detection Kit (Clontech) and the GeneArt® Genomic Cleavage Detection Kit (Life Technologies, Carlsbad, CA). Deep sequencing can also be used, particularly for a large number of samples or potential target/off-target sites.

In some other embodiments, editing efficiency can be assessed by employing a reporter or selectable marker to examine the phenotype of an organism or a population of organisms. In some instances, the marker produces a visible phenotype, such as the color of an organism or population of organisms. As a non-limiting example, edits can be made that either restore or disrupt the function of metabolic pathways that confer a visible phenotype (e.g., a color) to the organism. In the scenario where a successful genome edit results in a color change in the target organism (e.g., because the edit disrupts a metabolic pathway that results in a color change or because the edit restores function in a pathway that results in a color change), the absolute number or the proportion of organisms or their progeny that exhibit a color change (e.g., an estimated or direct count of the number of organisms exhibiting a color change divided by the total number of organisms for which the genomes were potentially edited) can serve as a measure of editing efficiency. In some instances, the phenotype is examined by growing the target organisms and/or their progeny under conditions that result in a phenotype, wherein the phenotype may not be visible under ordinary growth conditions. As a non-limiting example, growing yeast in a culture medium that is adenine deficient can lead to a particular phenotype (e.g., a color change) in yeast cells that possess a genetic defect in adenine synthesis. As such, growing yeast cells in adenine-deficient media can allow one to discern the effect of genome edits that putatively target adenine biosynthesis loci.

In some embodiments, the reporter or selectable marker is a fluorescent tagged protein, an antibody, a labeled antibody, a chemical stain, a chemical indicator, or a combination thereof. In other embodiments, the reporter or selectable marker responds to a stimulus, a biochemical, or a change in environmental conditions. In some instances, the reporter or selectable marker responds to the concentration of a metabolic product, a protein product, a synthesized drug of interest, a cellular phenotype of interest, a cellular product of interest, or a combination thereof. A cellular product of interest can be, as a non-limiting example, an RNA molecule (e.g., messenger RNA (mRNA), long non-coding RNA (lncRNA), microRNA (miRNA)).

Editing efficiency can also be examined or expressed as a function of time. For example, an editing experiment can be allowed to run for a fixed period of time (e.g., 24 or 48 hours) and the number of successful editing events in that fixed time period can be determined. Alternatively, the proportion of successful editing events can be determined for a fixed period of time. Typically, longer editing periods will result in a larger number of successful editing events. Editing experiments or procedures can run for any length of time. In some embodiments, a genome editing experiment or procedure runs for several hours (e.g., about 1, 2, 3, 4, 5, 6, 7, 8, 9, 10, 11, 12, 13, 14, 15, 16, 17, 18, 19, 20, 21, 22, 23, or 24 hours). In other embodiments, a genome editing experiment or procedure runs for several days (e.g., about 1, 2, 3, 4, 5, 6, or 7 days).

In addition to the length of time of the editing period, editing efficiency can be affected by the choice of gRNA, donor DNA sequence, the choice of promoter used, or a combination thereof.

In other embodiments, editing efficiency is compared to a control efficiency. In some embodiments, the control efficiency is determined by running a genome editing experiment in which the retron transcript and gRNA molecule are never physically coupled, or are initially coupled but subsequently become uncoupled. In some instances, the retron transcript and gRNA molecule are initially coupled and then become uncoupled (e.g., by ribozyme cleavage). In other instances, the retron-guide RNA (gRNA) cassette is configured such that the transcript products of the retron and gRNA coding region are never physically coupled. In yet other instances, the retron transcript and gRNA are introduced into the host cell separately. In some instances, the methods and compositions of the present invention result in at least about a 1.3- to 3-fold (i.e., at least about a 1.3-, 1.4-, 1.5-, 1.6-, 1.7-, 1.8-, 1.9-, 2-, 2.1-, 2.2-, 2.3-, 2.4-, 2.5-, 2.6-, 2.7-, 2.8-, 2.9-, or 3-fold) increase in efficiency, compared to when the retron transcript and gRNA are not physically coupled during editing. In other instances, at least about a 3- to 10-fold increase (i.e., at least about a 3-, 4-, 5-, 6-, 7-, 8-, 9-, or 10-fold) increase in efficiency is produced, compared to when the retron transcript and gRNA are not physically coupled during editing. In particular instances, at least about a 10- to 100-fold (i.e., at least about 10-, 20-, 30-, 40-, 50-, 60-, 70-, 80-, 90-, or 100-fold) increase in efficiency is produced, compared to when the retron transcript and gRNA are not physically coupled during editing.

Editing efficiency can also be improved by performing editing experiments or procedures in a multiplex format. In some embodiments, multiplexing comprises cloning two or more editing retron-gRNA cassettes in tandem into a single vector. In some instances, at least about 10 retron-gRNA cassettes (i.e., at least about 2, 3, 4, 5, 6, 7, 8, 9, or 10 retron-gRNA cassettes) are cloned into a single vector.

In other embodiments, multiplexing comprises transforming a host cell with two or more vectors. Each vector can comprise one or multiple retron-gRNA cassettes. In some instances, at least about 10 vectors (i.e., at least about 2, 3, 4, 5, 6, 7, 8, 9, or 10 vectors) are used to transform an individual host cell.

In still other embodiments, multiplexing comprises transforming two or more individual host cells, each with a different vector or combination of vectors. In some instances, at least about 2 host cells (i.e., at least about 2, 3, 4, 5, 6, 7, 8, 9, or 10 host cells) are transformed. In other instances, between about 10 and 100 host cells (i.e., about 10, 15, 20, 25, 30, 35, 40, 45, 50, 55, 60, 65, 70, 75, 80, 85, 90, 95, or 100 host cells) are transformed. In still other instances, between about 100 and 1,000 host cells (i.e., about 100, 200, 300, 400, 500, 600, 700, 800, 900, or 1,000 host cells) are transformed. In particular instances, between about 1,000 and 10,000 host cells (i.e., about 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, or 10,000 host cells are transformed). In some other instances, between about 10,000 and 100,000 host cells (i.e., about 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, or 100,000 host cells) are transformed. In other instances, between about 100,000 and 1,000,000 host cells (i.e., at least about 100,000, 150,000, 200,000, 250,000, 300,000, 350,000, 400,000, 450,000, 500,000, 550,000, 600,000, 650,000, 700,000, 750,000, 800,000, 850,000, 900,000, 950,000 or 1,000,000 host cells) are transformed. In some instances, more than about 1,000,000 host cells are transformed. Also, multiple embodiments of multiplexing can be combined.

By using one or a combination of the various multiplexing embodiments, it is possible to modify and/or screen any number of loci within a genome. In some instances, at least about 10 (i.e., about 1, 2, 3, 4, 5, 6, 7, 8, 9, or 10) genetic loci are modified or screened. In other instances, between about 10 and 100 (i.e., about 10, 15, 20, 25, 30, 35, 40, 45, 50, 55, 60, 65, 70, 75, 80, 85, 90, 95, or 100) loci are modified or screened. In still other instances, between about 100 and 1,000 genetic loci (i.e., about 100, 150, 200, 250, 300, 350, 400, 450, 500, 550, 600, 650, 700, 750, 800, 850, 900, 950, or 1,000 genetic loci) are modified or screened. In some other instances, between about 1,000 and 100,000 genetic loci (i.e., about 1,000, 1,500, 2,000, 2,500, 3,000, 3,500, 4,000, 4,500, 5,000, 5,500, 6,000, 6,500, 7,000, 7,500, 8,000, 8,500, 9,000, 9,500 10,000, 15,00, 20,000, 25,000, 30,000, 35,000, 40,000, 45,000, 50,000, 55,000, 60,000, 65,000, 70,000, 75,000, 80,000, 85,000, 90,000, 95,000, or 100,000 genetic loci) are modified or screened. In particular instances, between about 100,000 and 1,000,000 genetic loci (i.e., about 100,000, 150,000, 200,000, 250,000, 300,000, 350,000, 400,000, 450,000, 500,000, 550,000, 600, 000, 650,000, 700,000, 750,000, 800,000, 850,000, 900,000, 950,000, or 1,000,000 genetic loci) are modified or screened. In certain instances, more than about 1,000,000 loci are screened.

In some embodiments, the host cell or host cell comprises a population of host cells. In some instances, one or more sequence modifications are induced in at least about 20 percent (i.e., at least about 20, 21, 22, 23, 24, 25, 26, 27, 28, 29, 30, 35, 40, 45, 50, 55, 60, 65, 70, 75, 80, 85, 90, 95, or 100 percent) of the population of cells. In other instances, one or more sequence modifications are induced in at least about 50 percent (i.e., at least about 50, 51, 52, 53, 54, 55, 56, 57, 58, 59, 60, 65, 70, 75, 80, 85, 90, 95, or 100 percent) of the population of cells. In still other instances, one or more sequence modifications are induced in at least about 75 percent (i.e., at least about 75, 76, 77, 78, 79, 80, 81, 82, 83, 84, 85, 86, 87, 88, 89, 90, 95, or 100 percent) of the population of cells. In other instances, one or more sequence modifications are induced in at least about 90 percent (i.e., at least about 90, 91, 92, 93, 94, 95, 96, 97, 98, 99, or 100 percent) of the population of cells. In particular instances, one or more sequence modifications are induced in at least about 95 percent (i.e., at least about 95, 96, 97, 98, 99, or 100 percent) of the population of cells.

The precision of genome editing can correspond to the number or percentage of on-target genome editing events relative to the number or percentage of all genome editing events, including on-target and off-target events. Testing for on-target genome editing events can be accomplished by direct sequencing of the target region or other methods described herein. When employing the compositions and methods of the present invention, in some instances, editing precision is at least about 80 percent (i.e., at least about 80, 81, 82, 83, 84, 85, 86, 87, 88, 89, 90, 95, or 100 percent), meaning that at least about 80 percent of all genome editing events are on-target editing events. In other instances, editing precision is at least about 90 percent (i.e., at least about 90, 91, 92, 93, 94, 95, 96, 97, 98, 99, or 100 percent), meaning that at least about 90 percent of all genome editing events are on-target editing events. In some other instances, editing precision is at least about 95 percent (i.e., at least about 95, 96, 97, 98, 99, or 100 percent), meaning that at least about 95 percent of all genome editing events are on-target editing events. In particular instances, editing precision is at least about 99 percent (i.e., at least about 99 or 100 percent), meaning that at least 99 percent of all genome editing events are on-target editing events.

F. Methods for Preventing or Treating Genetic Diseases

In another aspect, the present invention provides a pharmaceutical composition comprising:
(a) a retron-guide RNA cassette of the present invention, a vector of the present invention, a retron donor-DNA guide molecule of the present invention, or a combination thereof; and
(b) a pharmaceutically acceptable carrier.

In yet another aspect of the present invention, provided herein is a method for preventing or treating a genetic disease in a subject, the method comprising administering to the subject an effective amount of a pharmaceutical composition of the present invention to correct a mutation in a target gene associated with the genetic disease.

The compositions and methods of the present invention are suitable for any disease that has a genetic basis and is amenable to prevention or amelioration of disease-associated sequelae or symptoms by editing or correcting one or more genetic loci that are linked to the disease. Non-limiting examples of diseases include X-linked severe combined immune deficiency, sickle cell anemia, thalassemia, hemophilia, neoplasia, cancer, age-related macular degeneration, schizophrenia, trinucleotide repeat disorders, fragile X syndrome, prion-related disorders, amyotrophic lateral sclerosis, drug addiction, autism, Alzheimer's disease, Parkinson's disease, cystic fibrosis, blood and coagulation diseases and disorders, inflammation, immune-related diseases and disorders, metabolic diseases and disorders, liver diseases and disorders, kidney diseases and disorders, muscular/skeletal diseases and disorders, neurological and neuronal diseases and disorders, cardiovascular diseases and disorders, pulmonary diseases and disorders, and ocular diseases. The compositions and methods of the present invention can also be used to prevent or treat any combination of suitable genetic diseases.

In some embodiments, the subject is treated before any symptoms or sequelae of the genetic disease develop. In other embodiments, the subject has symptoms or sequelae of the genetic disease. In some instances, treatment results in a reduction or elimination of the symptoms or sequelae of the genetic disease.

In some embodiments, treatment includes administering compositions of the present invention directly to a subject. As a non-limiting example, pharmaceutical compositions of the present invention can be delivered directly to a subject (e.g., by local injection or systemic administration). In other embodiments, the compositions of the present invention are delivered to a host cell or population of host cells, and then the host cell or population of host cells is administered or transplanted to the subject. The host cell or population of host cells can be administered or transplanted with a pharmaceutically acceptable carrier. In some instances, editing of the host cell genome has not yet been completed prior to administration or transplantation to the subject. In other instances, editing of the host cell genome has been completed when administration or transplantation occurs. In certain instances, progeny of the host cell or population of host cells are transplanted into the subject. In some embodiments, correct editing of the host cell or population of host cells, or the progeny thereof, is verified before administering or transplanting edited cells or the progeny thereof into a subject. Procedures for transplantation, administration, and verification of correct genome editing are discussed herein and will be known to one of skill in the art.

Compositions of the present invention, including cells and/or progeny thereof that have had their genomes edited by the methods and/or compositions of the present invention, may be administered as a single dose or as multiple doses, for example two doses administered at an interval of about one month, about two months, about three months, about six months or about 12 months. Other suitable dosage schedules can be determined by a medical practitioner.

Prevention or treatment can further comprise administering agents and/or performing procedures to prevent or treat concomitant or related conditions. As non-limiting examples, it may be necessary to administer drugs to suppress immune rejection of transplanted cells, or prevent or reduce inflammation or infection. A medical professional will readily be able to determine the appropriate concomitant therapies.

G. Kits

In another aspect, the present invention provides kit for modifying one or more target nucleic acids of interest at one or more target loci within a genome of a host cell, the kit comprising one or a plurality of vectors of the present invention. The kit may further comprise a host cell or a plurality of host cells.

In some embodiments, the kit contains one or more reagents. In some instances, the reagents are useful for transforming a host cell with a vector or a plurality of vectors, and/or inducing expression from the vector or plurality of vectors. In other embodiments, the kit may further comprise a reverse transcriptase, a plasmid for expressing a reverse transcriptase, one or more nucleases, one or more plasmids for expressing one or more nucleases, or a combination thereof. The kit may further comprise one or more reagents useful for delivering nucleases or reverse transcriptases into the host cell and/or inducing expression of the reverse transcriptase and/or the one or more nucleases. In yet other embodiments, the kit further comprises instructions for transforming the host cell with the vector, introducing nucleases and/or reverse transcriptases into the host cell, inducing expression of the vector, reverse transcriptase, and/or nucleases, or a combination thereof.

In yet another aspect, the present invention provides a kit for modifying one or more target nucleic acids of interest at one or more target loci within a genome of a host cell, the kit comprising one or a plurality of retron donor DNA-guide molecules of the present invention. The kit may further comprise a host cell or a plurality of host cells.

In some embodiments, the kit contains one or more reagents. In some instances, the reagents are useful for introducing the retron donor DNA-guide molecule or plurality thereof into the host cell. In other embodiments, the kit may further comprise a reverse transcriptase, a plasmid for expressing a reverse transcriptase, one or more nucleases, one or more plasmids for expressing one or more nucleases, or a combination thereof. The kit may further comprise one or more reagents useful for delivering into the host cell reverse transcriptases and/or nucleases and/or inducing expression of the reverse transcriptase and/or the one or more nucleases. In yet other embodiments, the kit further comprises instructions for introducing the retron donor DNA-guide molecule or plurality thereof into the host cell, introducing nucleases and/or reverse transcriptases into the host cell, inducing expression of the reverse transcriptase and/or nucleases, or a combination thereof.

H. Applications

The compositions and methods provided by the present invention are useful for any number of applications. As non-limiting examples, genome editing can be performed to correct detrimental lesions in order to prevent or treat a disease, or to identify one or more specific genetic loci that contribute to a phenotype, disease, biological function, and the like. As another non-limiting example, genome editing or screening according to the compositions and methods of the present invention can be used to improve or optimize a biological function, pathway, or biochemical entity (e.g., protein optimization). Such optimization applications are especially suited to the compositions and methods of the present invention, as they can require the modification of a large number of genetic loci and subsequently assessing the effects.

Other non-limiting examples of applications suitable for the compositions and methods of the present invention include the production of recombinant proteins for pharmaceutical and industrial use, the production of various pharmaceutical and industrial chemicals, the production of vaccines and viral particles, and the production of fuels and nutraceuticals. All of these applications typically involve high-throughput or high-content screening, making them especially suited to the compositions and methods of the present invention.

In some embodiments, inducing one or more sequence modifications at one or more genetic loci of interest comprises substituting, inserting, and/or deleting one or more nucleotides at the one or more genetic loci of interest. In some instances, inducing the one or more sequence modifications results in the insertion of one or more sequences encoding cellular localization tags, one or more synthetic response elements, and/or one or more sequences encoding degrons into the genome.

In other embodiments, inducing the one or more sequence modifications at the one or more genetic loci of interest results in the insertion of one or more sequences from a heterologous genome. Introducing heterologous DNA sequences into a genome is useful for any number of applications, some of which are described herein. Others will be readily apparent to one of skill in the art. Non-limiting examples are directed protein evolution, biological pathway optimization, and production of recombinant pharmaceuticals.

In certain embodiments, inducing the one or more sequence modifications at the one or more genetic loci of interest results in the insertion of one or more "barcodes" (i.e., nucleotide sequences that allow identification of the source of a particular specimen or sample). As non-limiting examples, the insertion of barcodes can be used for cell lineage tracking or the measurement of RNA abundance.

V. Examples

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1. Yeast Genome Editing

This example shows the efficiency of the CRISPR-retron system for editing genomes, utilizing a visual genetic marker.

Introduction

Earlier CRISPR genome editing approaches utilize a guide RNA (gRNA) that directs the cleavage of a specific genomic sequence by a nuclease such as Cas9, and preferably a donor DNA repair template, with the gRNA and donor DNA template being provided as separate molecules. Because of this, in the past it has been necessary for CRISPR editing experiments to be performed in multiple tubes or vessels. However, as shown herein, the efficiency of genome editing is improved by employing a CRISPR-retron system, wherein a gRNA is tethered to a donor DNA sequence that serves as the repair template.

To test the editing efficiency of the CRISPR-retron system, individual DNA fragments containing the wild type $E.$ $coli$ msr-msd region with donor DNA sequences inserted into a variable region and flanked by the corresponding targeting gRNA were designed and synthesized (FIG. 3). These fragments were subsequently cloned into expression vectors containing various promoters including the RNA polymerase III promoters RPR1-tetO (inducible), SNR52, and tRNA-Tyr as well as the RNA polymerase II promoters GAL7 (inducible) and TEF1 flanked by HDV ribozymes. The $E.$ $coli$ Ec86 reverse transcriptase DNA sequence was codon optimized for expression in $Saccharomyces$ $cerevisiae$, an N-terminal SV40 nuclear localizing sequence was added, and the reverse transcriptase was expressed coordinately with SpCas9 using the bidirectional galactose inducible promoter pGal1-pGal10. The expression of these two proteins can be achieved either on the same plasmid as the retron-donor DNA-gRNA cassette, on a separate plasmid, or integrated into the genome.

A visual genetic marker was utilized, wherein the loss of the adenine biosynthetic pathway in yeast was engineered by inserting premature stop codons into either ADE1 or ADE2 coding sequences. Wild type yeast colonies are normally white, but the loss of function of either ADE1 or ADE2 results in red yeast colonies when grown on media containing low amounts of adenine.

Editing in the test samples was induced for fixed periods of time by controlling the expression of the editing system with inducible promoters. After the editing period, the system was repressed to avoid unintended off-target mutations or interactions. Colonies derived from individuals of the induced population were grown and isolated, and the editing efficiency was determined by calculating the fraction of colonies that were ade- (as evidenced by red color). The targeted region was then sequenced in some of the ade- (red) colonies to determine the editing precision, which was expressed as the percentage of colonies that contained the correct edited sequence (as opposed to unintended deleterious insertions and deletions that also disrupted adenine biosynthesis). Editing efficiency is influenced by a number of factors, including the quality of the guide sequence, the quality of the donor sequence, the strength of the promoters used, and the length of time that editing is allowed to proceed.

Tables 1 and 2 present data from two separate experiments and show that a number of different gRNA-donor DNA pairs achieved high editing efficiency after 24 or 48 hours of editing. It should be noted that higher percentages of editing efficiency can be achieved by editing for longer durations.

To further show that physically tethering the guide RNA to the donor DNA sequence contributes to the high efficiency and fidelity observed with the CRISPR-retron system, the sequence of an autocatalytic self-cleaving ribozyme from the hepatitis delta virus (HDV) was introduced between the donor DNA sequence and gRNA of two constructs. Following transcription, the HDV ribozyme folded and cleaved the transcript in two, allowing the retron donor DNA and gRNA to act independently, as shown in FIG. 5. When the donor DNA and guide RNA were split by HDV, editing efficiency dropped to significantly lower levels (Table 1).

Table 3 shows the extremely high precision of editing. In total, 128 red colonies were sequenced from several gRNA-donor DNA strains, and all but one were perfect editing events (overall editing precision of 99.2%).

TABLE 1

Editing efficiency of different gRNA-donor DNA pairs after 24 hours of editing

| Strain ID | Description | # Red | # White | % Edited |
|---|---|---|---|---|
| 86 | tRNAp::ADE1 guide 2 donor DNA 1 | 155 | 7 | 95.7 |
| 87 | tRNAp::ADE1 guide 3 donor DNA 1 | 87 | 3 | 96.7 |
| 88 | tRNAp::ADE2 guide 3 donor DNA 1 | 228 | 38 | 85.7 |
| 89 | tRNAp::ADE2 guide 5 donor DNA 1 | 268 | 13 | 95.4 |
| 92 | pRPR1::ADE1 guide 2 donor DNA 1 | 170 | 13 | 92.9 |
| 93 | pRPR1::ADE1 guide 3 donor DNA 1 | 127 | 43 | 74.7 |
| 94 | pRPR1::ADE2 guide 3 donor DNA 1 | 58 | 202 | 22.3 |
| 95 | pRPR1::ADE2 guide 5 donor DNA 1 | 147 | 16 | 90.2 |
| 96 | pRPR1::ADE1 guide 2 donor DNA 1 HDV | 19 | 111 | 14.6 |
| 97 | pRPR1::ADE2 guide 3 donor DNA 1 HDV | 26 | 131 | 16.6 |

TABLE 2

Editing efficiency of different gRNA-donor DNA pairs under the control of different promoters after 48 hours of editing

| Strain ID | Description | # Red | # White | % Edited |
|---|---|---|---|---|
| 141 | pGAL7: HDV-ADE2 guide 3 donor1-HDV::tGAL7 | 434 | 32 | 93.1 |
| 142 | pTEF1: HDV-ADE2 guide 3 donor1-HDV::tGAL7 | 600 | 13 | 97.9 |
| 120 | pSNR52::HDV-ADE2 guide 3 donor1 | 720 | 4 | 99.4 |
| 141 | pGAL7: HDV-ADE2 guide 3 donor1-HDV::tGAL7 | 475 | 10 | 97.9 |
| 142 | pTEF1: HDV-ADE2 guide 3 donor1-HDV::tGAL7 | 557 | 7 | 98.8 |
| 120 | pSNR52::HDV-ADE2 guide 3 donor1 | 407 | 10 | 97.6 |

TABLE 3

Editing precision in several experiments

| Strain ID | # Perfect Edits | # Insertions/Deletions | % Perfect Edits |
|---|---|---|---|
| 86 | 32 | 0 | 100 |
| 87 | 16 | 0 | 100 |
| 92 | 15 | 1 | 93.75 |
| 93 | 16 | 0 | 100 |
| 120 | 24 | 0 | 100 |
| 141 | 24 | 0 | 100 |
| Total | 127 | 1 | 99.2 |

Example 2. Screening to Identify Causal Mutations Underlying Quantitative Trait Loci This example shows an example of how the CRISPR-retron system can be used to perform a high-throughput screen to identify causal mutations underlying quantitate trait loci (QTLs).

Introduction

Leveraging the known genetic diversity between two strains of *Saccharomyces cerevisiae*, RM11-1A and BY4742, the compositions and methods of the present invention can be used to perform a high-throughput screen to identify causal mutations underlying QTLs. Both genomes are fully sequenced and QTLs have previously been rough mapped for 46 traits. Between the two strains there are approximately 50,000 single nucleotide polymorphisms (SNPs) and small insertions/deletions, but it is expected that for any given trait, as few as 10-20 SNPs are responsible for the observed heritable phenotypic differences. In order to discover these causative SNPs and insertions/deletions, the haploid BY4742 strain can be screened and edited to change each SNP and small insertion/deletion to the corresponding RM11-1A allele. In this way, it is possible to compare each genetic change in an otherwise isogenic background and relate those changes to phenotypic output with the goal of identifying causal mutations that underlie the known QTLs.

Library Design and Generation

Figure 6:
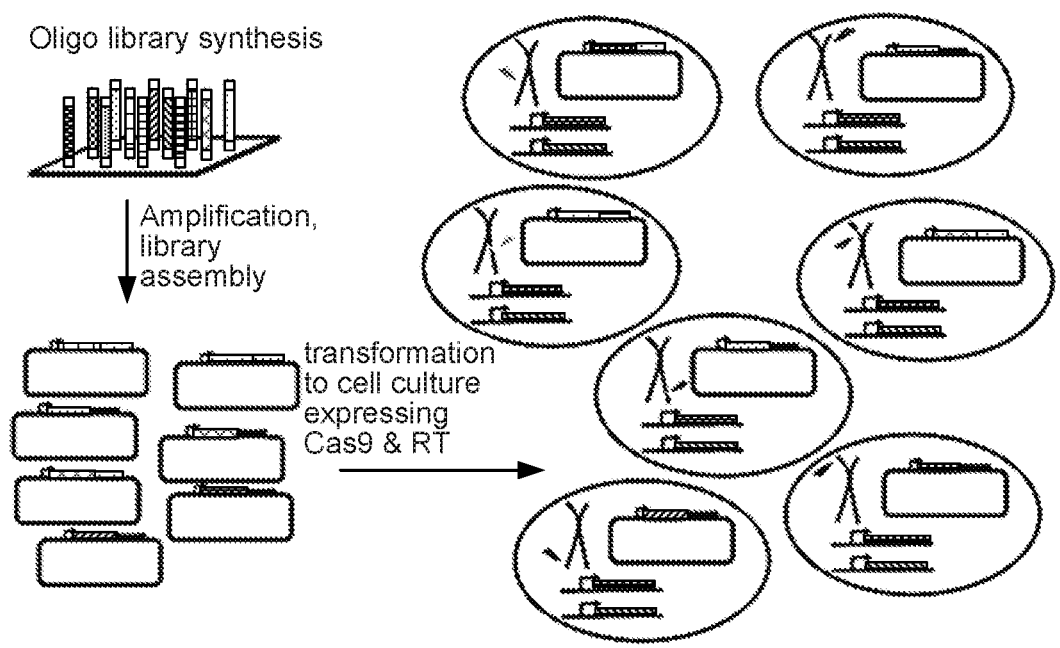
FIG. 6 shows a schematic of a procedure for oligonucleotide library preparation and screening. Oligonucleotide libraries can be synthesized in the format of an array, with a complexity ranging between 2,000 and 1,000,000 unique sequences. The oligonucleotide library can be amplified using common flanking primers that contain homology to the expression vector. The vector library can then be expanded, purified, and transformed into a yeast screening strain. The yeast screening strain may have Cas9 nuclease and reverse transcriptase integrated into the genome and expressed under the control of inducible promoters.

FIG. 6 shows a general diagram of the workflow. Once all guide RNA sequences that target editing positions of interest are identified, their predicted on-target efficiency can be scored, predicted off-target effects can be searched for, and the best guide sequences selected. Oligonucleotides (i.e., retron-gRNA cassettes) can then be designed for the library. An oligonucleotide can contain a 100 base pair donor DNA sequence comprising the desired edit, followed by 34 base pairs of constant structural sequence followed by a 20 base pair guide sequence. The 5' donor and 3' guide sequence can be flanked by invariant 20 base pair stretches of homology to the vector cloning site. Current technology allows pools with complexity of up to one million unique oligonucleotide sequences.

The oligonucleotide (i.e., retron-gRNA cassette) pool and expression vector can be independently PCR amplified using primers that overlap the oligonucleotide flanking sequence. Fragments can then be gel purified and cloned using Gibson assembly. The assembly can then subsequently be transformed into commercial high efficiency electrocompetent *E. coli*, followed by selection, bulking, and purification of the transformants. The resulting vector library can then be transformed into a yeast strain that contains an inducible Cas9 nuclease and reverse transcriptase that have been integrated into the genome. High transformation rates are essential to preserve uniform representation of oligonucleotides. Yeast that are transformed with the library can be selected for the presence of an auxotrophic marker on the expression plasmid, expanded, and stored in aliquots for future use as well as sequencing to determine the representation of oligonucleotides in the library. Next, editing can be induced for a fixed number of generations under conditions that induce the expression of the reverse transcriptase, Cas9 nuclease, and the gRNA. After the editing period, the CRISPR-retron system can be transcriptionally repressed to avoid confounding effects during screening. The edited culture can be aliquoted and stored for screening in multiple conditions as well as sequencing to determine the representation of oligonucleotides in the starting strain pool.

Screening

Samples from the edited yeast culture can be grown in conditions for which the RM11-1A and BY4742 strains possess known heritable differential growth phenotypes and known QTLs that control the different growth phenotypes. Some of the yeast will contain plasmids that direct the editing of mutations that confer increased or decreased growth rates, some of which are specific to the growth condition (i.e., causal SNPs that are responsible for the QTLs), resulting in yeast strains that increase or decrease in the population while the growth rate of the majority of the strains remains constant. After a fixed number of generations of competitive growth, the cultures can be harvested and the plasmids isolated. Finally, plasmids isolated from the cultures can be sequenced before and after the competition period, using the guide and donor sequences as a barcode to identify mutations that cause differential growth phenotypes.

Example 3. Large Donor Insertion Experiment

This example shows the efficacy of the CRISPR-retron system when provided with donors of considerable length. eGFP (720 bp) was inserted along with a fusion protein linker (45 bp) into the ADE1 locus of *S. cerevisiae*.

DESCRIPTION

When the ADE1 gene is disrupted, yeast cells no longer produce adenine, and colonies exhibit a pink color when grown on adenine-deficient media. Thus, editing efficiency can be easily measured by introducing a premature stop codon in the ADE1 gene (i.e., precisely 318 bp before the gene's stop codon, see, e.g., benchling.com/s/YcfW4YWP for a visual of the ADE1 genomic region).

For this experiment, a plasmid was developed with a donor comprised of (1) ADE1 homology arms, (2) a fusion protein linker, and (3) an eGFP coding sequence.

For (1), a donor/guide sequence previously used for proof-of-principle experiments was used. The ADE1 nonsense mutation was validated as being efficacious in simple knock-out experiments, where induction experiments indicated ~95% editing efficiency.

An AscI cloning site was inserted in the middle of the donor sequence. With this restriction site, additional sequences were easily inserted to lengthen the size of the donor. Once developed, the plasmid was cut, and additional sequence was appended to the retron.

In order to express GFP and conduct fluorescence assays, eGFP was knocked in in-frame with the ADE1 gene. To facilitate such an assay, a well-characterized fusion linker protein was included, which was placed directly upstream of the eGFP sequence.

Using PCR, the linker sequence was fused to the GFP sequence. 19-20 bp of homology was appended to the ADE1 gene on both ends of the linker-eGFP molecule, and the eGFP sequence provided the early stop codon necessary to induce the pink coloration in resultant yeast colonies.

Cloning was performed by means of Gibson assembly (New England Biolabs). Plasmid sequences were verified with Sanger sequencing (Elim Biopharmaceuticals). LiAc yeast transformation was conducted in triplicate (i.e., three different plasmid minipreps). Plating on dropout media was performed to select for plasmid-containing strains and single colonies were re-struck twice to isolate pure transformants.

Single colonies were inoculated overnight in "pre-induction" media (i.e., drop-out media containing 2% raffinose) and were allowed to shake in an incubator at 30° C. for 24 hours. This ensured that no editing occurred, as the retron system was driven by galactose promoters. The next step was to sub-culture 100 uL of saturated yeast culture into 3 mL of drop-out "induction" media (i.e., media containing 2% galactose) and incubate at 30° C. with shaking. After 24 hours, 100 uL was sub-cultured into 3 mL of fresh induction media. After another 24 hours, dilutions of induced yeast culture were placed on plates containing adenine-deficient drop-out media.

Plates were incubated at 30° C. After 48 hours, colonies were visible. Colonies were counted, and numbers are shown in Table 4 below.

TABLE 4

| | Editing efficiency | | |
|---|---|---|---|
| Plate | Red | White | % Red |
| 1 | 7 | 0 | 100 |
| 2 | 6 | 2 | 75 |
| 3 | 19 | 1 | 95 |

TABLE 4-continued

Editing efficiency

| Plate | Red | White | % Red |
|---|---|---|---|
| 4 | 17 | 3 | 85 |
| 5 | 17 | 1 | 94 |
| 6 | 10 | 0 | 100 |
| 7 | 12 | 1 | 92 |
| 8 | 14 | 1 | 93 |
| 9 | 4 | 0 | 100 |
| 10 | 8 | 0 | 100 |
| 11 | 10 | 2 | 83 |
| 12 | 3 | 0 | 100 |

Replicate 1: plates 1-4; Replicate 2: plates 5-8; Replicate 3: plates 9-12

Subsequently, 40 colonies were picked and genomic DNA was isolated (LiOAc/SDS method). Primers unique to the ADE1 locus were used in order to determine editing accuracy (namely, the fidelity of the reverse transcriptase).

```
                                          (SEQ ID NO: 1)
ADE1 forward primer:
CATTGGTGGCCAGAGGTAAAG (SEQ ID NO: 2)
ADE1 reverse primer:
GTGAGGAGTTACACTGGCGAC
```

PCR products were run on a 1.7% gel. Successful insertions were expected to have a size of 1.686 kB; all bands on the gel were approximately this size.

PCR products were column purified (ZYMO Research) and sent for Sanger sequencing with both primers that were used for PCR (Elim Biopharmaceuticals).

Sequencing data indicated that 38 of the 40 sequences had perfect donor insertions. Two strains had point mutations in the inserted eGFP sequences. Both were transversions (i.e., G->T).

The ADE1 gene sequence is set forth in SEQ ID NO:4. The guide sequence (located within the ADE1 sequence) is set forth in SEQ ID NO:3. The eGFP sequence is set forth in SEQ ID NO:5. The fusion linker protein sequence is set forth in SEQ ID NO:6. The ADE1 homology arms, which bound the donor sequence on the plasmid, included 50 bp of homology upstream (SEQ ID NO:7) and downstream (SEQ ID NO:9) of the edited site. The donor sequence, providing the premature stop codon, is set forth in SEQ ID NO:8.

Example 4. Efficient CRISPR-Assisted Single-Vector Yeast Editor (pEASY)

This example demonstrates the development of a vector containing all the necessary sequences for retron-mediated CRISPR/Cas9 yeast genome editing.

DESCRIPTION

Previously, quick editing experiments in yet untested yeast strains using the original iteration of the retron system were hampered by tedious integration experiments. The original iteration of the retron system utilized a reverse transcriptase (RT) and Cas9 integrated at the HIS3 locus of *S. cerevisiae*. Setting up a simple editing experiment in another yeast strain can take up to two weeks. By incorporating all components required for retron editing into one vector, the amount of time spent on simple editing experiments is significantly reduced (e.g. reduced to a single week).

For this experiment, a vector was developed that comprised the following components: (1) a reverse transcriptase (Ec86, optimized for *S. cerevisiae*) driven by the Gal10 promoter, (2) Cas9, driven by the Gal1 promoter, and (3) retron-associated sequences, driven by the Gal7 promoter. The vector contained a URA3 marker.

When the ADE2 gene is disrupted, yeast cells no longer produce adenine, and colonies exhibit a pink color when grown on adenine-deficient media. Thus, editing efficiency can easily be measured by using the retron system to introduce a premature stop codon in the ADE2 gene. In this experiment, a nonsense mutation was introduced 900 bp before the gene's stop codon (see: benchling.com/s/3j5lEbJQ for an annotated map of the ADE2 genomic region of *S. cerevisiae*, BY4742).

The donor and guide sequences that were utilized were used in previous proof-of-principle experiments. This ADE2 nonsense mutation was validated as being efficacious in knock-out experiments utilizing integrated RT/Cas9 sequences (under those conditions, ~95% editing efficiency was observed after 48 hours of induction). This same effective donor/guide combination was used for testing the efficacy of pEASY.

The vector was a total of 11,902 bp. Detailed sequence information and a map of pEASY can be found at benchling.com/s/seq-wm8PahEtuKsNjuNDkosR).

Cloning was performed by means of Gibson assembly (New England Biolabs). Vectors were prepared through the use of QIAprep Spin (Qiagen). Vector sequences were verified with Sanger sequencing (Elim Biopharmaceuticals).

Three *S. cerevisiae* strains were chosen for this pilot experiment: (1) RM11-la, (2) BY4716, and (3) strain, ZRS111 (simply, strain BY4742 with integrated RT/Cas9). The latter functioned as a positive control for this experiment.

LiAc heat-shock yeast transformations were performed, followed by plating on dropout media to select for vector-containing strains. This experiment was performed in duplicate for each condition (that is, two disparate vector isolates were transformed into each strain, for a total of six transformations). Single colonies were re-struck twice to isolate pure transformants.

Single colonies were inoculated overnight in "pre-induction" media (i.e., drop-out media containing 2% raffinose) and allowed to shake in an incubator at 30° C. for 24 hours. This ensured that no editing occurred, as the retron system was driven by galactose promoters, but allowed for a sufficiently saturated yeast culture, amenable to subsequent genomic perturbation.

100 uL of saturated yeast culture was sub-cultured into 3 mL of drop-out "induction" media (i.e., media containing 2% galactose) and incubated at 30° C. with shaking. After 24 hours, 100 uL was sub-cultured into 3 mL of fresh induction media. After another 24 hours, dilutions of induced yeast culture were placed onto plates containing adenine-deficient drop-out media.

Plates were incubated at 30° C. After 48 hours, colonies were visible. All plates showed >90% successfully edited (i.e., red) cells. Once this ADE2 assay validated the efficacy of this method, a version of the vector amenable to efficient cloning was developed. Inserting a unique restriction digest site (i.e., NotI) in place of the ADE2 donor/guide allows for a two-step cloning process that comprises: (1) digesting the pEASY vector, and (2) utilizing Gibson assembly to insert a GBLOCK containing a guide/donor sequence targeting a sequence of interest.

The ADE2 gene sequence is set forth in SEQ ID NO:10. The ADE2 homology arms, located 50 bp upstream and 48 bp downstream of the edit site, are set forth in SEQ ID NOS: 11 and 12, respectively. The guide sequence is set forth in SEQ ID NO: 13.

Example 5. Split Guide-Retron Editing

This example describes two experiments that demonstrated that the covalent link between the retron transcript and the guide RNA (gRNA) molecule is not required for the high editing efficiency of the CRISPR-retron system.

DESCRIPTION

Figure 7:
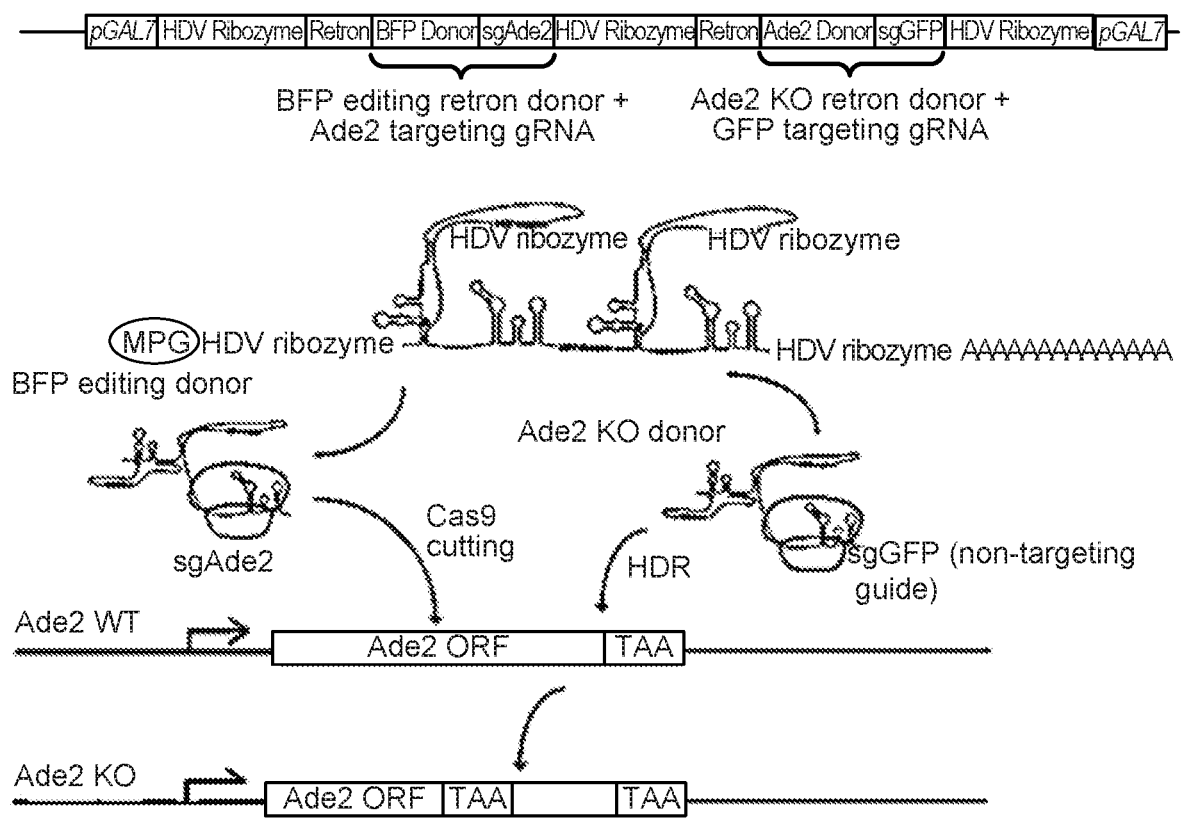
FIG. 7 shows a schematic for an experimental design involving unmatched retron-guide pairs.
Figure 8:
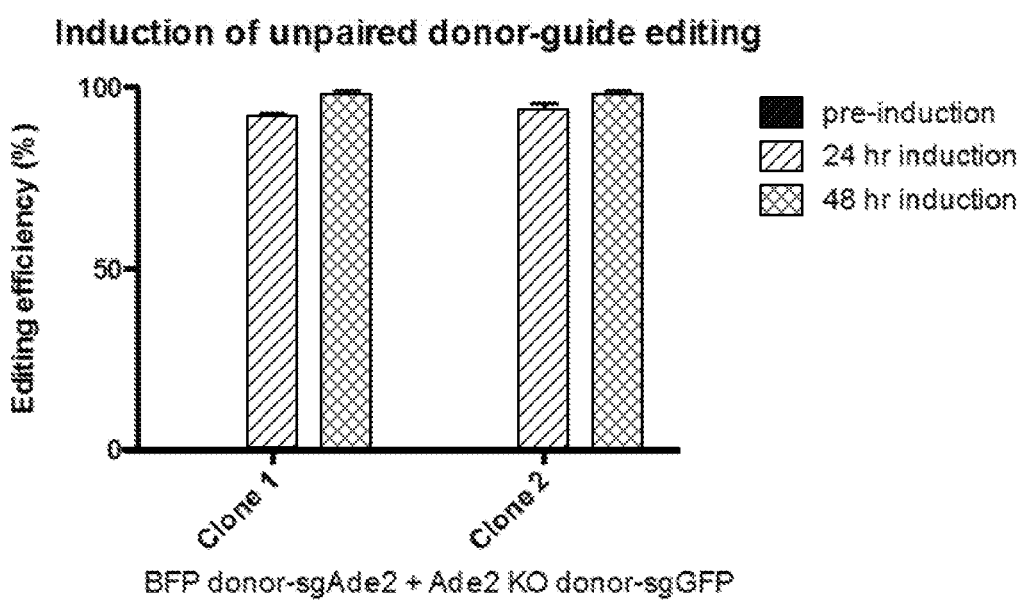
FIG. 8 shows the editing efficiency of the unmatched retron-guide at the ADE2 locus.

The first experiment involved inducible expression of two retron-guide units, separated post-transcriptionally by a self-cleaving hepatitis delta virus (HDV) ribozyme, as illustrated in FIG. 7. The first unit (FIG. 7, top, labeled "BFP Donor" and "sgAde2") consisted of a retron comprising a donor sequence for editing the gene encoding BFP (the BFP gene was not present in this strain, so this was a non-functional donor) and an sgAde2 gRNA coding region, which cleaved the ADE2 coding sequence. The second unit (FIG. 7, top, labeled "Ade2 Donor" and "sgGFP") had a retron comprising a donor sequence for repairing the cleavage by sgAde2 with a non-sense mutant allele at the ADE2 locus (Ade2 KO), while attached to a sgGFP gRNA coding region for targeting GFP (GFP was not present in this strain, so this was a non-functional gRNA). If a covalent link between the retron transcript and the gRNA molecule was required for the high editing efficiency of the retron-guide CRISPR-Cas9 system, high efficiency editing would not be expected when the Ade2 KO retron was not attached to sgAde2 in cis. If cis association was not required for high editing efficiency, the sgAde2 guide RNA and msDNA generated from the Ade2 KO retron transcript would act in trans to facilitate gDNA cleavage and homology-directed repair (HDR) (FIG. 7, bottom schematic). FIG. 8 shows that ADE2 locus knockout efficiency was >90% by 24 hours in two separate yeast clone replicates, indicating that cis association of matching retron transcript and gRNA for the same locus was not required.

Figure 9:
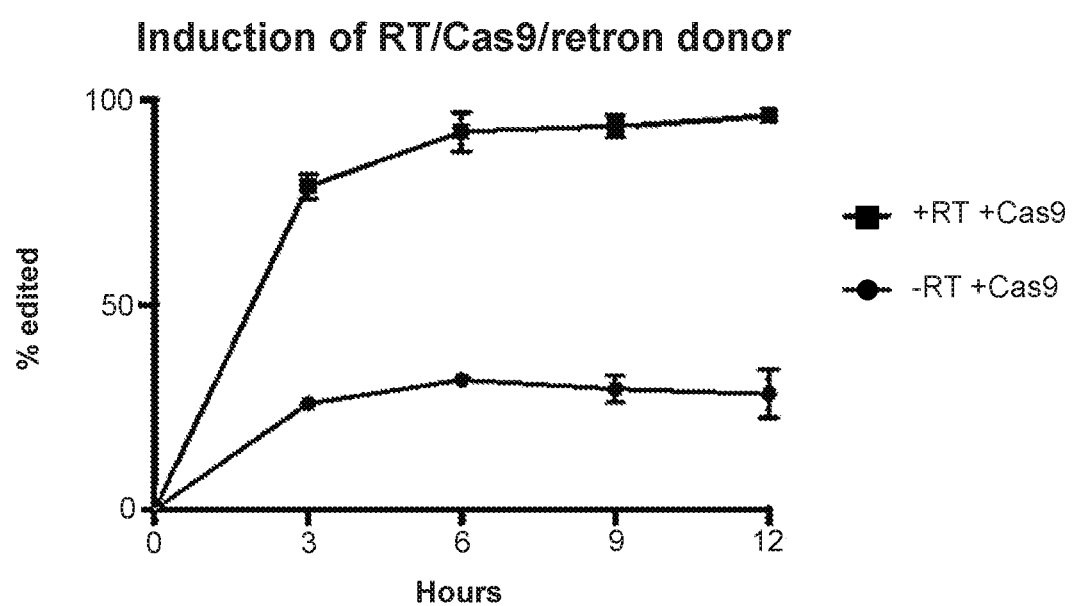
FIG. 9 shows the editing efficiency of the retron-guide editing components in trans at the ADE2 locus.

The second experiment involved constitutive expression of the sgAde2 gRNA from a high-copy plasmid. This plasmid also contained a 100 bp Ade2 KO donor sequence without a retron sequence. A second plasmid was added to the yeast, containing a retron-guide pair identical to the Ade2 KO retron-sgGFP pair in the first experiment. Since the sgAde2 gRNA and Ade2 KO retron donor were expressed on different plasmids, they did not associate in cis. FIG. 9 shows that in the absence of the bacterial reverse transcriptase (RT), the Ade2 KO retron transcript was not reverse transcribed and thus editing efficiency was at 30%~40%. In the presence of RT, editing efficiency was high due to expression of the Ade2 KO msDNA donor for HDR by reverse transcription. Thus, it was concluded that the retron transcript and the gRNA components of the editing system can act in trans to achieve high editing efficiency.

VI. Exemplary Embodiments

Exemplary embodiments provided in accordance with the presently disclosed subject matter include, but are not limited to, the claims and the following embodiments:

1. A retron-guide RNA cassette comprising:
(a) a retron comprising:
(i) an msr locus;
(ii) a first inverted repeat sequence coding region;
(iii) an msd locus;
(iv) a donor DNA sequence located within the msd locus; and
(v) a second inverted repeat sequence coding region; and
(b) a guide RNA (gRNA) coding region.
2. The cassette of embodiment 1, wherein the first inverted repeat sequence coding region is located within the 5' end of the msr locus.
3. The cassette of embodiment 1 or 2, wherein the second inverted repeat sequence coding region is located 3' of the msd locus.
4. The cassette of any one of embodiments 1 to 3, wherein the retron encodes an RNA molecule that is capable of self-priming reverse transcription by a reverse transcriptase (RT).
5. The cassette of embodiment 4, wherein reverse transcription of the RNA molecule results in a multicopy single-stranded DNA (msDNA) molecule that comprises RNA and DNA.
6. The cassette of any one of embodiments 1 to 5, wherein transcription products of the retron and the gRNA coding region are physically coupled.
7. The cassette of any one of embodiments 1 to 5, wherein transcription products of the retron and the gRNA coding region are not physically coupled.
8. The cassette of any one of embodiments 1 to 7, wherein the gRNA coding region is 3' of the retron.
9. The cassette of any one of embodiments 1 to 7, wherein the gRNA coding region is 5' of the retron.
10. The cassette of any one of embodiments 1 to 9, further comprising a ribozyme sequence.
11. The cassette of embodiment 10, wherein the ribozyme sequence encodes a hepatitis delta virus ribozyme.
12. The cassette of any one of embodiments 1 to 11, wherein the cassette is less than 200 nucleotides in length.
13. The cassette of any one of embodiments 1 to 12, wherein the donor DNA sequence comprises two homology arms, wherein each homology arm has at least about 70% to about 99% similarity to a portion of the sequence of a genetic locus of interest on either side of a nuclease cleavage site.
14. A vector comprising the cassette of any of one embodiments 1 to 13.
15. The vector of embodiment 14, further comprising a promoter that is operably linked to the cassette.
16. The vector of embodiment 15, wherein the promoter is inducible.
17. The vector of embodiment 15 or 16, wherein the promoter is selected from the group consisting of an RNA polymerase II promoter, an RNA polymerase III promoter, and a combination thereof.
18. The vector of any one of embodiments 14 to 17, further comprising a reverse transcriptase (RT) coding sequence.
19. The vector of embodiment 18, further comprising a nuclear localizing sequence located 5' of the RT coding sequence.
20. The vector of any one of embodiments 14 to 19, further comprising a nuclease coding sequence.

21. The vector of embodiment 20, wherein the nuclease encoded by the nuclease coding sequence is selected from the group consisting of Cas9, Cpf1, and a combination thereof.

22. A retron donor DNA-guide molecule comprising:
(a) a retron transcript comprising:
(i) an msr region;
(ii) a first inverted repeat sequence;
(iii) an msd region;
(iv) a donor DNA sequence coding region located within the msd region; and
(v) a second inverted repeat sequence; and
(b) a guide RNA (gRNA) molecule.

23. The retron donor DNA-guide molecule of embodiment 22, wherein the first inverted repeat sequence is located within the 5' end of the msr region.

24. The retron donor DNA-guide molecule of embodiment 22 or 23, wherein the second inverted repeat sequence is located 3' of the msd region.

25. The retron donor DNA-guide molecule of any one of embodiments 22 to 24, wherein the retron transcript is capable of self-priming reverse transcription by a reverse transcriptase (RT).

26. The retron donor DNA-guide molecule of any one of embodiments 22 to 25, wherein the retron transcript and the gRNA molecule are physically coupled.

27. The retron donor DNA-guide molecule of embodiment 26, wherein the gRNA molecule is 3' of the retron transcript.

28. The retron donor DNA-guide molecule of embodiment 26, wherein the gRNA molecule is 5' of the retron transcript.

29. The retron donor DNA-guide molecule of any one of embodiments 22 to 28, further comprising a ribozyme.

30. The retron donor DNA-guide molecule of embodiment 29, wherein the ribozyme is a hepatitis delta virus ribozyme.

31. The retron donor DNA-guide molecule of any one of embodiments 22 to 30, wherein the retron transcript and the gRNA molecule are physically uncoupled after transcription.

32. The retron donor DNA-guide molecule of any one of embodiments 22 to 31, wherein reverse transcription of the retron transcript results in a multicopy single-stranded DNA (msDNA) molecule that comprises RNA and DNA.

33. The retron donor DNA-guide molecule of embodiment 32, wherein at least some of the RNA content of the msDNA molecule is degraded.

34. The retron donor DNA-guide molecule of any one of embodiments 22 to 33, wherein the donor DNA sequence coding region comprises sequences encoding two homology arms, wherein each homology arm has at least about 70% to about 99% similarity to a portion of the sequence of a genetic locus of interest on either side of a nuclease cleavage site.

35. A method for modifying one or more target nucleic acids of interest at one or more target loci within a genome of a host cell, the method comprising:
(a) transforming the host cell with a vector of any one of embodiments 14 to 21; and
(b) culturing the host cell or transformed progeny of the host cell under conditions sufficient for expressing from the vector a retron donor DNA-guide molecule comprising a retron transcript and a guide RNA (gRNA) molecule, wherein the retron transcript self-primes reverse transcription by a reverse transcriptase (RT) expressed by the host cell or the transformed progeny of the host cell, wherein at least a portion of the retron transcript is reverse transcribed to produce a multicopy single-stranded DNA (msDNA) molecule having one or more donor DNA sequences,
wherein the one or more donor DNA sequences are homologous to the one or more target loci and comprise sequence modifications compared to the one or more target nucleic acids,
wherein the one or more target loci are cut by a nuclease expressed by the host cell or transformed progeny of the host cell, wherein the site of nuclease cutting is specified by the gRNA, and
wherein the one or more donor DNA sequences recombine with the one or more target nucleic acid sequences to insert, delete, and/or substitute one or more bases of the sequence of the one or more target nucleic acid sequences to induce one or more sequence modifications at the one or more target loci within the genome.

36. The method of embodiment 35, wherein the msr and msd regions of the retron transcript form a secondary structure, wherein the formation of the secondary structure is facilitated by base pairing between the first and second inverted repeat sequences, and wherein the secondary structure is recognized by the RT for the initiation of reverse transcription.

37. The method of embodiment 35 or 36, wherein the host cell is capable of expressing the RT prior to transforming the host cell with the vector.

38. The method of embodiment 37, wherein the RT is encoded in a sequence integrated into the host cell genome or on a separate plasmid.

39. The method of embodiment 35 or 36, wherein the host cell is capable of expressing the RT at the same time as, or after, transforming the host cell with the vector.

40. The method of embodiment 39, wherein the RT is expressed from the vector or a separate plasmid.

41. The method of any one of embodiments 35 to 40, wherein the host cell is capable of expressing the nuclease prior to transforming the host cell with the vector.

42. The method of embodiment 41, wherein the nuclease is encoded in a sequence integrated into the host cell genome or on a separate plasmid.

43. The method of any one of embodiments 35 to 40, wherein the host cell is capable of expressing the nuclease at the same time as, or after, transforming the host cell with the vector.

44. The method of embodiment 43, wherein the nuclease is expressed from the vector or a separate plasmid.

45. The method of any one of embodiments 35 to 44, wherein the nuclease is selected from the group consisting of Cas9, Cpf1, and a combination thereof.

46. The method of any one of embodiments 35 to 45, wherein the gRNA molecule and the one or more donor DNA sequences are physically coupled.

47. The method of any one of embodiments 35 to 45, wherein the gRNA molecule and the one or more donor DNA sequences are not physically coupled.

48. The method of any one of embodiments 35 to 47, wherein the one or more donor DNA sequences comprise two homology arms, wherein each homology arm has at least about 70% to about 99% similarity to a portion of the sequence of the one or more target loci on either side of a nuclease cleavage site.

49. The method of any one of embodiments 35 to 48, wherein the host cell is a prokaryotic cell.

50. The method of any one of embodiments 35 to 48, wherein the host cell is a eukaryotic cell.

51. The method of embodiment 50, wherein the eukaryotic cell is a yeast cell.

52. The method of any one of embodiments 35 to 51, wherein about ten or more target loci are modified.

53. The method of any one of embodiments 35 to 52, wherein the host cell comprises a population of host cells.

54. The method of embodiment 53, wherein the one or more sequence modifications are induced in greater than about 90% of the population of host cells.

55. The method of embodiment 53, wherein the one or more sequence modifications are induced in greater than about 95% of the population of host cells.

56. The method of any one of embodiments 35 to 55, wherein inducing the one or more sequence modifications results in the insertion of one or more sequences encoding cellular localization tags, one or more sequences encoding degrons, one or more synthetic response elements, or a combination thereof into the genome.

57. The method of any one of embodiments 35 to 56, wherein inducing the one or more sequence modifications results in the insertion of one or more sequences from a heterologous genome.

58. A method for screening one or more genetic loci of interest in a genome of a host cell, the method comprising:
(a) modifying one or more target nucleic acids of interest at one or more target loci within the genome of the host cell according to the method of any one of embodiments 35 to 57;
(b) incubating the modified host cell under conditions sufficient to elicit a phenotype that is controlled by the one or more genetic loci of interest;
(c) identifying the resulting phenotype of the modified host cell; and
(d) determining that the identified phenotype was the result of the modifications made to the one or more target nucleic acids of interest at the one or more target loci of interest.

59. The method of embodiment 58, wherein two or more vectors are used.

60. The method of embodiment 58 or 59, wherein at least 1,000 to 1,000,000 genetic loci of interest are screened simultaneously.

61. The method of any one of embodiments 58 to 60, wherein the phenotype is identified using a reporter.

62. The method of embodiment 61, wherein the reporter is selected from the group consisting of a fluorescent tagged protein, an antibody, a chemical stain, a chemical indicator, and a combination thereof.

63. The method of embodiment 61 or 62, wherein the reporter responds to the concentration of a metabolic product, a protein product, a synthesized drug of interest, a cellular phenotype of interest, or a combination thereof.

64. A host cell that has been transformed by a vector of any one of embodiments 14 to 21.

65. A pharmaceutical composition comprising:
(a) the retron-guide RNA cassette of any one of embodiments 1 to 13, the vector of any one of embodiments 14 to 21, the retron donor-DNA guide molecule of any one of embodiments 22 to 34, or a combination thereof; and
(b) a pharmaceutically acceptable carrier.

66. A method for preventing or treating a genetic disease in a subject, the method comprising administering to the subject an effective amount of the pharmaceutical composition of embodiment 65 to correct a mutation in a target gene associated with the genetic disease.

67. The method of embodiment 66, wherein the genetic disease is selected from the group consisting of X-linked severe combined immune deficiency, sickle cell anemia, thalassemia, hemophilia, neoplasia, cancer, age-related macular degeneration, schizophrenia, trinucleotide repeat disorders, fragile X syndrome, prion-related disorders, amyotrophic lateral sclerosis, drug addiction, autism, Alzheimer's disease, Parkinson's disease, cystic fibrosis, blood and coagulation diseases and disorders, inflammation, immune-related diseases and disorders, metabolic diseases and disorders, liver diseases and disorders, kidney diseases and disorders, muscular/skeletal diseases and disorders, neurological and neuronal diseases and disorders, cardiovascular diseases and disorders, pulmonary diseases and disorders, ocular diseases and disorders, and a combination thereof.

68. A kit for modifying one or more target nucleic acids of interest at one or more target loci within a genome of a host cell, the kit comprising one or a plurality of vectors of any one of embodiments 14 to 21.

69. The kit of embodiment 68, further comprising a host cell.

70. The kit of embodiment 68 or 69, further comprising one or more reagents for transforming the host cell with the one or plurality of vectors, one or more reagents for inducing expression of the one or plurality of vectors, or a combination thereof.

71. The kit of any one of embodiments 68 to 70, further comprising a reverse transcriptase or a plasmid for expressing a reverse transcriptase.

72. The kit of any one of embodiments 68 to 71, further comprising a nuclease or a plasmid for expressing a nuclease.

73. The kit of any one of embodiments 68 to 72, further comprising instructions for transforming the host cell, inducing expression of the vector, inducing expression of the reverse transcriptase, inducing expression of the nuclease, or a combination thereof.

74. A kit for modifying one or more target nucleic acids of interest at one or more target loci within a genome of a host cell, the kit comprising one or a plurality of retron donor DNA-guide molecules of any one of embodiments 22 to 34.

75. The kit of embodiment 74, further comprising a host cell.

76. The kit of embodiment 74 or 75, further comprising one or more reagents for introducing the one or plurality of retron donor DNA-guide molecules into the host cell.

77. The kit of any one of embodiments 74 to 76, further comprising a reverse transcriptase or a plasmid for expressing a reverse transcriptase.

78. The kit of any one of embodiments 74 to 77, further comprising a nuclease or a plasmid for expressing a nuclease.

79. The kit of any one of embodiments 74 to 78, further comprising instructions for introducing the one or plurality of retron donor DNA-guide molecules into the host cell, inducing expression of the reverse transcriptase, inducing expression of the nuclease, or a combination thereof.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

| INFORMAL SEQUENCE LISTING | | |
|---|---|---|
| SEQ ID NO: | Sequence | Description |
| 1 | CATTGGTGGCCAGAGGTAAAG | ADE1 forward primer |
| 2 | GTGAGGAGTTACACTGGCGAC | ADE1 reverse primer |
| 3 | CAAGTGCAAAGATTATGCTA | ADE1 guide sequence (20 bp) |
| 4 | ATGTCAATTACGAAGACTGAACTGGACGGTATATTGCCATTGGTGGCCAGAGGTAAAGTTAGAGACATATATGAGGTAGACGCTGGTACGTTGCTGTTTGTTGCTACGGATCGTATCTCTGCATATGACGTTATTATGGAAAACAGCATTCCTGAAAAGGGGATCCTATTGACCAAACTGTCAGAGTTCTGGTTCAAGTTCCTGTCCAACGATGTTCGTAATCATTTGGTCGACATCGCCCCAGGTAAGACTATTTTCGATTATCTACCTGCAAAATTGAGCGAACCAAAGTACAAAACGCAACTAGAAGACCGCTCTCTATTGGTTCACAAACATAAACTAATTCCATTGGAAGTAATTGTCAGAGGCTACATCACCGGATCTGCTTGGAAAGAGTACGTAAAAACAGGTACTGTGCATGGTTTGAAACAACCTCAAGGACTTAAAGAATCTCAAGAGTTCCCAGAACCAATCTTCACCCCATCGACCAAGGCTGAACAAGGTGAACATGACGAAAACATCTCTCCTGCCCAGGCCGCTGAGCTGGTGGGTGAAGATTTGTCACGTAGAGTGGCAGAACTGGCTGTAAAACTGTACTCCAAGTGCAAAGATTATGCTAAGGAGAAGGGCATCATCATCGCAGACACTAAATTCGAATTCGGTATTGACGAAAAGACCAATGAAATTATTCTAGTGGACGAGGTGCTAACGCCAGACTCCTCTAGATTCTGGAACGGTGCCTCTTATAAGGTAGGAGAATCCCAAGATTCTTACGATAAGCAATTTTTAAGAGACTGGCTTACTGCTAATAAGTTGAACGGTGTTAACGGCGTCAAAATGCCCCAAGACATTGTCGACAGGACAAGGGCCAAATATATAGAGGCTTATGAAACATTGACAGGGTCTAAATGGTCTCACTAA | ADE1 sequence (921 bp) (guide sequence bold and underlined) |
| 5 | ATGGTGAGCAAGGGCGAGGAGCTGTTCACCGGGGTGGTGCCCATCCTGGTCGAGCTGGACGGCGACGTAAACGGCCACAAGTTCAGCGTGTCCGGCGAGGGCGAGGGCGATGCCACCTACGGCAAGCTGACCCTGAAGTTCATCTGCACCACCGGCAAGCTGCCCGTGCCCTGGCCCACCCTCGTGACCACCCTGACCTACGGCGTGCAGTGCTTCAGCCGCTACCCCGACCACATGAAGCAGCACGACTTCTTCAAGTCCGCCATGCCCGAAGGCTACGTCCAGGAGCGCACCATCTTCTTCAAGGACGACGGCAACTACAAGACCCGCGCCGAGGTGAAGTTCGAGGGCGACACCCTGGTGAACCGCATCGAGCTGAAGGGCATCGACTTCAAGGAGGACGGCAACATCCTGGGGCACAAGCTGGAGTACAACTACAACAGCCACAACGTCTATATCATGGCCGACAAGCAGAAGAACGGCATCAAGGTGAACTTCAAGATCCGCCACAACATCGAGGACGGCAGCGTGCAGCTCGCCGACCACTACCAGCAGAACACCCCCATCGGCGACGGCCCCGTGCTGCTGCCCGACAACCACTACCTGAGCACCCAGTCCGCCCTGAGCAAAGACCCCAACGAGAAGCGCGATCACATGGTCCTGCTGGAGTTCGTGACCGCCGCCGGGATCACTCTCGGCATGGACGAGCTGTACAAGTAA | eGFP sequence (720 bp) |
| 6 | GGTGGAGGAGGCTCTGGTGGAGGCGGTAGCGGAGGCGGAGGGTCG | Fusion linker sequence (45 bp) |
| 7 | TAGAGTGGCAGAACTGGCTGTAAAACTGTACTCCAAGTGCAAAGATTATG | ADE1 homology arm (50 bp of homology, upstream of edited site) |
| 8 | GTTCACACTCACTAGAGTGACGAACAATACACGTTAGC | Donor sequence (premature stop codon bold and underlined) |
| 9 | CTAAGGAGAAGGGCATCATCATCGCAGACACTAAATTCGAATTCGGTATT | ADE1 homology arm (50 bp of homology, downstream of edited site) |

INFORMAL SEQUENCE LISTING

| SEQ ID NO: | Sequence | Description |
|---|---|---|
| 10 | ATGGATTCTAGAACAGTTGGTATATTAGGAGGGGGACAATTG GGACGTATGATTGTTGAGGCAGCAAACAGGCTCAACATTAAG ACGGTAATACTAGATGCTGAAAATTCTCCTGCCAAACAAATA AGCAACTCCAATGACCACGTTAATGGCTCCTTTTCCAATCCTC TTGATATCGAAAAACTAGCTGAAAAATGTGATGTGCTAACGA TTGAGATTGAGCATGTTGATGTTCCTACACTAAAGAATCTTCA AGTAAAACATCCCAAATTAAAAATTTACCCTTCTCCAGAAAC AATCAGATTGATACAAGACAAATATATTCAAAAGAGCATTT AATCAAAAATGGTATAGCAGTTACCCAAAGTGTTCCTGTGGA ACAAGCCAGTGAGACGTCCCTATTGAATGTTGGAAGAGATTT GGGTTTTCCATTCGTCTTGAAGTCGAGGACTTTGGCATACGAT GGAAGAGGTAACTTCGTTGTAAAGAATAAGGAAATGATTCCG GAAGCTTTGGAAGTACTGAAGGATCGTCCTTTGTACGCCGAA AAATGGGCACCATTTACTAAAGAATTAGCAGTCATGATTGTG AGATCTGTTAACGGTTTAGTGTTTTCTTACCCAATTGTAGAGA CTATCCACAAGGACAATATTTGTGACTTATGTTATGCGCCTGC TAGAGTTCCGGACTCCGTTCAACTTAAGGCGAAGTTGTTGGC AGAAAATGCAATCAAATCTTTTCCCGGTTGTGGTATATTTGGT GTGGAAATGTTCTATTTAGAAACAGGGGAATTGCTTATTAAC GAAATTGCCCCAAGGCCTCACAACTCTGGACATTATACCATT GATGCTTGCGTCACTTCTCAATTTGAAGCTCATTTGAGATCAA TATTGGATTTGCCAATGCCAAAGAATTTCACATCTTTCTCCAC CATTACAACGAACGCCATTATGCTAAATGTTCTTGGAGACAA ACATACAAAAGATAAAGAGCTAGAAACTTGCGAAAGAGCAT TGGCGACTCCAGGTTCCTCAGTGTACTTATATGGAAAAGAGT CTAGACCTAACAGAAAAGTAGGTCACATAAATATTATTGCCT CCAGTATGGCGGAATGTGAACAAAGGCTGAACTACATTACAG GTAGAACTGATATTCCAATCAAAATCTCTGTCGCTCAAAAGT TGGACTTGGAAGCAATGGTCAAACCATTGGTTGGAATCATCA TGGGATCAGACTCTGACTTGCCGGTAATGTCTGCCGCATGTG CGGTTTTAAAAGATTTTGGCGTTCCATTTGAAGTGACAATAGT CTCTGCTCATAGAACTCCACATAGGATGTCAGCATATGCTATT TCCGCAAGCAAGCGTGGAATTAAAACAATTATCGCTGGAGCT GGTGGGGCTGCTCACTTGCCAGGTATGGTGGCTGCAATGACA CCACTTCCTGTCATCGGTGTGCCCGTAAAAGGTTCTTGTCTAG ATGGAGTAGATTCTTTACATTCAATTGTGCAAATGCCTAGAG GTGTTCCAGTAGCTACCGTCGCTATTAATAATAGTACGAACG CTGCGCTGTTGGCTGTCAGACTGCTTGGCGCTTATGATTCAAG TTATACAACGAAAATGGAACAGTTTTTATTAAAGCAAGAAGA AGAAGTTCTTGTCAAAGCACAAAAGTTAGAAACTGTCGGTTA CGAAGCTTATCTAGAAAACAAGTAA | ADE2 sequence (1,716 bp) (codon to be edited bold and underlined) |
| 11 | TGGAAATGTTCTATTTAGAAACAGGGGAATTGCTTATTAACG AAATTGCC | ADE2 homology arm (50 bp upstream of edit) |
| 12 | TGAAGGCCTCACAACTCTGGACATTATACCATTGATGCTTGC GTCACTTC | ADE2 homology arm (48 bp downstream of edit (edit shown in bold and underline)) |
| 13 | ATTAACGAAATTGCCCCA | Guide 3 0.74 (18 bp) |
| 14 | TAACTATGATAAGATTCCGTATGCGCACCCTTAGCGAGAGGT TTATCATTAAGGTCAACCTCTGGATGTTGTTTCGGCATCCTGC ATTGAATCTGAGTTACTGTCTGTTTTCCTTGTTGGAACGGAGA GCATCGCCTGATGCTCTCCGAGCCAACCAGGAAACCCGTTTT TTCTGACGTAAGGGTGCGCAACTTTCATGAAATCCGCTGAAT ATTTGAACACTTTTAGATTGAGAAATCTCGGCCTACCTGTCAT GAACAATTTGCATGACATGTCTAAGGCGACTCGCATATCTGT TGAAACACTTCGGTTGTTAATCTATACAGCTGATTTTCGCTAT AGGATCTACACTGTAGAAAAGAAAGGCCCAGAGAAGAGAAT GAGAACCATTTACCAACCTTCTCGAGAACTTAAAGCCTTACA AGGATGGGTTCTACGTAACATTTTAGATAAACTGTCGTCATCT CCTTTTTCTATTGGATTTGAAAAGCACCAATCTATTTTGAATA ATGCTACCCCGCATATTGGGGCAAACTTTATACTGAATATTG | Retron Ec86 sequence |

INFORMAL SEQUENCE LISTING

| SEQ ID NO: | Sequence | Description |
|---|---|---|
| | ATTTGGAGGATTTTTTCCCAAGTTTAACTGCTAACAAAGTTTT<br>TGGAGTGTTCCATTCTCTTGGTTATAATCGACTAATATCTTCA<br>GTTTTGACAAAAATATGTTGTTATAAAAATCTGCTACCACAA<br>GGTGCTCCATCATCACCTAAATTAGCTAATCTAATATGTTCTA<br>AACTTGATTATCGTATTCAGGGTTATGCAGGTAGTCGGGGCTT<br>GATATATACGAGATATGCCGATGATCTCACCTTATCTGCACA<br>GTCTATGAAAAAGGTTGTTAAAGCACGTGATTTTTTATTTTCT<br>ATAATCCCAAGTGAAGGATTGGTTATTAACTCAAAAAAAACT<br>TGTATTAGTGGGCCTCGTAGTCAGAGGAAAGTTACAGGTTTA<br>GTTATTTCACAAGAGAAAGTTGGGATAGGTAGAGAAAAATAT<br>AAAGAAATTAGAGCAAAGATACATCATATATTTTGCGGTAAG<br>TCTTCTGAGATAGAACACGTTAGGGGATGGTTGTCATTTATTT<br>TAAGTGTGGATTCAAAAAGCCATAGGAGATTAATAACTTATA<br>TTAGCAAATTAGAAAAAAAATATGGAAAGAACCCTTTAAATA<br>AAGCGAAGACCTAATGGTCTTCGTTTTAAAACTAAAGCTCAT<br>AGGTTGAAAAATTGAGCACTTCTTCGTCCAACCAGTTATTTAG<br>TTCCTGCAATCGTTTCTGCAGGGGCATCAATTCGTTTCTTACG<br>AATACCTTGCTAGCCTTCTCCACATCCCCAAACCCCCCGACAT<br>TATTAGGCATAATTCCCATCAT | |
| 15 | TAACTATGATAAGATTCCGT | Plasmid start sequence (5' of msr locus) |
| 16 | TGCGCACCCTTA | Inverted repeat sequence |
| 17 | TAAGGGTGCGCA | Second inverted repeat |
| 18 | ATGCGCACCCTTAGCGAGAGGTTTATCATTAAGGTCAACCTC<br>TGGATGTTGTTTCGGCATCCTGCATTGAATCTGAGTTACT | msr locus |
| 19 | TCTGAGTTACTGTCTGTTTTCCTTGTTGGAACGGAGAGCATCG<br>CCTGATGCTCTCCGAGCCAACCAGGAAACCCGTTTTTTCTGAC | msd locus |
| 20 | TGTTGGAACGGAGAGCATCGCCTGATGCTCTCCGAGCCAAC | Replaceable region |
| 21 | ATGAAATCCGCTGAATATTTGAACACTTTTAGATTGAGAAAT<br>CTCGGCCTACCTGTCATGAACAATTTGCATGACATGTCTAAG<br>GCGACTCGCATATCTGTTGAAACACTTCGGTTGTTAATCTATA<br>CAGCTGATTTTCGCTATAGGATCTACACTGTAGAAAAGAAAG<br>GCCCAGAGAAGAGAATGAGAACCATTTACCAACCTTCTCGAG<br>AACTTAAAGCCTTACAAGGATGGGTTCTACGTAACATTTTAG<br>ATAAACTGTCGTCATCTCCTTTTTCTATTGGATTTGAAAAGCA<br>CCAATCTATTTTGAATAATGCTACCCCGCATATTGGGGCAAA<br>CTTTATACTGAATATTGATTTGGAGGATTTTTTCCCAAGTTTA<br>ACTGCTAACAAAGTTTTTGGAGTGTTCCATTCTCTTGGTTATA<br>ATCGACTAATATCTTCAGTTTTGACAAAAATATGTTGTTATAA<br>AAATCTGCTACCACAAGGTGCTCCATCATCACCTAAATTAGC<br>TAATCTAATATGTTCTAAACTTGATTATCGTATTCAGGGTTAT<br>GCAGGTAGTCGGGGCTTGATATATACGAGATATGCCGATGAT<br>CTCACCTTATCTGCACAGTCTATGAAAAAGGTTGTTAAAGCA<br>CGTGATTTTTTATTTTCTATAATCCCAAGTGAAGGATTGGTTA<br>TTAACTCAAAAAAAACTTGTATTAGTGGGCCTCGTAGTCAGA<br>GGAAAGTTACAGGTTTAGTTATTTCACAAGAGAAAGTTGGGA<br>TAGGTAGAGAAAATATAAAGAAATTAGAGCAAAGATACAT<br>CATATATTTTGCGGTAAGTCTTCTGAGATAGAACACGTTAGG<br>GGATGGTTGTCATTTATTTTAAGTGTGGATTCAAAAAGCCATA<br>GGAGATTAATAACTTATATTAGCAAATTAGAAAAAAAATATG<br>GAAAGAACCCTTTAAATAAAGCGAAGACCTAA | Ec86 reverse transcriptase (optimized) |
| 22 | ACTTTC | Sequence between second inverted repeat sequence and Ec86 reverse transcriptase sequence |

-continued

| INFORMAL SEQUENCE LISTING | | |
|---|---|---|
| SEQ ID NO: | Sequence | Description |
| 23 | TGGTCTTCGTTTTAAAACTAAAGCTCATAGGTTGAAAAATTG AGCACTTCTTCGTCCAACCAGTTATTTAGTTCCTGCAATCGTT TCTGCAGGGGCATCAATTCGTTTCTTACGAATACCTTGCTAGC CTTCTCCACATCCCCAAACCCCCCGACATTATTAGGCATAATT CCCATCAT | Sequence located 3' of EC86 reverse transcriptase sequence |
| 24 | GTTCCTGGCCTTTTGCTGGCCTTTTGCTCTTAATTAAGTATATG TGTTATGTAGTATACTCTTTCTTCAACAATTAAATACTCTCGG TAGCCAAGTTGGTTTAAGGCGCAAGACTGTAATTTATCACTA CGAAATCTTGAGATCGGGCGTTCGACTCGCCCCCGGGAGAGA TGGCCGGCATGGTCCCAGCCTCCTCGCTGGCGCCGGCTGGGC AACACCTTCGGGTGGCGAATGGGACTTTATGCGCACCCTTAG CGAGAGGTTTATCATTAAGGTCAACCTCTGGATGTTGTTTCGG CATCCTGCATTGAATCTGAGTTACTGTCTGTTTTCCTCTCTGA CAATTACTTCCAATGGAATTAGTTTATGTTTGTGAACCAATAG AGATCAGTCTTCTAGTTGCGTTTTGTACTTTGGTTCGCTCAAT TTTGCAGGAGGAAACCCGTTTTTTCTGACGTAAGGGTGCGCA GTTTGTGAACCAATAGAGAGGTTTTAGAGCTAGAAATAGCAG GTTAAAATAAGGCTAGTCCGTTATCAACTTGAAAAAGTGGCA CCGAGTCGGTGCTTTTTTATTTTTTGTCACTATTGTTATGTAA AATGCCACCTCTGACAGTATGGAACGCAAACTTCTGTCTAGT GGATAGGAACTCTTGTTGTTCTTTGCTAGC | Cassette sequence |
| 25 | GTTCCTGGC | Start sequence (5' of Pci1-Up) |
| 26 | CTTTTGCTGGCCTTTTGCTC | Pci1-Up sequence (primer binding site) |
| 27 | TTAATTAA | Sequence between Pci1-Up and tRNA-Tyr |
| 28 | GTATATGTGTTATGTAGTATACTCTTTCTTCAACAATTAAATA CTCTCGGTAGCCAAGTTGGTTTAAGGCGCAAGACTGTAATTT ATCACTACGAAATCTTGAGATCGGGCGTTCGACTCGCCCCCG GGAGA | tRNA-Tyr |
| 29 | GATGGCCGGCATGGTCCCAGCCTCCTCGCTGGCGCCGGCTGG GCAACACCTTCGGGTGGCGAATGGGACTTT | HDV ribozyme |
| 30 | CTCTGACAATTACTTCCAATGGAATTAGTTTATGTTTGTGAAC CAATAGAGATCAGTCTTCTAGTTGCGTTTTGTACTTTGGTTCG CTCAATTTTGCAGGAGGAAACCCGTTTTTTCTGAC | msd locus |
| 31 | TCTGAGTTACTGTCTGTTTTCCT | msd locus (portion overlaping the vector, not including donor) |
| 32 | ATGCGCACCCTTAGCGAGAGGTTTATCATTAAGGTCAACCTC TGGATGTTGTTTCGGCATCCTGCATTGAATCTGAGTTACTGTC TGTTTTCCT | Vector sequence |
| 33 | CTCTGACAATTACTTCCAATGGAATTAGTTTATGTTTGTGAAC CAATAGAGATCAGTCTTCTAGTTGCGTTTTGTACTTTGGTTCG CTCAATTTTGCAGG | Donor DNA1 |
| 34 | AGGAAACCCGTTTTTTCTGACGTAAGGGTGCGCA | Constant synthesis sequence |
| 35 | GTTTGTGAACCAATAGAGAG | Guide2 sequence |

INFORMAL SEQUENCE LISTING

| SEQ ID NO: | Sequence | Description |
|---|---|---|
| 36 | GTTTTAGAGCTAGAAATAGCAAGTTAAAATAAGGCTAGTCCG TTATCAACTTGAAAAAGTGGCACCGAGTCGGTGCTTTTTT | sgRNA coding sequence |
| 37 | TTTATTTTTTGTCACTATTGTTATGTAAAATGCCACCTCTGAC AGTATGGAACGCAAACTTCTGTCTAGTGGATA | SNR52 terminator |
| 38 | GGAACTCTTGTTGTTCTTT | RPR1 terminator |
| 39 | GCTAGC | End sequence (3' of RPR1 terminator) |
| 40 | PAKLSEPKYKTQLED | Partial ADE1 amino acid sequence (N-terminal to edit site) |
| 41 | SLLVHKHKLIPLEVIVR | Partial ADE1 amino acid sequence (C-terminal to edit site) |

What is claimed is:

1. A retron-guide RNA cassette comprising:
   (a) a retron comprising:
      (i) an msr locus;
      (ii) a first inverted repeat sequence coding region;
      (iii) an msd locus;
      (iv) a donor DNA sequence located within the msd locus; and
      (v) a second inverted repeat sequence coding region; and
   (b) a guide RNA (gRNA) coding region,
   wherein the transcription of the retron-guide RNA cassette produces a retron transcript physically coupled to the gRNA.

2. The cassette of claim 1, wherein the first inverted repeat sequence coding region is located within the 5' end of the msr locus.

3. The cassette of claim 1, wherein the second inverted repeat sequence coding region is located 3' of the msd locus.

4. The cassette of claim 1, wherein the retron encodes an RNA molecule that is capable of self-priming reverse transcription by a reverse transcriptase (RT).

5. The cassette of claim 4, wherein reverse transcription of the RNA molecule results in a multicopy single-stranded DNA (msDNA) molecule that comprises RNA and DNA.

6. The cassette of claim 1, wherein the gRNA coding region is 3' of the retron.

7. The cassette of claim 1, wherein the gRNA coding region is 5' of the retron.

8. The cassette of claim 1, further comprising a ribozyme sequence.

9. The cassette of claim 8, wherein the ribozyme sequence encodes a hepatitis delta virus ribozyme.

10. The cassette of claim 1, wherein the cassette is less than 200 nucleotides in length.

11. The cassette of claim 1, wherein the donor DNA sequence comprises two homology arms, wherein each homology arm has at least about 70% to about 99% similarity to a portion of the sequence of a genetic locus of interest on either side of a nuclease cleavage site.

12. A vector comprising the cassette of claim 1.

13. The vector of claim 12, further comprising a promoter that is operably linked to the cassette.

14. The vector of claim 13, wherein the promoter is inducible.

15. The vector of claim 13, wherein the promoter is selected from the group consisting of an RNA polymerase II promoter, an RNA polymerase III promoter, and a combination thereof.

16. The vector of claim 12, further comprising a reverse transcriptase (RT) coding sequence.

17. The vector of claim 16, further comprising a nuclear localizing sequence located 5' of the RT coding sequence.

18. The vector of claim 12, further comprising a nuclease coding sequence.

19. A retron donor DNA-guide molecule comprising:
(a) a retron transcript comprising:
(i) an msr region;
(ii) a first inverted repeat sequence;
(iii) an msd region;
(iv) a donor DNA sequence coding region located within the msd region; and
(v) a second inverted repeat sequence; and
(b) a guide RNA (gRNA) molecule.

20. The retron donor DNA-guide molecule of claim 19, wherein the first inverted repeat sequence is located within the 5' end of the msr region.

21. The retron donor DNA-guide molecule of claim 19, wherein the second inverted repeat sequence is located 3' of the msd region.

22. The retron donor DNA-guide molecule of claim 19, wherein the retron transcript is capable of self-priming reverse transcription by a reverse transcriptase (RT).

23. The retron donor DNA-guide molecule of claim 19, wherein the retron transcript and gRNA molecule are physically coupled.

24. The retron donor DNA-guide molecule of claim 23, wherein the gRNA molecule is 3' of the retron transcript.

25. The retron donor DNA-guide molecule of claim 23, wherein the gRNA molecule is 5' of the retron transcript.

26. The retron donor DNA-guide molecule of claim 19, further comprising a ribozyme.

27. The retron donor DNA-guide molecule of claim 26, wherein the ribozyme is a hepatitis delta virus ribozyme.

28. The retron donor DNA-guide molecule of claim 19, wherein the retron transcript and gRNA molecule are physically uncoupled after transcription.

29. The retron donor DNA-guide molecule of claim 19, wherein reverse transcription of the retron transcript results in a multicopy single-stranded DNA (msDNA) molecule that comprises RNA and DNA.

30. The retron donor DNA-guide molecule of claim 29, wherein at least some of the RNA content of the msDNA molecule is degraded.

31. The retron donor DNA-guide molecule of claim 19, wherein the donor DNA sequence coding region comprises sequences encoding two homology arms, wherein each homology arm has at least about 70% to about 99% similarity to a portion of the sequence of a genetic locus of interest on either side of a nuclease cleavage site.

32. A host cell comprising the vector of claim 12.

33. A pharmaceutical composition comprising:
(a) the retron-guide RNA cassette of claim 1; and
(b) a pharmaceutically acceptable carrier.

34. The vector of claim 18, wherein the nuclease encoded by the nuclease coding sequence is a CRISPR-associated protein (Cas) nuclease.

35. The vector of claim 34, wherein the Cas nuclease is selected from the group consisting of Cas9, Cpf1, and a combination thereof.

* * * * *

SEQUENCE LISTING

<160> NUMBER OF SEQ ID NOS: 41

<210> SEQ ID NO 1
<211> LENGTH: 21
<212> TYPE: DNA
<213> ORGANISM: Artificial Sequence
<220> FEATURE:
<223> OTHER INFORMATION: Synthetic ADE1 forward primer

<400> SEQUENCE: 1
cattggtggc cagaggtaaa g               21

<210> SEQ ID NO 2
<211> LENGTH: 21
<212> TYPE: DNA
<213> ORGANISM: Artificial Sequence
<220> FEATURE:
<223> OTHER INFORMATION: Synthetic ADE1 reverse primer

<400> SEQUENCE: 2
gtgaggagtt acactggcga c               21

<210> SEQ ID NO 3
<211> LENGTH: 20
<212> TYPE: DNA
<213> ORGANISM: Artificial Sequence
<220> FEATURE:
<223> OTHER INFORMATION: Synthetic ADE1 guide sequence (20 bp)

<400> SEQUENCE: 3
caagtgcaaa gattatgcta               20

<210> SEQ ID NO 4
<211> LENGTH: 921
<212> TYPE: DNA

<213> ORGANISM: Artificial Sequence
<220> FEATURE:
<223> OTHER INFORMATION: Synthetic ADE1 sequence

<400> SEQUENCE: 4

```
atgtcaatta cgaagactga actggacggt atattgccat tggtggccag aggtaaagtt      60
agagacatat atgaggtaga cgctggtacg ttgctgtttg ttgctacgga tcgtatctct     120
gcatatgacg ttattatgga aaacagcatt cctgaaaagg ggatcctatt gaccaaactg     180
tcagagttct ggttcaagtt cctgtccaac gatgttcgta atcatttggt cgacatcgcc     240
ccaggtaaga ctattttcga ttatctacct gcaaaattga gcgaaccaaa gtacaaaacg     300
caactagaag accgctctct attggttcac aaacataaac taattccatt ggaagtaatt     360
gtcagaggct acatcaccgg atctgcttgg aaagagtacg taaaaacagg tactgtgcat     420
ggtttgaaac aacctcaagg acttaaagaa tctcaagagt cccagaacc aatcttcacc      480
ccatcgacca aggctgaaca aggtgaacat gacgaaaaca tctctcctgc ccaggccgct     540
gagctggtgg gtgaagattt gtcacgtaga gtggcagaac tggctgtaaa actgtactcc     600
aagtgcaaag attatgctaa ggagaagggc atcatcatcg cagacactaa attcgaattc     660
ggtattgacg aaaagaccaa tgaaattatt ctagtggacg aggtgctaac gccagactcc     720
tctagattct ggaacggtgc ctcttataag gtaggagaat cccaagattc ttacgataag     780
caattttttaa gagactggct tactgctaat aagttgaacg tgttaacgg cgtcaaaatg      840
ccccaagaca ttgtcgacag gacaagggcc aaatatatag aggcttatga acattgaca      900
gggtctaaat ggtctcacta a                                                921
```

<210> SEQ ID NO 5
<211> LENGTH: 720
<212> TYPE: DNA
<213> ORGANISM: Artificial Sequence
<220> FEATURE:
<223> OTHER INFORMATION: Synthetic eGFP sequence

<400> SEQUENCE: 5

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 6
<211> LENGTH: 45
<212> TYPE: DNA
<213> ORGANISM: Artificial Sequence
<220> FEATURE:
<223> OTHER INFORMATION: Synthetic Fusion linker sequence

<400> SEQUENCE: 6
ggtggaggag gctctggtgg aggcggtagc ggaggcggag ggtcg    45

<210> SEQ ID NO 7
<211> LENGTH: 50
<212> TYPE: DNA
<213> ORGANISM: Artificial Sequence
<220> FEATURE:
<223> OTHER INFORMATION: Synthetic ADE1 homology arm

<400> SEQUENCE: 7
tagagtggca gaactggctg taaaactgta ctccaagtgc aaagattatg    50

<210> SEQ ID NO 8
<211> LENGTH: 38
<212> TYPE: DNA
<213> ORGANISM: Artificial Sequence
<220> FEATURE:
<223> OTHER INFORMATION: Synthetic Donor sequence

<400> SEQUENCE: 8
gttcacactc actagagtga cgaacaatac acgttagc    38

<210> SEQ ID NO 9
<211> LENGTH: 50
<212> TYPE: DNA
<213> ORGANISM: Artificial Sequence
<220> FEATURE:
<223> OTHER INFORMATION: Synthetic ADE1 homology arm

<400> SEQUENCE: 9
ctaaggagaa gggcatcatc atcgcagaca ctaaattcga attcggtatt    50

<210> SEQ ID NO 10
<211> LENGTH: 1716
<212> TYPE: DNA
<213> ORGANISM: Artificial Sequence
<220> FEATURE:
<223> OTHER INFORMATION: Synthetic ADE2 sequence

<400> SEQUENCE: 10
atggattcta gaacagttgg tatattagga gggggacaat tgggacgtat gattgttgag    60
gcagcaaaca ggctcaacat taagacggta atactagatg ctgaaaattc tcctgccaaa    120
caaataagca actccaatga ccacgttaat ggctcctttt ccaatcctct tgatatcgaa    180
aaactagctg aaaaatgtga tgtgctaacg attgagattt agcatgttga tgttcctaca    240
ctaaagaatc ttcaagtaaa acatcccaaa ttaaaaattt acccttctcc agaaacaatc    300
agattgatac aagacaaata tattcaaaaa gagcatttaa tcaaaaatgg tatagcagtt    360
acccaaagtg ttcctgtgga acaagccagt gagacgtccc tattgaatgt tggaagagat    420
ttgggttttc cattcgtctt gaagtcgagg actttggcat acgatggaag aggtaacttc    480
gttgtaaaga ataaggaaat gattccggaa gctttggaag tactgaagga tcgtcctttg    540
tacgccgaaa aatgggcacc atttactaaa gaattagcag tcatgattgt gagatctgtt    600
aacggtttag tgttttctta cccaattgta gagactatcc acaaggacaa tatttgtgac    660
ttatgttatg cgcctgctag agttccggac tccgttcaac ttaaggcgaa gttgttggca    720
gaaaatgcaa tcaatctttt tcccggttgt ggtatatttg gtgtggaaat gttctattta    780
gaaacagggg aattgcttat taacgaaatt gccccaaggc ctcacaactc tggacattat    840

```
accattgatg cttgcgtcac ttctcaattt gaagctcatt tgagatcaat attggatttg    900
ccaatgccaa agaatttcac atctttctcc accattacaa cgaacgccat tatgctaaat    960
gttcttggag acaaacatac aaaagataaa gagctagaaa cttgcgaaag agcattggcg   1020
actccaggtt cctcagtgta cttatatgga aaagagtcta gacctaacag aaaagtaggt   1080
cacataaata ttattgcctc agtatggcg gaatgtgaac aaaggctgaa ctacattaca    1140
ggtagaactg atattccaat caaaatctct gtcgctcaaa agttggactt ggaagcaatg   1200
gtcaaaccat tggttggaat catcatggga tcagactctg acttgccggt aatgtctgcc   1260
gcatgtgcgg ttttaaaaga ttttggcgtt ccatttgaag tgacaatagt ctctgctcat   1320
agaactccac ataggatgtc agcatatgct atttccgcaa gcaagcgtgg aattaaaaca   1380
attatcgctg gagctggtgg ggctgctcac ttgccaggta tggtggctgc aatgacacca   1440
cttcctgtca tcggtgtgcc cgtaaaaggt tcttgtctag atggagtaga ttctttacat   1500
tcaattgtgc aaatgcctag aggtgttcca gtagctaccg tcgctattaa taatagtacg   1560
aacgctgcgc tgttggctgt cagactgctt ggcgcttatg attcaagtta tacaacgaaa   1620
atggaacagt ttttattaaa gcaagaagaa gaagttcttg tcaaagcaca aaagttagaa   1680
actgtcggtt acgaagctta tctagaaaac aagtaa                             1716

<210> SEQ ID NO 11
<211> LENGTH: 50
<212> TYPE: DNA
<213> ORGANISM: Artificial Sequence
<220> FEATURE:
<223> OTHER INFORMATION: Synthetic ADE2 homology arm

<400> SEQUENCE: 11
tggaaatgtt ctatttagaa acaggggaat tgcttattaa cgaaattgcc              50

<210> SEQ ID NO 12
<211> LENGTH: 50
<212> TYPE: DNA
<213> ORGANISM: Artificial Sequence
<220> FEATURE:
<223> OTHER INFORMATION: Synthetic ADE2 homology arm

<400> SEQUENCE: 12
tgaaggcctc acaactctgg acattatacc attgatgctt gcgtcacttc              50

<210> SEQ ID NO 13
<211> LENGTH: 18
<212> TYPE: DNA
<213> ORGANISM: Artificial Sequence
<220> FEATURE:
<223> OTHER INFORMATION: Synthetic Guide 3 0.74

<400> SEQUENCE: 13
attaacgaaa ttgcccca                                                 18

<210> SEQ ID NO 14
<211> LENGTH: 1338
<212> TYPE: DNA
<213> ORGANISM: Artificial Sequence
<220> FEATURE:
<223> OTHER INFORMATION: Synthetic Retron Ec86 sequence

<400> SEQUENCE: 14
taactatgat aagattccgt atgcgcaccc ttagcgagag gtttatcatt aaggtcaacc    60
tctggatgtt gtttcggcat cctgcattga atctgagtta ctgtctgttt tccttgttgg   120
```

```
aacggagagc atcgcctgat gctctccgag ccaaccagga aacccgtttt ttctgacgta      180
agggtgcgca actttcatga aatccgctga atatttgaac acttttagat tgagaaatct      240
cggcctacct gtcatgaaca atttgcatga catgtctaag gcgactcgca tatctgttga      300
aacacttcgg ttgttaatct atacagctga ttttcgctat aggatctaca ctgtagaaaa      360
gaaaggccca gagaagagaa tgagaaccat ttaccaacct tctcgagaac ttaaagcctt      420
acaaggatgg gttctacgta acattttaga taaactgtcg tcatctcctt tttctattgg      480
atttgaaaag caccaatcta ttttgaataa tgctaccccg catattgggg caaactttat      540
actgaatatt gatttggagg atttttttccc aagtttaact gctaacaaag tttttggagt      600
gttccattct cttggttata atcgactaat atcttcagtt ttgacaaaaa tatgttgtta      660
taaaaatctg ctaccacaag gtgctccatc atcacctaaa ttagctaatc taatatgttc      720
taaacttgat tatcgtattc agggttatgc aggtagtcgg ggcttgatat atacgagata      780
tgccgatgat ctcaccttat ctgcacagtc tatgaaaaag gttgttaaag cacgtgattt      840 tttatttct ataatcccaa gtgaaggatt ggttattaac tcaaaaaaaa cttgtattag      900
tgggcctcgt agtcagagga aagttacagg tttagttatt tcacaagaga agttgggat       960 aggtagagaa aaatataaag aaattagagc aaagatacat catatatttt gcggtaagtc     1020
ttctgagata gaacacgtta ggggatggtt gtcatttatt ttaagtgtgg attcaaaaag     1080
ccataggaga ttaataactt atattagcaa attagaaaaa aaatatggaa agaacccttt     1140
aaataaagcg aagacctaat ggtcttcgtt taaaaactaa agctcatagg ttgaaaaatt     1200
gagcacttct tcgtccaacc agttatttag ttcctgcaat cgtttctgca ggggcatcaa     1260
ttcgtttctt acgaatacct tgctagcctt ctccacatcc caaaccccc cgacattatt     1320 aggcataatt cccatcat                                                   1338

<210> SEQ ID NO 15
<211> LENGTH: 20
<212> TYPE: DNA
<213> ORGANISM: Artificial Sequence
<220> FEATURE:
<223> OTHER INFORMATION: Synthetic Plasmid start sequence

<400> SEQUENCE: 15
taactatgat aagattccgt                                                   20

<210> SEQ ID NO 16
<211> LENGTH: 12
<212> TYPE: DNA
<213> ORGANISM: Artificial Sequence
<220> FEATURE:
<223> OTHER INFORMATION: Synthetic Inverted repeat sequence

<400> SEQUENCE: 16
tgcgcaccct ta                                                           12

<210> SEQ ID NO 17
<211> LENGTH: 12
<212> TYPE: DNA
<213> ORGANISM: Artificial Sequence
<220> FEATURE:
<223> OTHER INFORMATION: Synthetic Second inverted repeat

<400> SEQUENCE: 17
taagggtgcg ca                                                           12
```

<210> SEQ ID NO 18
<211> LENGTH: 82
<212> TYPE: DNA
<213> ORGANISM: Artificial Sequence
<220> FEATURE:
<223> OTHER INFORMATION: Synthetic msr locus

<400> SEQUENCE: 18

```
atgcgcaccc ttagcgagag gtttatcatt aaggtcaacc tctggatgtt gtttcggcat      60
cctgcattga atctgagtta ct                                               82
```

<210> SEQ ID NO 19
<211> LENGTH: 86
<212> TYPE: DNA
<213> ORGANISM: Artificial Sequence
<220> FEATURE:
<223> OTHER INFORMATION: Synthetic msd locus

<400> SEQUENCE: 19

```
tctgagttac tgtctgtttt ccttgttgga acggagagca tcgcctgatg ctctccgagc      60
caaccaggaa acccgttttt tctgac                                           86
```

<210> SEQ ID NO 20
<211> LENGTH: 41
<212> TYPE: DNA
<213> ORGANISM: Artificial Sequence
<220> FEATURE:
<223> OTHER INFORMATION: Synthetic Replaceable region

<400> SEQUENCE: 20

```
tgttggaacg gagagcatcg cctgatgctc tccgagccaa c                          41
```

<210> SEQ ID NO 21
<211> LENGTH: 963
<212> TYPE: DNA
<213> ORGANISM: Artificial Sequence
<220> FEATURE:
<223> OTHER INFORMATION: Synthetic Ec86 reverse transcriptase
    (optimized)

<400> SEQUENCE: 21

```
atgaaatccg ctgaatattt gaacactttt agattgagaa atctcggcct acctgtcatg      60
aacaatttgc atgacatgtc taaggcgact cgcatatctg ttgaaacact tcggttgtta     120
atctatacag ctgatttcg ctataggatc tacactgtag aaaagaaagg cccagagaag      180
agaatgagaa ccattaccca accttctcga gaacttaaag ccttacaagg atgggttcta     240
cgtaacattt tagataaact gtcgtcatct cctttttcta ttggatttga aaagcaccaa     300
tctattttga ataatgctac cccgcatatt ggggcaaact ttatactgaa tattgatttg     360
gaggattttt tcccaagttt aactgctaac aaagttttttg gagtgttcca ttctcttggt     420
tataatcgac taatatcttc agttttgaca aaaatatgtt gttataaaaa tctgctacca     480
caaggtgctc catcatcacc taaattagct aatctaatat gttctaaact tgattatcgt     540
attcagggtt atgcaggtag tcggggcttg atatatacga gatatgccga tgatctcacc     600
ttatctgcac agtctatgaa aaaggttgtt aaagcacgtg attttttatt ttctataatc     660
ccaagtgaag gattggttat taactcaaaa aaaacttgta ttagtgggcc tcgtagtcag     720
aggaaagtta caggtttagt tatttcacaa gagaaagttg ggataggtag agaaaaatat     780
aaagaaatta gagcaaagat acatcatata ttttgcggta agtcttctga gatagaacac     840
```

```
gttaggggat ggttgtcatt tattttaagt gtggattcaa aaagccatag gagattaata    900
acttatatta gcaaattaga aaaaaaatat ggaaagaacc ctttaaataa agcgaagacc    960
taa                                                                 963
```

<210> SEQ ID NO 22
<211> LENGTH: 6
<212> TYPE: DNA
<213> ORGANISM: Artificial Sequence
<220> FEATURE:
<223> OTHER INFORMATION: Synthetic Sequence between second inverted
      repeat sequence and Ec86 reverse transcriptase sequence

<400> SEQUENCE: 22

```
actttc                                                                6
```

<210> SEQ ID NO 23
<211> LENGTH: 179
<212> TYPE: DNA
<213> ORGANISM: Artificial Sequence
<220> FEATURE:
<223> OTHER INFORMATION: Synthetic Sequence located 3' of EC86 reverse
      transcriptase sequence

<400> SEQUENCE: 23

```
tggtcttcgt tttaaaacta aagctcatag gttgaaaaat tgagcacttc ttcgtccaac     60
cagttattta gttcctgcaa tcgtttctgc aggggcatca attcgtttct tacgaatacc    120
ttgctagcct tctccacatc cccaaacccc ccgacattat taggcataat tcccatcat    179
```

<210> SEQ ID NO 24
<211> LENGTH: 669
<212> TYPE: DNA
<213> ORGANISM: Artificial Sequence
<220> FEATURE:
<223> OTHER INFORMATION: Synthetic Cassette sequence

<400> SEQUENCE: 24

```
gttcctggcc ttttgctggc cttttgctct taattaagta tatgtgttat gtagtatact     60 cttttcttcaa caattaaata ctctcggtag ccaagttggt ttaaggcgca agactgtaat   120
ttatcactac gaaatcttga gatcgggcgt tcgactcgcc cccgggagag atggccggca   180
tggtcccagc ctcctcgctg gcgccggctg ggcaacacct tcgggtggcg aatgggactt   240
tatgcgcacc cttagcgaga ggtttatcat taaggtcaac ctctggatgt tgtttcggca   300
tcctgcattg aatctgagtt actgtctgtt ttcctctctg acaattactt ccaatggaat   360
tagtttatgt ttgtgaacca atagagatca gtcttctagt tgcgttttgt actttggttc   420
gctcaatttt gcaggaggaa acccgttttt tctgacgtaa gggtgcgcag tttgtgaacc   480
aatagagagg ttttagagct agaaatagca agttaaaata aggctagtcc gttatcaact   540
tgaaaaagtg gcaccgagtc ggtgcttttt ttatttttg tcactattgt tatgtaaaat   600
gccacctctg acagtatgga acgcaaactt ctgtctagtg ataggaact cttgttgttc   660 tttgctagc                                                           669
```

<210> SEQ ID NO 25
<211> LENGTH: 9
<212> TYPE: DNA
<213> ORGANISM: Artificial Sequence
<220> FEATURE:
<223> OTHER INFORMATION: Synthetic Start sequence (5' of Pci1-Up)

<400> SEQUENCE:

```
gttcctggc                                                                    9

<210> SEQ ID NO 26
<211> LENGTH: 20
<212> TYPE: DNA
<213> ORGANISM: Artificial Sequence
<220> FEATURE:
<223> OTHER INFORMATION: Synthetic Pci1-Up sequence (primer binding
      site)

<400> SEQUENCE: 26
cttttgctgg cctttttgctc                                                       20

<210> SEQ ID NO 27
<211> LENGTH: 8
<212> TYPE: DNA
<213> ORGANISM: Artificial Sequence
<220> FEATURE:
<223> OTHER INFORMATION: Synthetic Sequence between Pci1-Up and tRNA-Tyr

<400> SEQUENCE: 27 ttaattaa                                                                     8

<210> SEQ ID NO 28
<211> LENGTH: 132
<212> TYPE: DNA
<213> ORGANISM: Artificial Sequence
<220> FEATURE:
<223> OTHER INFORMATION: Synthetic tRNA-Tyr

<400> SEQUENCE: 28
gtatatgtgt tatgtagtat actctttctt caacaattaa atactctcgg tagccaagtt            60
ggtttaaggc gcaagactgt aatttatcac tacgaaatct tgagatcggg cgttcgactc           120
gcccccggga ga                                                              132

<210> SEQ ID NO 29
<211> LENGTH: 72
<212> TYPE: DNA
<213> ORGANISM: Artificial Sequence
<220> FEATURE:
<223> OTHER INFORMATION: Synthetic HDV ribozyme

<400> SEQUENCE: 29
gatggccggc atggtcccag cctcctcgct ggcgccggct gggcaacacc ttcgggtggc            60
gaatgggact tt                                                               72

<210> SEQ ID NO 30
<211> LENGTH: 121
<212> TYPE: DNA
<213> ORGANISM: Artificial Sequence
<220> FEATURE:
<223> OTHER INFORMATION: Synthetic msd locus

<400> SEQUENCE: 30
ctctgacaat tacttccaat ggaattagtt tatgtttgtg aaccaataga gatcagtctt            60
ctagttgcgt tttgtacttt ggttcgctca attttgcagg aggaaacccg ttttttctga           120
c                                                                          121

<210> SEQ ID NO 31
<211> LENGTH: 23
<212> TYPE: DNA
<213> ORGANISM: Artificial Sequence
```

```
<220> FEATURE:
<223> OTHER INFORMATION: Synthetic msd locus (portion overlaping the
      vector, not including donor)

<400> SEQUENCE: 31
tctgagttac tgtctgtttt cct                                             23

<210> SEQ ID NO 32
<211> LENGTH: 94
<212> TYPE: DNA
<213> ORGANISM: Artificial Sequence
<220> FEATURE:
<223> OTHER INFORMATION: Synthetic Vector sequence

<400> SEQUENCE: 32
atgcgcaccc ttagcgagag gtttatcatt aaggtcaacc tctggatgtt gtttcggcat     60
cctgcattga atctgagtta ctgtctgttt tcct                                 94

<210> SEQ ID NO 33
<211> LENGTH: 100
<212> TYPE: DNA
<213> ORGANISM: Artificial Sequence
<220> FEATURE:
<223> OTHER INFORMATION: Synthetic Donor DNA1

<400> SEQUENCE: 33
ctctgacaat tacttccaat ggaattagtt tatgtttgtg aaccaataga gatcagtctt     60
ctagttgcgt tttgtacttt ggttcgctca attttgcagg                          100

<210> SEQ ID NO 34
<211> LENGTH: 34
<212> TYPE: DNA
<213> ORGANISM: Artificial Sequence
<220> FEATURE:
<223> OTHER INFORMATION: Synthetic Constant synthesis sequence

<400> SEQUENCE: 34
aggaaacccg ttttttctga cgtaagggtg cgca                                 34

<210> SEQ ID NO 35
<211> LENGTH: 20
<212> TYPE: DNA
<213> ORGANISM: Artificial Sequence
<220> FEATURE:
<223> OTHER INFORMATION: Synthetic Guide2 sequence

<400> SEQUENCE: 35
gtttgtgaac caatagagag                                                 20

<210> SEQ ID NO 36
<211> LENGTH: 82
<212> TYPE: DNA
<213> ORGANISM: Artificial Sequence
<220> FEATURE:
<223> OTHER INFORMATION: Synthetic sgRNA coding sequence

<400> SEQUENCE: 36
gttttagagc tagaaatagc aagttaaaat aaggctagtc cgttatcaac ttgaaaaagt     60
ggcaccgagt cggtgctttt tt                                              82
```

```
<210> SEQ ID NO 37
<211> LENGTH: 75
<212> TYPE: DNA
<213> ORGANISM: Artificial Sequence
<220> FEATURE:
<223> OTHER INFORMATION: Synthetic SNR52 terminator

<400> SEQUENCE: 37
tttatttttt gtcactattg ttatgtaaaa tgccacctct gacagtatgg aacgcaaact      60
tctgtctagt ggata                                                      75

<210> SEQ ID NO 38
<211> LENGTH: 19
<212> TYPE: DNA
<213> ORGANISM: Artificial Sequence
<220> FEATURE:
<223> OTHER INFORMATION: Synthetic RPR1 terminator

<400> SEQUENCE: 38
ggaactcttg ttgttctttt                                                 19

<210> SEQ ID NO 39
<211> LENGTH: 6
<212> TYPE: DNA
<213> ORGANISM: Artificial Sequence
<220> FEATURE:
<223> OTHER INFORMATION: Synthetic End sequence (3' of RPR1 terminator)

<400> SEQUENCE: 39 gctagc                                                                6

<210> SEQ ID NO 40
<211> LENGTH: 15
<212> TYPE: PRT
<213> ORGANISM: Artificial Sequence
<220> FEATURE:
<223> OTHER INFORMATION: Synthetic Partial ADE1 amino acid sequence
      (N-terminal to edit site)

<400> SEQUENCE: 40

Pro Ala Lys Leu Ser Glu Pro Lys Tyr Lys Thr Gln Leu Glu Asp
1               5                   10                  15

<210> SEQ ID NO 41
<211> LENGTH: 17
<212> TYPE: PRT
<213> ORGANISM: Artificial Sequence
<220> FEATURE:
<223> OTHER INFORMATION: Synthetic Partial ADE1 amino acid sequence
      (C-terminal to edit site)

<400> SEQUENCE: 41

Ser Leu Leu Val His Lys His Lys Leu Ile Pro Leu Glu Val Ile Val
1               5                   10                  15

Arg
```